(12) United States Patent  
Bonfanti et al.

(10) Patent No.: US 11,702,387 B2  
(45) Date of Patent: *Jul. 18, 2023

(54) SUBSTITUTED INDOLINE DERIVATIVES AS DENGUE VIRAL REPLICATION INHIBITORS

(71) Applicants: Janssen Pharmaceuticals, Inc., Titusville, NJ (US); Katholieke Universiteit Leuven, Leuven (BE)

(72) Inventors: Jean-François Bonfanti, Issy-les-Moulineaux (FR); Bart Rudolf Romanie Kesteleyn, Beerse (BE); Dorothée Alice Marie-Eve Bardiot, Leuven (BE); Arnaud Didier M Marchand, Leuven (BE); Erwin Coesemans, Beerse (BE); Benoît Christian Albert Ghislain De Boeck, Beerse (BE); Pierre Jean-Marie Bernard Raboisson, Beerse (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 70 days.

This patent is subject to a terminal disclaimer.

(21) Appl. No.: 17/334,432

(22) Filed: May 28, 2021

(65) Prior Publication Data

US 2021/0300868 A1     Sep. 30, 2021

Related U.S. Application Data

(63) Continuation of application No. 16/614,715, filed as application No. PCT/EP2018/063029 on May 18, 2018, now Pat. No. 11,053,196.

(30) Foreign Application Priority Data

May 22, 2017   (EP) ..................................... 17172247

(51) Int. Cl.
  *C07D 209/04*     (2006.01)
  *A61K 45/06*      (2006.01)
  (Continued)

(52) U.S. Cl.
  CPC ............ *C07D 209/04* (2013.01); *A61P 31/14* (2018.01); *C07D 495/04* (2013.01); *A61K 45/06* (2013.01); *C07B 2200/07* (2013.01)

(58) Field of Classification Search
  CPC .................................................. C07D 209/04
  See application file for complete search history.

(56) References Cited

U.S. PATENT DOCUMENTS 6,177,416 B1   1/2001  Denney et al.
7,601,735 B2  10/2009  Tyms et al.
  (Continued)

FOREIGN PATENT DOCUMENTS

JP    2012-206959 A   10/2012
WO      99-21559 A1    5/1999
  (Continued)

OTHER PUBLICATIONS

ACS on STN Registry No. 931079-09-3, Apr. 20, 2007.
  (Continued)

*Primary Examiner* — Valerie Rodriguez-Garcia

(74) *Attorney, Agent, or Firm* — Burns & Levinson, LLP; Shawn P. Foley; Chris Lorenc

(57) ABSTRACT

The present invention concerns substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

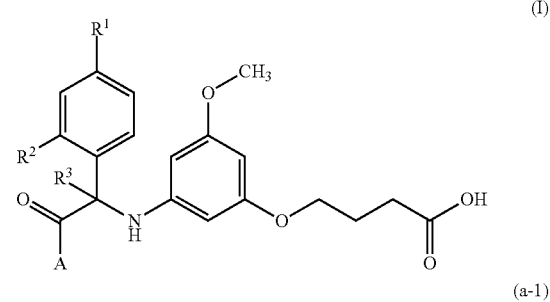

(I)

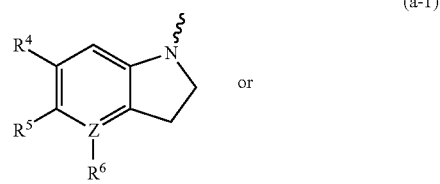

(a-1) or

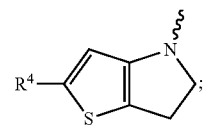

(a-2)

14 Claims, No Drawings

Specification includes a Sequence Listing.

(51) Int. Cl.
*A61P 31/14* (2006.01)
*C07D 495/04* (2006.01)

(56) References Cited

U.S. PATENT DOCUMENTS

| | | | |
|---|---|---|---|
| 8,143,259 | B2 | 3/2012 | Colburn et al. |
| 8,299,056 | B2 | 10/2012 | Bahmanyar et al. |
| 8,324,217 | B2 | 12/2012 | Colburn et al. |
| 8,524,764 | B2 | 9/2013 | Canales et al. |
| 8,884,030 | B2 | 11/2014 | Canales et al. |
| 8,993,604 | B2 | 3/2015 | Byrd et al. |
| 9,029,376 | B2 | 5/2015 | Byrd et al. |
| 9,522,923 | B2 | 12/2016 | Richards et al. |
| 9,944,598 | B2 | 4/2018 | Kesteleyn et al. |
| 10,029,984 | B2 | 7/2018 | Kesteleyn et al. |
| 10,064,870 | B2 | 9/2018 | Rajagopalan et al. |
| 10,071,961 | B2 | 9/2018 | Vandyck et al. |
| 10,117,850 | B2 | 11/2018 | Griffioen et al. |
| 10,209,902 | B1 | 2/2019 | Kesteleyn et al. |
| 10,323,026 | B2 | 6/2019 | Ikeda et al. |
| 10,550,123 | B2 | 2/2020 | Bardiot et al. |
| 10,689,340 | B2 * | 6/2020 | Kesteleyn ............ C07D 209/26 |
| 11,180,450 | B2 * | 11/2021 | Kesteleyn ............ C07D 209/08 |
| 2005/0239821 | A1 | 10/2005 | Neyts et al. |
| 2006/0194835 | A1 | 8/2006 | Dugourd et al. |
| 2006/0211698 | A1 | 9/2006 | Botyanszki et al. |
| 2008/0318338 | A1 | 12/2008 | Kamal et al. |
| 2013/0023532 | A1 | 1/2013 | Casillas et al. |
| 2014/0213586 | A1 | 7/2014 | Bardiot et al. |
| 2016/0297810 | A1 | 10/2016 | Bardiot et al. |
| 2017/0002006 | A1 | 1/2017 | Corte et al. |
| 2017/0096429 | A1 | 4/2017 | Corte et al. |
| 2017/0281633 | A1 | 10/2017 | Boylan et al. |
| 2017/0281766 | A1 | 10/2017 | Wiltzius |
| 2017/0283500 | A1 | 10/2017 | Wiltzuis et al. |
| 2017/0298017 | A1 | 10/2017 | Kesteleyn et al. |
| 2018/0256544 | A1 | 9/2018 | Kesteleyn et al. |
| 2018/0256545 | A1 | 9/2018 | Kesteleyn et al. |
| 2018/0346419 | A1 | 12/2018 | Kesteleyn et al. |
| 2019/0104738 | A1 | 4/2019 | Narine et al. |
| 2019/0112266 | A1 | 4/2019 | Kesteleyn et al. |
| 2019/0183931 | A1 | 6/2019 | Bakker et al. |

FOREIGN PATENT DOCUMENTS

| | | |
|---|---|---|
| WO | 02089730 A2 | 11/2002 |
| WO | 02089780 A2 | 11/2002 |
| WO | 03050295 A2 | 6/2003 |
| WO | 2006076529 A1 | 7/2006 |
| WO | 2009149054 A1 | 12/2009 |
| WO | 2010021378 A1 | 2/2010 |
| WO | 2010021878 A1 | 2/2010 |
| WO | 2010027500 A1 | 3/2010 |
| WO | 2010091413 A1 | 8/2010 |
| WO | 2011037643 A1 | 3/2011 |
| WO | 2011088303 A1 | 7/2011 |
| WO | 2011120025 A1 | 9/2011 |
| WO | 2013045516 A1 | 4/2013 |
| WO | 2014154682 A1 | 10/2014 |
| WO | 2016050831 A1 | 4/2016 |
| WO | 2016050841 A1 | 4/2016 |
| WO | 2016053455 A1 | 4/2016 |
| WO | 2017046255 A1 | 3/2017 |
| WO | 2017046258 A1 | 3/2017 |
| WO | 2017079216 A1 | 5/2017 |
| WO | 2017167832 A1 | 10/2017 |
| WO | 2017167950 A1 | 10/2017 |
| WO | 2017167951 A1 | 10/2017 |
| WO | 2017167952 A1 | 10/2017 |
| WO | 2017167953 A1 | 10/2017 |
| WO | 2017171100 A1 | 10/2017 |
| WO | 2017173206 A1 | 10/2017 |
| WO | 2017173256 A1 | 10/2017 |
| WO | 2017173384 A1 | 10/2017 |
| WO | 2017173410 A1 | 10/2017 |
| WO | 2018178238 A1 | 10/2018 |
| WO | 2018178240 A1 | 10/2018 |
| WO | 2018215315 A1 | 11/2018 |

OTHER PUBLICATIONS

ACS on STN Registry No. 931007-71-5, Apr. 19, 2007.
ACS on STN Registry No. 930910-25-1, Apr. 19, 2007.
ACS on STN Registry No. 930724-99-5, Apr. 18, 2007.
ACS on STN Registry No. 930463-83-5, Apr. 17, 2007.
ACS on STN Registry No. 925399-60-6, Mar. 7, 2007.
ACS on STN Registry No. 920950-24-9, Feb. 14, 2007.
ACS on STN Registry No. 920926-40-5, Feb. 14, 2007.
ACS on STN Registry No. 920888-80-8, Feb. 14, 2007.
ACS on STN Registry No. 920870-55-9, Feb. 14, 2007/.
ACS on STN Registry No. 920827-69-6, Feb. 14, 2007.
ACS on STN Registry No. 920696-97-5, Feb. 13, 2007.
ACS on STN Registry No. 920694-81-1, Feb. 13, 2007.
ACS on STN Registry No. 920668-38-8, Feb. 13, 2007.
ACS on STN Registry No. 879164-92-8, Apr. 4, 2006.
ACS on STN Registry No. 878462-38-5, Mar. 29, 2006.
ACS on STN Registry No. 853320-15-7, Jun. 30, 2005.
Banker, et al., (1996) Modern Pharmaceuticals, 3rd Edition, Revised and Expanded, p. 596.
Boltromeyuk V.V., Obshchaya khimiya (General Chemistry), Minsk, Vysheyshaya shkola, 2012, p. 65)(translation).
EP Search Report dated Nov. 19, 2019 from European Patent Appln. No. EP 19183201.3.
Examination Report dated Jan. 7, 2020 from Indian Patent Appln. No. 201727014547.
Ian Stansfield et al., Development of carboxylic acid replacements in indole-N-acetamide inhibitors of hepatitis virus NS5B polymerase, Bioorganic & Medicinal Chemistry Letters, 17, (2007), 5143-5149, ScienceDirect (2007) www.sciencedirect.com, internet.
Japanese Office Action dated Jun. 2, 2020 from Japanese Patent Appln. JP2017-243354 (English Language translation).
Lidia Moreira Lima et al., Bioisosterism: A Useful Strategy for Molecular Modification and Drug Design, Current Medicinal Chemistry, Bentham Science Publishers Ltd., (2005) 12, pp. 23-39.
N.C.B.I.: "qHTS for inhibitors of binding or entry into ceils for Marburg Virus," Pubchem Bioassay Record AID 540276, Jul. 2011, 13 pages, XP55641386, Retrieved from the internet:L https://pubchem.ncbi.lnlm.nih.gov/bioassay/540276.
Registry No. 924715-04-8, entered in STN on Mar. 4, 2007.
Registry No. 1012956-97-6, entered in STN on Apr. 8, 2008.
Registry No. 1277962-26-1, entered in STN on Apr. 10, 2011.
Registry No. 1386200-09-4, entered in STN on Aug. 3, 2012.
Registry No. 1386766-68-2, entered in STN on Aug. 6, 2012.
Registry No. 1388629-42-2, entered in STN on Aug. 9, 2012.
Registry No. 1388775-15-2, entered in STN on Aug. 9, 2012.
Registry No. 1388903-86-3, entered in STN on Aug. 14, 2012.
"Solvation," Wikipedia, at internet address: https//en.wikipedia.org/wiki/Solvation, web page last edited on Mar. 13, 2019, 6 pages.
Wolff et al., Burger's Medicinal Chemistry and Drug Discovery, 5th Ed. part 1, pp. 975-977 (1995).
PCT International Search Report and Written Opinion dated Jul. 20, 2018 in connection with PCT International Application No. PCT/EP2018/063029.
Prasad L. Polavarapu, et al., Intrinsic Rotation and Molecular Structure, Chirality 15:L S143-S149 (2003).
Prevention, Dengue, Centers for Disease Control and Prevention (Sep. 27, 2012) https://www.cdc.govidengue/prevention/index.html, internet.
N.C.B.I.: "qHTS for inhibitors of binding or entry into cells for Marburg Virus," Pubchem Bioassay Record AID 540276, Jul. 2011, 13 pages, XP55641386, Retrieved from the internet:L https://pubchem.ncbi.lnlm.nih.gov/bioassay/540276.
Registry No. 1388908-86-8, entered in STN on Aug. 14, 2012.
Opposition filed in Ecuadorian Patent Application No. SENADI-2019-83640 (English language translation).

(56) References Cited

OTHER PUBLICATIONS

Opposition filed in Ecuadorian Patent Application No. SENADI-2019-83621 (English language translation).

\* cited by examiner

SEQUENCE LISTING

<160> NUMBER OF SEQ ID NOS: 14

<210> SEQ ID NO 1
<211> LENGTH: 19
<212> TYPE: DNA
<213> ORGANISM: Dengue virus

<400> SEQUENCE: 1
cggttagagg agacccctc                                             19

<210> SEQ ID NO 2
<211> LENGTH: 21
<212> TYPE: DNA
<213> ORGANISM: Dengue virus

<400> SEQUENCE: 2
gagacagcag gatctctggt c                                          21

<210> SEQ ID NO 3
<211> LENGTH: 28
<212> TYPE: DNA
<213> ORGANISM: Dengue virus

<400> SEQUENCE: 3
aaggactaga ggttagagga gaccccccc                                  28

<210> SEQ ID NO 4
<211> LENGTH: 18
<212> TYPE: DNA
<213> ORGANISM: Dengue virus

<400> SEQUENCE: 4
ggccaggtca tcaccatt                                              18

<210> SEQ ID NO 5
<211> LENGTH: 21
<212> TYPE: DNA
<213> ORGANISM: Dengue virus

<400> SEQUENCE: 5
atgtccacgt cacacttcat g                                          21

<210> SEQ ID NO 6
<211> LENGTH: 21
<212> TYPE: DNA

```
<213> ORGANISM: Dengue virus

<400> SEQUENCE: 6
ttccgctgcc ctgaggctct c                                              21

<210> SEQ ID NO 7
<211> LENGTH: 20
<212> TYPE: DNA
<213> ORGANISM: Dengue virus

<400> SEQUENCE: 7
tcggagccgg agtttacaaa                                                20

<210> SEQ ID NO 8
<211> LENGTH: 20
<212> TYPE: DNA
<213> ORGANISM: Dengue virus

<400> SEQUENCE: 8
tcttaacgtc cgcccatgat                                                20

<210> SEQ ID NO 9
<211> LENGTH: 19
<212> TYPE: DNA
<213> ORGANISM: Dengue virus

<400> SEQUENCE: 9
attccacaca atgtggcat                                                 19

<210> SEQ ID NO 10
<211> LENGTH: 23
<212> TYPE: DNA
<213> ORGANISM: Dengue virus

<400> SEQUENCE: 10
ggatagacca gagatcctgc tgt                                            23

<210> SEQ ID NO 11
<211> LENGTH: 20
<212> TYPE: DNA
<213> ORGANISM: Dengue virus

<400> SEQUENCE: 11
cattccattt tctggcgttc                                                20

<210> SEQ ID NO 12
<211> LENGTH: 20
<212> TYPE: DNA
<213> ORGANISM: Dengue virus

<400> SEQUENCE: 12
caatccatct tgcggcgctc                                                20

<210> SEQ ID NO 13
<211> LENGTH: 20
<212> TYPE: DNA
<213> ORGANISM: Dengue virus

<400> SEQUENCE: 13
cagcatcatt ccaggcacag                                                20

<210> SEQ ID NO 14
<211> LENGTH: 20
```

```
<212> TYPE: DNA
<213> ORGANISM: Dengue virus

<400> SEQUENCE: 14
caacatcaat ccaggcacag                                              20
```

SUBSTITUTED INDOLINE DERIVATIVES AS DENGUE VIRAL REPLICATION INHIBITORS

RELATED APPLICATIONS

This application is a continuation of U.S. patent application Ser. No. 16/614,715, filed Nov. 18, 2019, which is a U.S. national stage entry under 35 U.S.C. § 371 of PCT International Patent Application No. PCT/EP2018/063029 filed May 18, 2018, which claims priority to European Patent Application 17172247.3 filed May 22, 2017, the contents of which are incorporated herein by reference in their entirety.

The present invention relates to substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Dengvaxia®, the dengue vaccine produced by Sanofi Pasteur was first approved in Mexico and has received in the meantime approval in more countries. Nevertheless, the vaccine leaves considerable room for improvement due to limited efficacy, especially against DENV-1 and -2, low efficacy in flavivirus-naïve subjects and the lengthy dosing schedule.

Despite these shortcomings, the vaccine is a game changer in endemic settings as it will offer protection to a large part of the population, but likely not to very young infants, who bear the largest burden of dengue. In addition, the dosing schedule and very limited efficacy in flavivirus-naïve subjects make it unsuitable and likely not worthwhile/cost-effective for travelers from non-endemic areas to dengue-endemic areas. The above mentioned shortcomings of the dengue vaccines are the reason why there is a need for a pre-exposure prophylactic dengue antiviral.

Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

WO-2010/021878 discloses 2-phenylpyrrolidine and indoline derivatives as cold menthol receptor antagonists for treatment of inflammatory and central diseases. WO-2013/045516 discloses indole and indoline derivatives for use in the treatment of dengue viral infections.

The present invention now provides compounds, substituted indoline derivatives, which show high potent activity against all four (4) serotypes of the Dengue virus.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration an effective amount of one or more such compounds, or a pharmaceutically acceptable salt thereof optionally in combination with one or more other medicines, like another antiviral agent, to a patient in need thereof.

The present invention concerns compounds of formula (I), including any stereochemically isomeric form thereof:

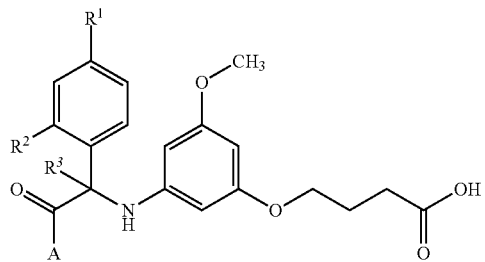

(I)

wherein
A is

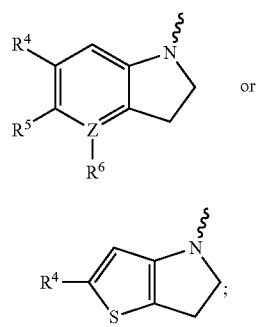

wherein
R$^1$ is chloro, R$^2$ is hydrogen, R$^3$ is hydrogen, A is (a-1), R$^4$ is pentafluorosulfanyl, R$^5$ is hydrogen, Z is carbon, and R$^6$ is hydrogen; or
R$^1$ is chloro, R$^2$ is hydrogen, R$^3$ is hydrogen, A is (a-1), R$^4$ is trifluoromethyl, R$^5$ is hydrogen, Z is carbon, and R$^6$ is methyl; or
R$^1$ is chloro, R$^2$ is hydrogen, R$^3$ is hydrogen, A is (a-1), R$^4$ is trifluoromethyl, R$^5$ is fluoro, Z is carbon, and R$^6$ is hydrogen; or
R$^1$ is chloro, R$^2$ is hydrogen, R$^3$ is hydrogen, A is (a-1), R$^4$ is trifluoromethoxy, R$^5$ is hydrogen, Z is carbon, and R$^6$ is methyl; or
R$^1$ is chloro, R$^2$ is hydrogen, R$^3$ is hydrogen, A is (a-1), R$^4$ is trifluoromethoxy, R$^5$ is fluoro, Z is carbon, and R$^6$ is hydrogen; or
R$^1$ is fluoro, R$^2$ is methoxy, R$^3$ is hydrogen, A is (a-1), R$^4$ is trifluoromethoxy, R$^5$ is hydrogen, Z is carbon, and R$^6$ is hydrogen; or
R$^1$ is chloro, R$^2$ is hydrogen, R$^3$ is deuterium, A is (a-1), R$^4$ is trifluoromethoxy, R$^5$ is hydrogen, Z is carbon, and R$^6$ is hydrogen; or
R$^1$ is chloro, R$^2$ is —OCH$_2$CH$_2$OH, R$^3$ is hydrogen, A is (a-1), R$^4$ is trifluoromethoxy, R$^5$ is hydrogen, Z is carbon, and R$^6$ is hydrogen; or
R$^1$ is chloro, R$^2$ is hydrogen, R$^3$ is hydrogen, A is (a-1), R$^4$ is trifluoromethyl, R$^5$ is methoxy, Z is nitrogen, and R$^6$ is absent; or
R$^1$ is chloro, R$^2$ is hydrogen, R$^3$ is hydrogen, A is (a-2), and R$^4$ is trifluoromethyl; or
R$^1$ is chloro, R$^2$ is hydrogen, R$^3$ is hydrogen, A is (a-1), R$^4$ is trifluoromethylthio, R$^5$ is hydrogen, Z is carbon, and R$^6$ is hydrogen;
or a pharmaceutically acceptable salt, solvate or polymorph thereof.

A first group of compounds of formula (I) are those compounds of formula (I) wherein radical A is (a-1).

A second group of compounds of formula (I) are those compounds of formula (I) wherein radical A is (a-2).

In an alternative representation, the present invention relates to a compound having formula (I),

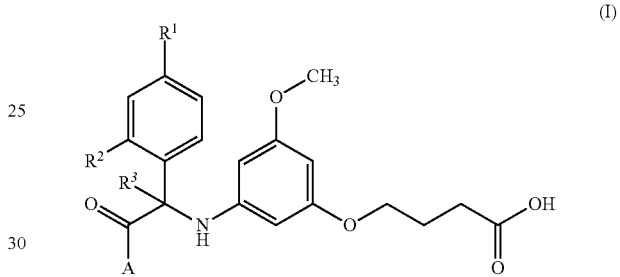

(I)

wherein
A is

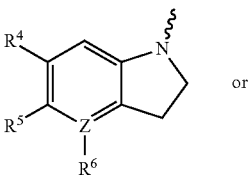

(a-1)

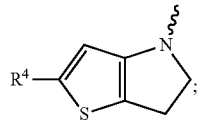

(a-2)

wherein the compound is selected from the group consisting of:

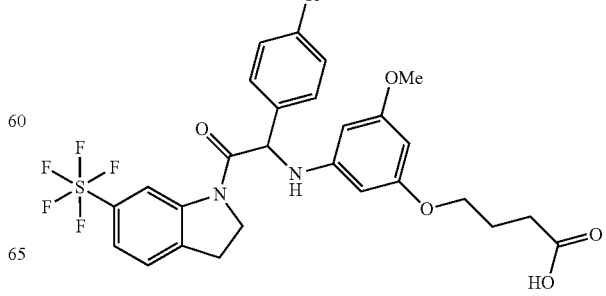

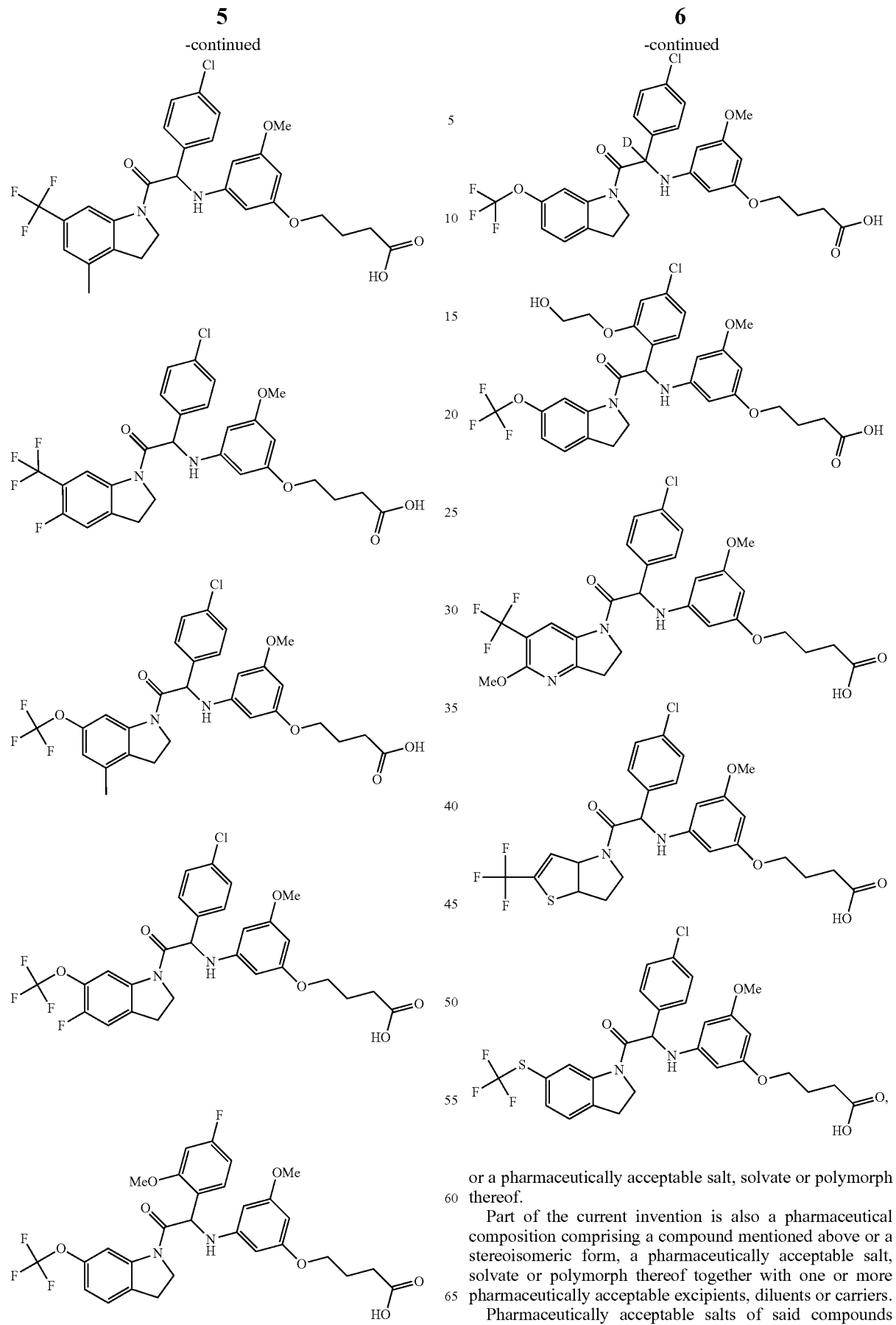

or a pharmaceutically acceptable salt, solvate or polymorph thereof.

Part of the current invention is also a pharmaceutical composition comprising a compound mentioned above or a stereoisomeric form, a pharmaceutically acceptable salt, solvate or polymorph thereof together with one or more pharmaceutically acceptable excipients, diluents or carriers.

Pharmaceutically acceptable salts of said compounds include the acid addition and base salts thereof. Suitable acid addition salts are formed from acids which form non-toxic salts. Suitable base salts are formed from bases which form non-toxic salts.

The pharmaceutically acceptable acid salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-amino-salicylic, pamoic acid and the like acids.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of the invention used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the terms "compound of formula (I)" and "intermediates of synthesis of formula (I)" are meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images.

The term "stereoisomers" also includes any rotamers, also called conformational isomers, the compounds of formula (I) may form.

Therefore, the invention includes enantiomers, diastereomers, racemates, E isomers, Z isomers, cis isomers, trans isomers, rotamers, and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (R), this means that the compound is substantially free of the (S) isomer.

Some of the compounds according to formula (I) may also exist in their tautomeric form. Such forms in so far as they may exist, although not explicitly indicated in the above formula (I) are intended to be included within the scope of the present invention.

The compounds of formula (I) of the present invention all have at least one asymmetric carbon atom as indicated in the figure below by the carbon atom labelled with *:

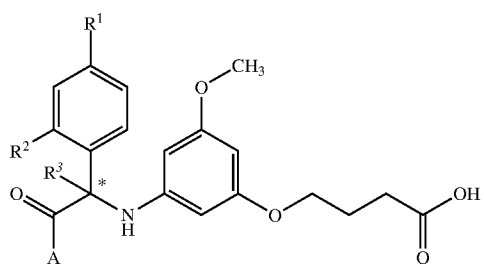

Due to the presence of said chiral center, a "compound of formula (I)" can be the (R)-enantiomer, the (S)-enantiomer, the racemic form, or any possible combination of the two individual enantiomers in any ratio. When the absolute (R)- or (S)-configuration of an enantiomer is not known, this enantiomer can also be identified by indicating whether the enantiomer is dextrorotatory (+)- or levorotatory (−)-after measuring the specific optical rotation of said particular enantiomer.

In an aspect the present invention relates to a first group of compound of formula (I) wherein the compounds of formula (I) have the (+) specific rotation.

In a further aspect the present invention relates to a second ground of compounds of formula (I) wherein the compounds of formula (I) have the (−) specific rotation.

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M−H]^−$ (deprotonated molecule). In case the compound was not directly ionizable the type of adduct is specified (i.e. $[M+NH_4]^+$, $[M+HCOO]^−$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LC/MS Method codes (Flow expressed in mL/min; column temperature (T) in ° C.; Run time in minutes).

| Method code | Instrument | Column | Mobile phase | Gradient | Flow / Col T | Run time (min) |
|---|---|---|---|---|---|---|
| LC-A | Waters: Acquity ® UPLC ®- | Waters: BEH ® C18 (1.7 µm, 2.1 × 100 mm) | A: 95% CH$_3$COONH$_4$ 7 mM/5% | 84.2% A for 0.49 min, to 10.5% A in 2.18 min, held for 1.94 min, back | 0.343 mL/min / 40° C. | 6.2 |
|  | DAD- Quattro Micro ™ |  | CH$_3$CN, B: CH$_3$CN | to 84.2% A in 0.73 min, held for 0.73 min. |  |  |
| LC-B | Waters: Acquity ® H-Class - | Waters: BEH ® C18 (1.7 µm, 2.1 × 100 mm) | A: 95% CH$_3$COONH$_4$ 7 mM/5% | 84.2% A/15.8% B to 10.5% A in 2.18 min, held for 1.96 min, back | 0.343 mL/min / 40° C. | 6.1 |
|  | DAD and SQD2TM |  | CH$_3$CN, B: CH$_3$CN | to 84.2% A/15.8% B in 0.73 min, held for 0.49 min. |  |  |

-continued

| Method code | Instrument | Column | Mobile phase | Gradient | Flow / Col T | Run time (min) |
|---|---|---|---|---|---|---|
| LC-C | Waters: Acquity® UPLC® - DAD-SQD | Waters: BEH C18 (1.7 μm, 2.1 × 50 mm) | A: 10 mM CH$_3$COONH$_4$ in 95% H$_2$O + 5% CH$_3$CN B: CH$_3$CN | From 95% A to 5% A in 1.3 min, held for 0.7 min. | 0.8 mL/min / 55° C. | 2 |
| LC-D | Waters: Acquity® UPLC® - DAD-SQD | Waters: HSS T3 (1.8 μm, 2.1 × 100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.7 mL/min / 55° C. | 3.5 |

SFC/MS Methods

The SFC measurement was performed using an Analytical Supercritical fluid chromatography (SFC) system composed by a binary pump for delivering carbon dioxide (CO2) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW).

Data acquisition was performed with appropriate software. Analytical SFC/MS Methods (Flow expressed in mL/min; column temperature (T) in ° C.; Run time in minutes, Backpressure (BPR) in bars.

| Method code | column | mobile phase | gradient | Flow / Col T | Run time / BPR |
|---|---|---|---|---|---|
| SFC-A | Daicel Chiralpak® AS3 column (3.0 μm, 150 × 4.6 mm) | A:CO$_2$ B: EtOH (+0.2% iPrNH$_2$ + 3% H$_2$O) | 10%-50% B in 6 min, hold 3.5 min | 2.5 / 40 | 9.5 / 110 |
| SFC-B | Daicel Chiralpak® OD3 column (3.0 μm, 150 × 4.6 mm) | A:CO$_2$ B: EtOH (+0.2% IPrNH$_2$) | 10%-50% B in 6 min, hold 3.5 min | 2.5 / 40 | 9.5 / 110 |
| SFC-C | Daicel Chiralpak® AS3 column (3.0 μm, 150 × 4.6 mm) | A:CO$_2$ B: EtOH (+0.2% IPrNH$_2$) | 10%-50% B in 6 min, hold 3.5 min | 2.5 / 40 | 9.5 / 110 |
| SFC-D | Daicel Chiralcel® OD-3 column (3 μm, 100 × 4.6 mm) | A:CO$_2$ B: IPrOH (+0.3% PrNH$_2$) | 40% B hold 3 min | 3.5 / 35 | 3 / 105 |
| SFC-E | Whelk ®-O-(R,R) column (5.0 μm, 250 × 4.6 mm) | A:CO$_2$ B: EtOH (+0.2% iPrNH$_2$) | 10%-50% B in 6 min, hold 3.5 min | 2.5 / 40 | 9.5 / 110 |
| SFC-F | Daicel Chiralpak® ID3 column (3.0 μm, 150 × 4.6 mm) | A:CO$_2$ B: EtOH (+0.2% IPrNH$_2$) | 10%-50% B in 6 min, hold 3.5 min | 2.5 / 40 | 9.5 / 110 |
| SFC-G | Regis Whelk O1, S,S column (3 μm, 100 × 4.6 mm) | A:CO$_2$ B: MeOH | 40% B hold 3 min, | 3.5 / 35 | 3 / 103 |

-continued

| Method code | column | mobile phase | gradient | Flow / Col T | Run time / BPR |
|---|---|---|---|---|---|
| SFC-H | Daicel Chiralcel ® OD-3 column (3 μm, 100 × 4.6 mm) | A:$CO_2$ B: MeOH | 40% B hold 3 min, | 3.5 / 35 | 3 / 103 |
| SFC-I | Daicel Chiralcel ® OD-3 column (3 μm, 100 × 4.6 mm) | A:$CO_2$ B: MeOH | 30% B hold 3 min, | 3.5 / 35 | 3 / 103 |

Melting Points

Values are either peak values or melt ranges, and are obtained with experimental uncertainties that are commonly associated with this analytical method.
DSC823e (Indicated as DSC)

For a number of compounds, melting points were determined with a DSC823e (Mettler-Toledo). Melting points were measured with a temperature gradient of 10° C./minute. Maximum temperature was 300° C.
Optical Rotations:

Optical rotations were measured on a Perkin-Elmer 341 polarimeter with a sodium lamp and reported as follows: [α]° (λ, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Abbreviations Used in Experimental Part

| | | | |
|---|---|---|---|
| $(M + H)^+$ $MH^+$ | protonated molecular ion | $iPrNH_2$ | isopropylamine |
| aq. | aqueous | iPrOH | 2-propanol |
| Boc | tert-butyloxycarbonyl | $K_2CO_3$ | potassium carbonate |
| $Boc_2O$ | di-tert-butyl dicarbonate | $KNO_3$ | potassium nitrate |
| br | broad | $LiAlH_4$ | lithium aluminium hydride |
| $CH_3CN$ | acetonitrile | m/z | mass-to-charge ratio |
| $CHCl_3$ | chloroform | Me | methyl |
| $CH_2Cl_2$ | dichloromethane | MeOH | methanol |
| $CH_3OH$ | methanol | $MgSO_4$ | magnesium sulfate |
| $CO_2$ | carbon dioxide | min | minute(s) |
| $CsCO_3$ | cesium carbonate | MTBE | methyl-tert-butylether |
| d | doublet | $N_2$ | nitrogen |
| DCM | dichloromethane | $Na_2CO_3$ | sodium carbonate |
| DIEA | diisopropylethylamine | $Na_2SO_4$ | sodium sulfate |
| DIPE | diisopropyl ether | $NaBH_4$ | sodium borohydride |
| DMA | dimethylacetamide | NaCl | sodium chloride |
| DMAP | 4-dimethylaminopyridine | $NaHCO_3$ | sodium bicarbonate |
| DME | 1,2-dimethoxyethane | NaOH | sodium hydroxide |
| DMF | dimethylformamide | $NH_4Cl$ | ammonium chloride |
| DMSO | dimethyl sulfoxide | $NH_4HCO_3$ | ammonium bicarbonate |
| EDCI | 1-ethyl-3-(3-dimethylamino-propyl)carbodiimide | NMP | N-methylpyrrolidon |
| eq. | equivalent | q | quartet |
| $Et_2O$ | diethyl ether | rt or RT | room temperature |
| $Et_3N$ | triethylamine | SEMCl | 2-(trimethylsilyl)ethoxymethyl chloride |
| EtOAc | ethyl acetate | s | singlet |
| EtOH | ethanol | t | triplet |
| $H_2$ | hydrogen | tBuOK | potassium tert-butanolaat |
| $HNO_3$ | nitric acid | TEA | triethylamine |
| $H_2O$ | water | TFA | trifluoroacetic acid |
| $H_2SO_4$ | sulfuric acid | THF | tetrahydrofuran |
| HATU | O-(7-aza-1H-benzotriazol-1-yl)-N,N,N',N'-tetramethyl-uronium hexafluorophosphate-CAS [148893-10-1] | 2-Me-THF | 2-methyltetrahydrofuran |
| HCl | hydrochloric acid | TMSCl | trimethylsilyl chloride |
| HPLC | high performance liquid chromatography | $TMSCF_3$ | trifluoromethyltrimethylsilane |

Example 1: synthesis of 4-(3-((1-(4-chlorophenyl)-2-oxo-2-(6-(pentafluoro-λ⁶-sulfanyl)indolin-1-yl)ethyl)amino)-5-methoxyphenoxy)butanoic Acid (Compound 1) and Chiral Separation into Enantiomers 1A and 1B
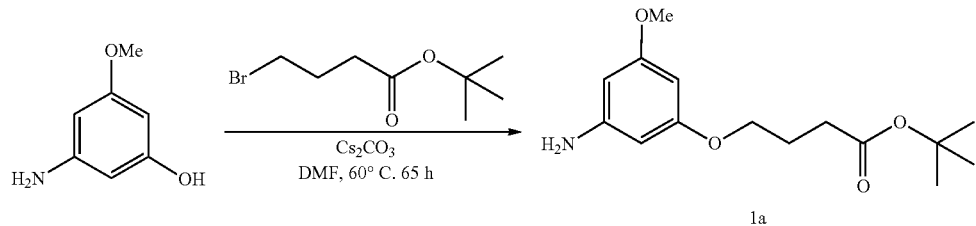
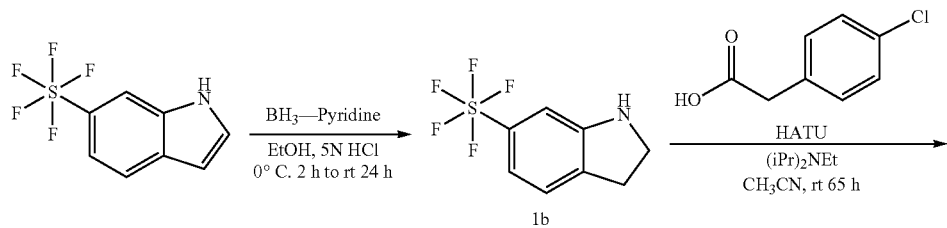
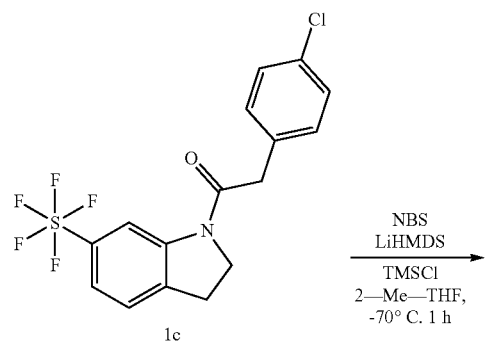
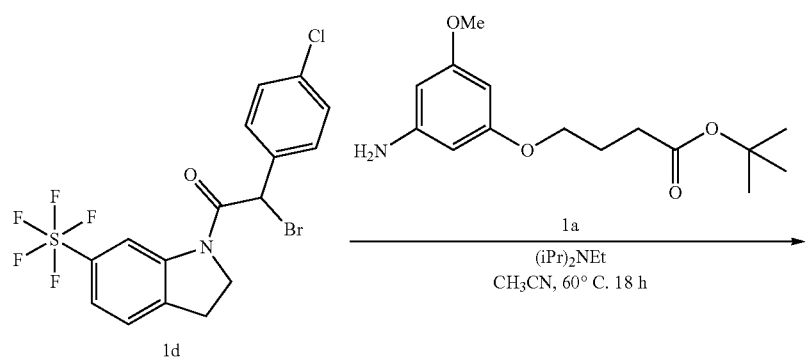

-continued

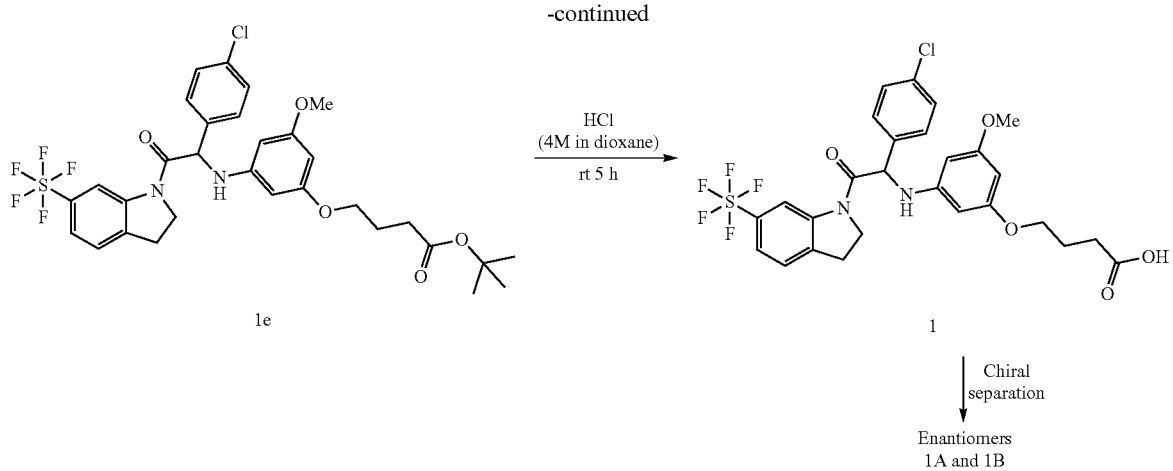

Synthesis of Intermediate 1a

To a mechanically stirred solution of tert-butyl 4-bromobutanoate [CAS 110661-91-1] (42.3 g, 0.19 mol) in DMF (600 mL) was added in portions a solid mixture of 3-amino-5-methoxyphenol [CAS 162155-27-3] (26.4 g, 0.19 mol) and $Cs_2CO_3$ (123.6 g, 0.379 mol). The reaction was stirred at 60° C. for 65 h, and allowed to reach room temperature. The mixture was poured out into $H_2O$ (2.5 L). The product was extracted with $Et_2O$ (2 times). The combined organic layers were washed with brine, dried over $MgSO_4$ and filtered. The solvent was evaporated under reduced pressure, and co-evaporated with toluene. The residue was purified via Normal Phase HPLC (Stationary phase: silica gel 60A 25-40 µm (Merck), mobile phase: gradient from 20% EtOAc, 80% heptane to 60% EtOAc, 40% heptane) yielding tert-butyl 4-(3-amino-5-methoxyphenoxy)butanoate 1a (27 g).

Synthesis of Intermediate 1b

At 0° C., $BH_3$-Pyridine (1.46 mL, 14.5 mmol) was added slowly to a solution of 6-(pentafluoro-$\lambda^6$-sulfanyl)-1H-indole [CAS 1379811-84-3] (1.0 g, 4.11 mmol) in EtOH (8.5 mL). 5N HCl (7 mL) was slowly added. The mixture was stirred at 0° C. for 2 h and allowed to gradually warm to room temperature while stirring overnight. After cooling to 0° C. (ice-bath), 50% NaOH (2 mL) was added dropwise and stirring was continued for 15 min. Water (50 mL) was added and the product was extracted with $Et_2O$/EtOAc 2/1. The organic layer was separated, dried over $MgSO_4$, filtered and the solvent was evaporated under reduced pressure. The residue was purified by flash chromatography on silica gel (25 g) using a gradient of heptane/$CH_2Cl_2$ 100/0 to 0/100. The product fractions were combined and evaporated under reduced pressure. The residue was dried under vacuum at 45° C. to give 6-(pentafluoro-$\lambda^6$-sulfanyl)indoline 1b (328 mg).

Synthesis of Intermediate 1c

A mixture of give 6-(pentafluoro-$I^6$-sulfanyl)indoline 1b (328 mg, 1.34 mmol), 2-(4-chlorophenyl)acetic acid [CAS 1878-66-6] (228 mg, 1.34 mmol), HATU (778 mg, 2.0 mmol) and diisopropylethylamine (663 µL, 4.0 mmol) in $CH_3CN$ (15 mL) was stirred at room temperature for 65 h. The solvent was evaporated under reduced pressure. The residue was dissolved in 2-Me-THF (50 mL) and washed with 1N HCl (25 mL) and brine. The organic layer was separated, dried over $MgSO_4$, filtered, and the solvent was evaporated under reduced pressure. The residue was purified by flash chromatography on silica gel (12 g) using a gradient of heptane/EtOAc 100/0 to 0/100. The desired fractions were combined and evaporated under reduced pressure. The product was crystallized from $CH_2Cl_2$/EtOAc, filtered off, washed (3×) with EtOAc, and dried under vacuum at 45° C. to provide 2-(4-chlorophenyl)-1-(6-(pentafluoro-$\lambda^6$-sulfanyl)indolin-1-yl)-ethanone 1c (209 mg). The filtrate was evaporated under reduced pressure. The residue was stirred up in $Et_2O$ (2 mL), filtered off, washed (3×) with $Et_2O$, and dried at under vacuum at 45° C. to provide a second crop of intermediate 1c (155 mg).

Synthesis of Intermediate 1d

At −70° C., under a $N_2$ flow, LiHMDS 1M in THF (1.78 mL, 1.78 mmol) was added dropwise to a mixture of 2-(4-chlorophenyl)-1-(6-(pentafluoro-$\lambda^6$-sulfanyl)indolin-1-yl)ethanone 1c (354 mg, 0.89 mmol) in 2-Me-THF (35 mL) and the mixture was kept at −70° C. for 30 min. TMSCl (182 µL, 1.42 mmol) was added dropwise. The mixture was stirred for 30 min at −70° C. and a solution of N-bromosuccinimide (198 mg, 1.11 mmol) in a solvent mixture of THF (1.5 mL) and 2-Me-THF (5 mL) was added dropwise. After stirring for 1 h at −78° C., the reaction was quenched with a saturated aqueous solution of $NH_4Cl$ (50 mL). The cooling bath was removed and the reaction mixture was stirred for 50 min. Water (10 mL) was added and the organic layer was separated, dried over $MgSO_4$, filtered and the solvent was evaporated under reduced pressure to give 2-bromo-2-(4-chlorophenyl)-1-(6-(pentafluoro-$\lambda^6$-sulfanyl) indolin-1-yl)ethanone 1d (424 mg), which was used as such in the next step.

Synthesis of Compound 1 and Chiral Separation into Enantiomers 1A and 1B

A mixture of 2-bromo-2-(4-chlorophenyl)-1-(6-(pentafluoro-$\lambda^6$-sulfanyl)indolin-1-yl)ethanone 1d (424 mg, 0.89 mmol), tert-butyl 4-(3-amino-5-methoxyphenoxy)butanoate 1a (260 mg, 0.92 mmol) and diisopropylethylamine (306 µL, 1.78 mmol) in $CH_3CN$ (30 mL) was stirred at 60° C. for 18 h. The reaction mixture was allowed to reach room temperature, and poured out into stirring water (150 mL). The product was extracted (2×) with Et$_2$O. The combined organic layers were washed with brine, dried over MgSO$_4$, filtered, and the solvent was evaporated under reduced pressure. The residue was purified by flash chromatography on silica gel (40 g) using a gradient of heptane/EtOAc/EtOH 100/0/0 to 40/45/15). The desired fractions were combined, evaporated under reduced pressure, and co-evaporated with dioxane.

The residue (602 mg, containing 58% of intermediate 1e) was mixed with 4M HCl in dioxane (4 mL) and the mixture was stirred at room temperature for 5 h. The solids were filtered off, washed with dioxane (3×) and Et$_2$O (2×), and dried under vacuum at 45° C. to provide crude 4-(3-((1-(4-chlorophenyl)-2-oxo-2-(6-(pentafluoro-$\lambda^6$-sulfanyl)indolin-1-yl)ethyl)amino)-5-methoxyphenoxy)butanoic acid (Compound 1, 309 mg). An analytical sample (60 mg) of racemic Compound 1 was further purified via preparative HPLC (Stationary phase: RP XBridge® Prep C18 OBD—10 μm, 30×150 mm, mobile phase: 0.25% NH$_4$HCO$_3$ solution in water, CH$_3$CN). The pure fractions were combined and the organic volatiles were evaporated under reduced pressure. The remaining aqueous solution was co-evaporated under reduced pressure with o-xylene. The residue was dissolved in a solvent mixture of CH$_3$CN and water, evaporated under reduced pressure and co-evaporated with dioxane. The residue was lyophilized from a solvent mixture of CH$_3$CN (2 mL) and water (0.8 mL) to provide pure 4-(3-((1-(4-chlorophenyl)-2-oxo-2-(6-(pentafluoro-$\lambda^6$-sulfanyl)indolin-1-yl)ethyl)amino)-5-methoxyphenoxy)butanoic acid (Compound 1, 40 mg) as a powder.

The enantiomers of Compound 1 (249 mg) were separated via preparative chiral SFC (Stationary phase: Chiralpak® Diacel AD 20×250 mm, mobile phase: CO$_2$, EtOH+0.4% iPrNH$_2$). The product fractions of the first eluted enantiomer were combined, evaporated under reduced pressure and co-evaporated with MeOH. The residue was stirred up in water (3.5 mL) and MeOH (1 mL), the solids were filtered off, washed (3×) with water/MeOH 4/1, and dried under vacuum at 45° C. to provide Enantiomer 1A (41 mg). The product fractions of the second eluted enantiomer were combined, evaporated under reduced pressure and co-evaporated with MeOH. The residue was stirred up in water (3 mL) and MeOH (0.6 mL), the solids were filtered off, washed (3×) with water/MeOH 4/1, and dried under vacuum at 45° C. to provide Enantiomer 1B (48 mg).

Compound 1:
$^1$H NMR (400 MHz, DMSO-d$_6$) δ ppm 1.86 (quin, J=6.8 Hz, 2H) 2.33 (t, J=7.3 Hz, 2H) 3.12-3.25 (m, 2H) 3.61 (s, 3H) 3.84 (t, J=6.5 Hz, 2H) 3.99-4.13 (m, 1H) 4.47-4.59 (m, 1H) 5.57 (d, J=8.6 Hz, 1H) 5.76 (t, J=2.1 Hz, 1H) 5.91-5.96 (m, 2H) 6.45 (d, J=8.6 Hz, 1H) 7.39-7.50 (m, 3H) 7.51-7.62 (m, 3H) 8.58 (d, J=2.0 Hz, 1H) 12.12 (br s, 1H)

LC/MS (method LC-C): Rt 1.09 min, MH$^+$ 621

Enantiomer 1A:
$^1$H NMR (360 MHz, DMSO-d$_6$) δ ppm 1.85 (quin, J=6.8 Hz, 2H) 2.26 (br t, J=6.8 Hz, 2H) 3.15-3.25 (m, 2H) 3.61 (s, 3H) 3.84 (br t, J=6.4 Hz, 2H) 4.02-4.12 (m, 1H) 4.48-4.60 (m, 1H) 5.59 (d, J=8.8 Hz, 1H) 5.76 (t, J=2.0 Hz, 1H) 5.93 (t, J=2.0 Hz, 1H) 5.96 (t, J=2.0 Hz, 1H) 6.47 (d, J=8.4 Hz, 1H) 7.42-7.47 (m, 3H) 7.53-7.59 (m, 3H) 8.58 (d, J=2.2 Hz, 1H)

LC/MS (method LC-D): R$_t$ 1.99 min, MH$^+$ 621

$[\alpha]_D^{20}$: −44.6° (c 0.28, DMF)

Chiral SFC (method SFC-A): R$_t$ 3.54 min, MH$^+$ 621 chiral purity 97.9%.

Enantiomer 1B:
$^1$H NMR (360 MHz, DMSO-d$_6$) δ ppm 1.86 (quin, J=6.8 Hz, 2H) 2.33 (t, J=7.3 Hz, 2H) 3.14-3.29 (m, 2H) 3.61 (s, 3H) 3.84 (t, J=6.4 Hz, 2H) 4.01-4.11 (m, 1H) 4.48-4.58 (m, 1H) 5.58 (d, J=9.1 Hz, 1H) 5.76 (t, J=2.0 Hz, 1H) 5.93 (t, J=1.8 Hz, 1H) 5.94-5.96 (m, 1H) 6.48 (d, J=9.1 Hz, 1H) 7.41-7.48 (m, 3H) 7.52-7.61 (m, 3H) 8.58 (d, J=2.2 Hz, 1H) 12.13 (br s, 1H) LC/MS (method LC-D): R$_t$ 1.98 min, MH$^+$ 621

$[\alpha]_D^{20}$: +46.0° (c 0.265, DMF)

Chiral SFC (method SFC-A): R$_t$ 3.82 min, MH$^+$ 621 chiral purity 99.0%.

Example 2: synthesis of 4-(3-((1-(4-chlorophenyl)-2-(4-methyl-6-(trifluoromethyl)indolin-1-yl)-2-oxo-ethyl)amino)-5-methoxyphenoxy)butanoic acid (Compound 2) and Chiral Separation into Enantiomers 2A and 2B

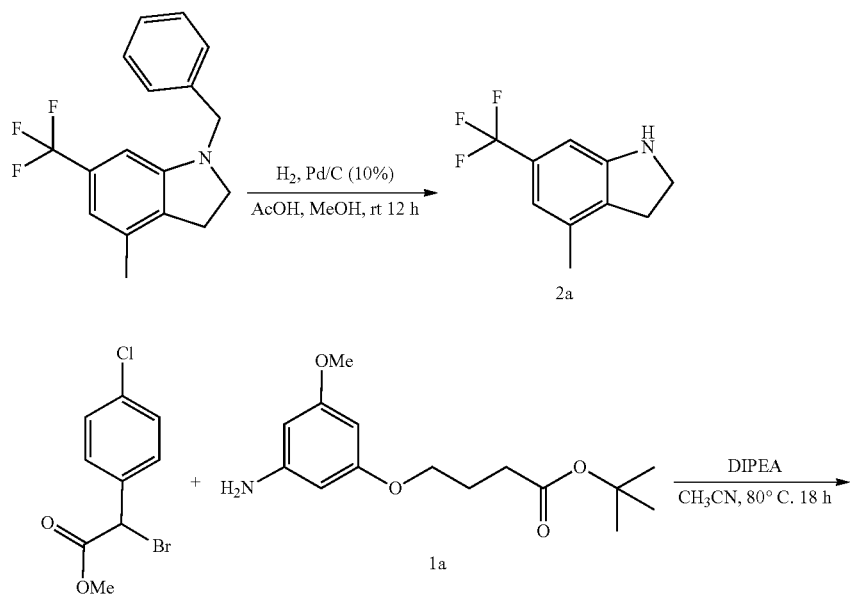

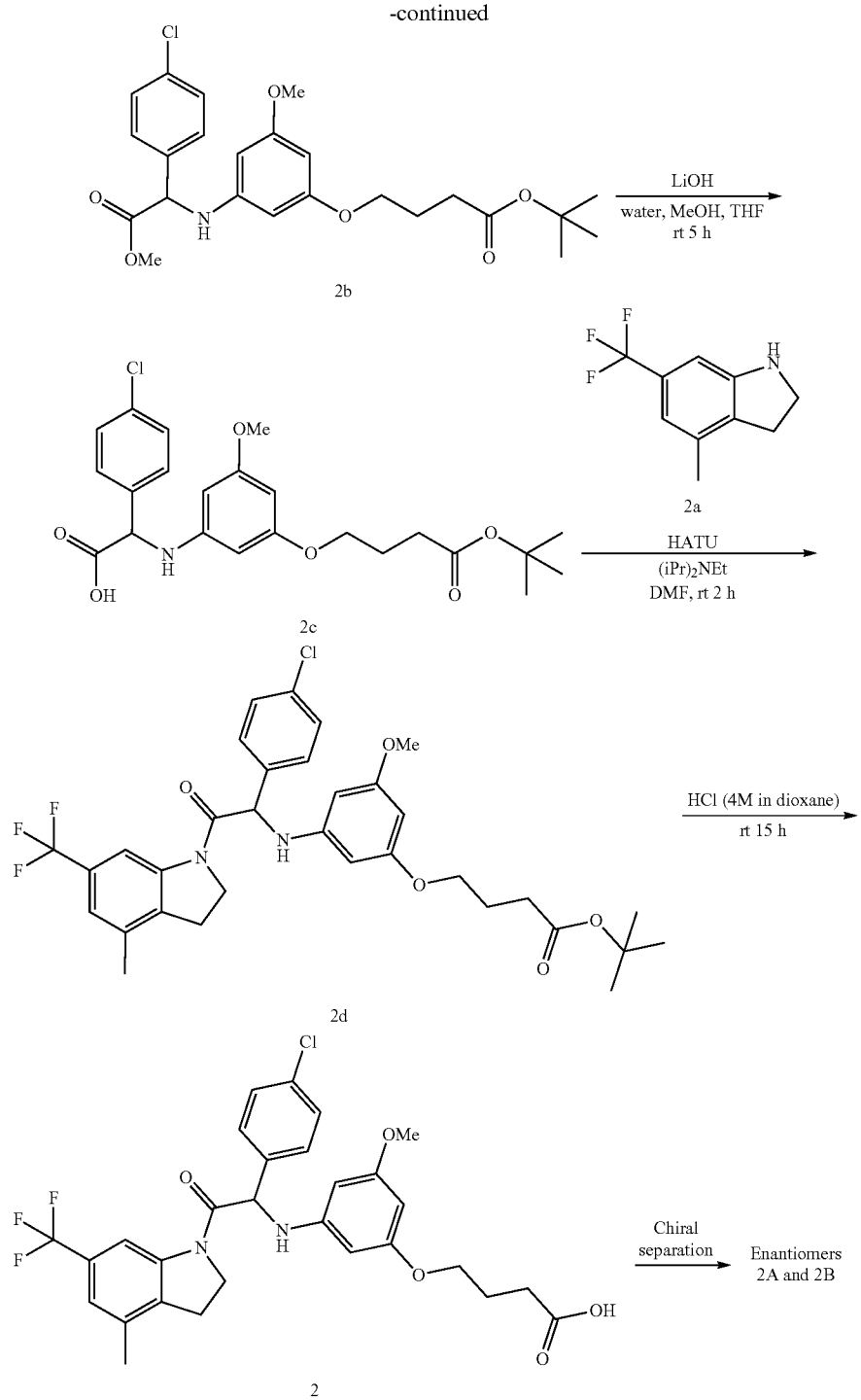

Synthesis of Intermediate 2a

Pd/C (10%) (1.18 g) was added to a solution of 1-benzyl-4-methyl-6-(trifluoromethyl)indoline [CAS 1156512-79-6] (11.8 g, 40.5 mmol) in AcOH (11.8 mL) and MeOH (118 mL). The reaction was stirred at room temperature for 12 h under $H_2$ atmosphere. The mixture was filtered through a pad of Celite® and concentrated under reduced pressure. The residue was taken up with $CH_2Cl_2$, washed with water, brine, dried over $MgSO_4$, filtered and concentrated under reduced pressure. The residue was purified by flash chromatography on silica gel (heptane/EtOAc 9/1). The pure fractions were combined and the solvent was evaporated to dryness to give 8.2 g of 4-methyl-6-(trifluoromethyl)indoline 2a.

Synthesis of Intermediate 2b tert-butyl 4-(3-amino-5-methoxyphenoxy)butanoate 1a (2.94 g, 10.5 mmol) was added to solution of methyl 2-bromo-2-(4-chlorophenyl)acetate [CAS 24091-92-7] (2.51 g, 9.53 mmol) in $CH_3CN$ (200 mL). Diisopropylethylamine (2.46 mL, 14.3 mmol) was added and the reaction mixture was stirred at 80° C. overnight. The solvent was evaporated under reduced pressure. The residue was dissolved in $CH_2Cl_2$ and washed with 1N HCl. The organic layer was washed with water, dried over $MgSO_4$, filtered, and evaporated to dryness under reduced pressure. The residue was purified by column chromatography on silica gel (100 g) using a gradient of EtOAc:EtOH (3:1)/heptane 0/100 to 50/50. The product fractions were combined, and evaporated under reduced pressure and the residue was dried under vacuum at 50° C. to provide tert-butyl 4-(3-((1-(4-chlorophenyl)-2-methoxy-2-oxoethyl)amino)-5-methoxyphenoxy)butanoateas 2b (3.74 g) as a yellow oil.

Synthesis of Intermediate 2c

Lithium hydroxide (336 mg, 14.0 mmol) was added to a solution of tert-butyl 4-(3-((1-(4-chlorophenyl)-2-methoxy-2-oxoethyl)amino)-5-methoxyphenoxy)butanoateas 2b (3.74 g, 7.02 mmol) in a solvent mixture of water (25 mL), MeOH (25 mL) and THF (75 mL) and the reaction mixture was stirred at room temperature for 5 h. Saturated aqueous $NH_4Cl$ (50 mL) was added and the organic volatiles were evaporated under reduced pressure. The residual aqueous solution was acidified with 1N HCl to pH 2 and extracted twice with EtOAc. The combined organic layers were dried over $MgSO_4$, filtered, and evaporated under reduced pressure. The residue was dried under vacuum at 50° C. to give 2-((3-(4-(tert-butoxy)-4-oxobutoxy)-5-methoxyphenyl)amino)-2-(4-chlorophenyl)acetic acid 2c (3.22 g) as a thick brown oil.

Synthesis of Intermediate 2d

N,N-Diisopropylethylamine (1.58 mL, 9.57 mmol) was added to a solution of 2-((3-(4-(tert-butoxy)-4-oxobutoxy)-5-methoxyphenyl)amino)-2-(4-chlorophenyl)acetic acid 2c (1.44 g, 3.19) and 4-methyl-6-(trifluoromethyl)indoline 2a (953 mg, 3.51 mmol) in dry DMF (30 mL). HATU (1.82 g, 4.78 mmol) was added and the reaction mixture was stirred at room temperature for 2 h. The reaction mixture was poured out into water (400 mL) and the white suspension was extracted with EtOAc. The aqueous layer was saturated by the addition of NaCl and extracted again with EtOAc. The combined organic layers were washed with brine, water, dried over $MgSO_4$ and evaporated under reduced pressure. The residue was purified by column chromatography on silica gel (100 g) using a gradient of EtOAc:EtOH (3:1)/heptane 0/100 to 60/40. The product fractions were combined and evaporated under reduced pressure. The residue (1.41 g) was purified via preparative HPLC (Stationary phase: RP XBridge® Prep C18 OBD—10 μm, 50×150 mm, mobile phase: 0.25% $NH_4HCO_3$ solution in water, $CH_3CN$). The product fractions were combined and evaporated under reduced pressure to provide tert-butyl 4-(3-((1-(4-chlorophenyl)-2-(4-methyl-6-(trifluoromethyl)indolin-1-yl)-2-oxoethyl)amino)-5-methoxyphenoxy)butanoate 2d (808 mg) as a white solid.

Synthesis of Compound 2 and Chiral Separation into Enantiomers 2A and 2B

Tert-butyl 4-(3-((1-(4-chlorophenyl)-2-(4-methyl-6-(trifluoromethyl)indolin-1-yl)-2-oxoethyl)amino)-5-methoxyphenoxy)butanoate 2d (808 mg, 1.28 mmol) was mixed with 4M HCl in dioxane (9.6 mL) and the mixture was stirred at room temperature for 15 h. Nitrogen gas was bubbled through the reaction mixture for 30 min. The solvent was evaporated under reduced pressure to give 4-(3-((1-(4-chlorophenyl)-2-(4-methyl-6-(trifluoromethyl)indolin-1-yl)-2-oxoethyl)amino)-5-methoxyphenoxy)butanoic acid (Compound 2, 735 mg) as a light brown solid. The enantiomers of Compound 2 (735 mg) were separated via preparative chiral SFC (Stationary phase: Chiralcel® Diacel OD 20×250 mm, mobile phase: $CO_2$, EtOH+0.4% $iPrNH_2$). The product fractions were combined and evaporated under reduced pressure to give Enantiomer 2A as the first eluted product and Enantiomer 2B as the second eluted product. Both residues were mixed with EtOAc and water. The mixture was acidified to pH 1-2 with 1N HCl. The layers were separated and the aqueous layer was extracted twice with EtOAc. The combined organic layers were washed with water, dried over $MgSO_4$, filtered, and evaporated under reduced pressure. The residue was dried under vacuum at 50° C. to give Enantiomer 2A (216 mg) and Enantiomer 2B (184 mg), respectively.

Compound 2:

$^1$H NMR (360 MHz, DMSO-d$_6$) δ ppm 1.87 (br quin, J=6.9 Hz, 2H) 2.25 (s, 3H) 2.33 (br t, J=7.1 Hz, 2H) 3.07-3.20 (m, 2H) 3.62 (s, 3H) 3.84 (br t, J=6.4 Hz, 2H) 3.97-4.09 (m, 1H) 4.48-4.60 (m, 1H) 5.57 (br d, J=8.8 Hz, 1H) 5.76 (t, J=1.8 Hz, 1H) 5.90-5.99 (m, 2H) 6.43 (br d, J=8.8 Hz, 1H) 7.25 (s, 1H) 7.44 (d, J=8.4 Hz, 2H) 7.56 (br d, J=8.4 Hz, 2H) 8.22 (s, 1H) 12.15 (br s, 1H) LC/MS (method LC-C): Rt 1.14 min, MH$^+$ 577

Enantiomer 2A:

$^1$H NMR (360 MHz, DMSO-d$_6$) δ ppm 1.87 (quin, J=6.8 Hz, 2H) 2.25 (s, 3H) 2.34 (t, J=7.3 Hz, 2H) 3.05-3.23 (m, 2H) 3.62 (s, 3H) 3.85 (t, J=6.4 Hz, 2H) 4.03 (td, J=10.2, 7.3 Hz, 1H) 4.54 (td, J=10.2, 6.2 Hz, 1H) 5.57 (d, J=8.8 Hz, 1H) 5.76 (t, J=2.0 Hz, 1H) 5.91-5.99 (m, 2H) 6.42 (d, J=8.8 Hz, 1H) 7.24 (s, 1H) 7.44 (d, J=8.4 Hz, 2H) 7.56 (d, J=8.8 Hz, 2H) 8.22 (s, 1H) 12.17 (br s, 1H) LC/MS (method LC-C): $R_t$ 1.26 min, MH$^+$ 577

$[α]_D^{20}$: −39.0° (c 0.438, DMF)

Chiral SFC (method SFC-B): $R_t$ 5.11 min, MH$^+$ 577 chiral purity 100%.

Enantiomer 2B:

$^1$H NMR (360 MHz, DMSO-de) δ ppm 1.88 (quin, J=6.9 Hz, 2H) 2.25 (s, 3H) 2.34 (t, J=7.3 Hz, 2H) 3.06-3.24 (m, 2H) 3.62 (s, 3H) 3.85 (t, J=6.4 Hz, 2H) 3.97-4.11 (m, 1H) 4.55 (td, J=10.3, 6.8 Hz, 1H) 5.58 (d, J=8.4 Hz, 1H) 5.77 (t, J=2.0 Hz, 1H) 5.92-5.99 (m, 2H) 6.43 (d, J=8.8 Hz, 1H) 7.25 (s, 1H) 7.41-7.50 (m, 2H) 7.52-7.60 (m, 2H) 8.23 (s, 1H) 12.17 (br s, 1H)

LC/MS (method LC-C): $R_t$ 1.25 min, MH$^+$ 577

$[α]_D^{20}$: +47.1° (c 0.384, DMF)

Chiral SFC (method SFC-B): $R_t$ 8.00 min, MH$^+$ 577 chiral purity 99.6%.

Example 3: synthesis of 4-(3-((1-(4-chlorophenyl)-2-(5-fluoro-6-(trifluoromethyl)indolin-1-yl)-2-oxo-ethyl)amino)-5-methoxyphenoxy)butanoic Acid (Compound 3) and Chiral Separation into Enantiomers 3A and 3B
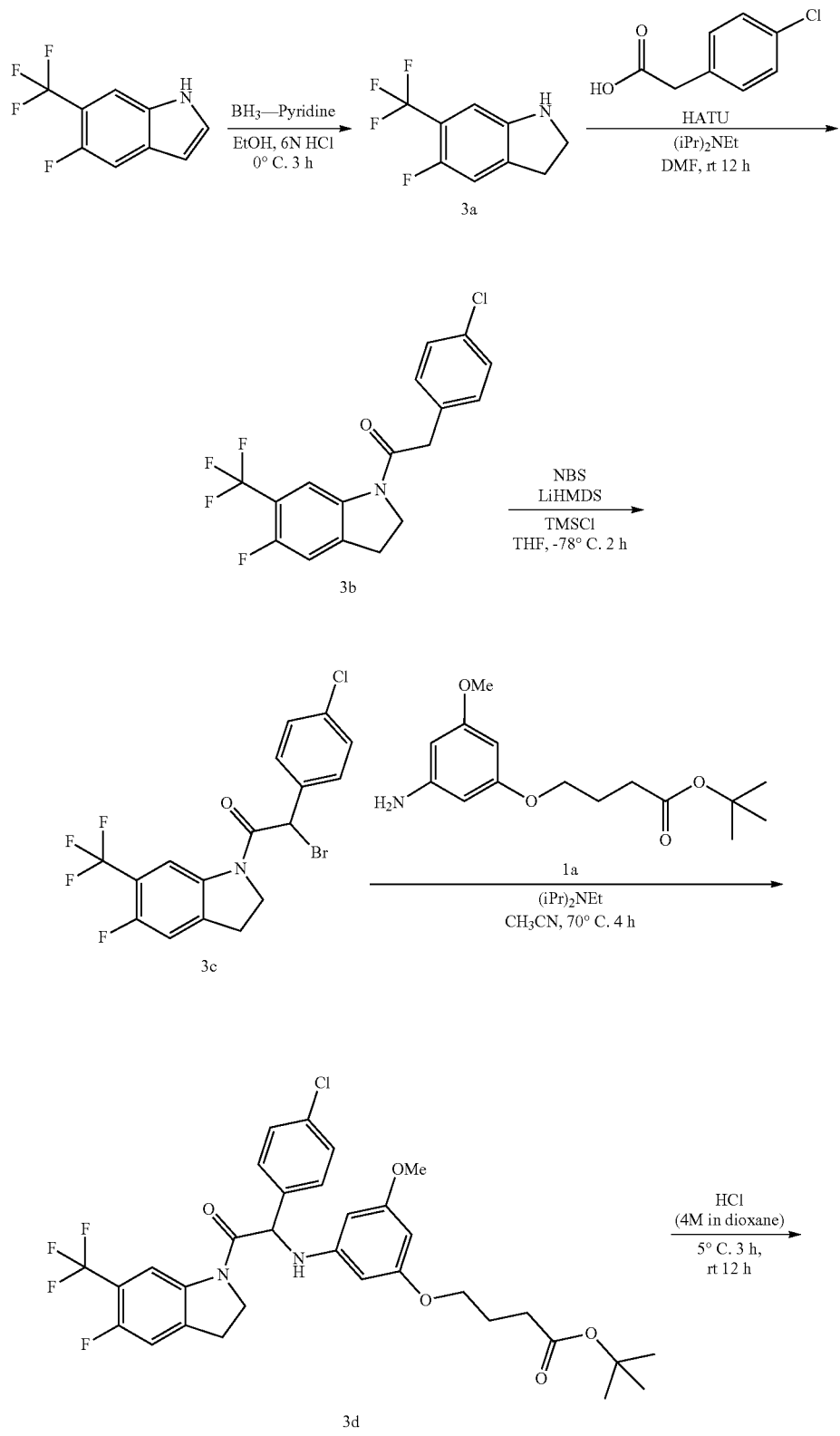

-continued

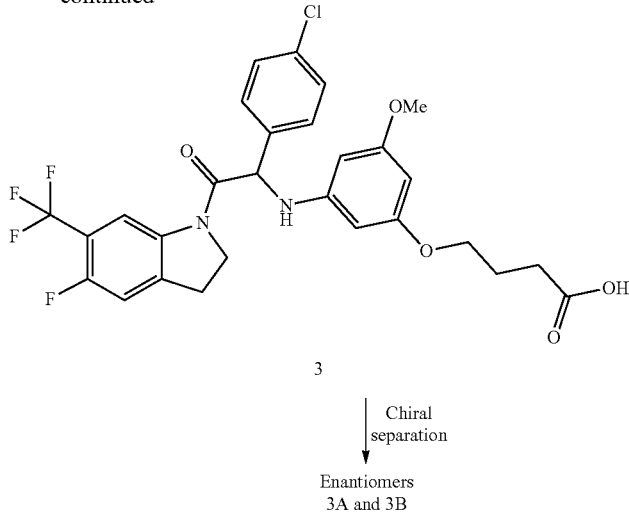

3

Chiral separation

Enantiomers 3A and 3B

Synthesis of Intermediate 3a

At 0° C., BH$_3$-Pyridine (10.45 mL, 103.4 mmol) was added slowly to a solution of 5-fluoro-6-(trifluoromethyl)-1H-indole [CAS 1493800-10-4] (7.0 g, 34.5 mmol) in EtOH (45 mL). 6N HCl (105 mL) was added dropwise while maintaining the temperature below 10° C. The mixture was stirred at 0° C. for 3 h. Water was added and the mixture was basified to pH 8.5 with a concentrated solution of NaOH (temperature below 20° C.). EtOAc was added. The organic layer was separated, washed with water, dried over MgSO$_4$, filtered and the solvent was evaporated under reduced pressure. Toluene was added and removed under reduced pressure (to eliminate traces of pyridine). The residue was purified by flash chromatography on silica gel (20-45 µm, 120 g, CH$_2$Cl$_2$/MeOH 98.5/1.5). The pure fractions were combined and the solvent was concentrated under reduced pressure to give 5-fluoro-6-(trifluoromethyl)indoline 3a (3.5 g).

Synthesis of Intermediate 3b

A mixture of 5-fluoro-6-(trifluoromethyl)indoline 3a (500 mg, 2.44 mmol), 2-(4-chlorophenyl)acetic acid [CAS 1878-66-6] (457 mg, 2.64 mmol), HATU (1.39 g, 3.66 mmol) and diisopropylethylamine (1.2 mL, 7.31 mmol) in DMF (10 mL) was stirred at room temperature for 12 h. The mixture was poured out into ice-water, the precipitate was filtered off and taken up with CH$_2$Cl$_2$. The organic layer was dried over MgSO$_4$ and concentrated under reduced pressure. The compound was crystallized from CH$_3$CN and dried to give 2-(4-chlorophenyl)-1-(5-fluoro-6-(trifluoromethyl)indolin-1-yl)ethanone 3b (854 mg).

Synthesis of Intermediate 3c

At −78° C., under a N$_2$ flow, LiHMDS 1M in THF (4.78 mL, 4.78 mmol) was added dropwise to a mixture of 2-(4-chlorophenyl)-1-(5-fluoro-6-(trifluoromethyl)indolin-1-yl)ethanone 3b (854 mg, 2.39 mmol) in THF (7 mL). TMSCl (485 µL, 3.82 mmol) was added dropwise. The mixture was stirred for 15 min at −78° C. and a solution of N-bromosuccinimide (510 mg, 2.87 mmol) in THF (7 mL) was added dropwise. After stirring for 2 h at −78° C., the reaction was quenched with a saturated aqueous solution of NH$_4$Cl. EtOAc was added and the organic layer was separated, dried over MgSO$_4$, filtered and the solvent was evaporated under reduced pressure. The residue was purified by flash chromatography on silica gel (15-40 µm, 40 g, CH$_2$Cl$_2$/heptane 50/50). The pure fractions were combined and the solvent was concentrated under reduced pressure to give 2-bromo-2-(4-chlorophenyl)-1-(5-fluoro-6-(trifluoromethyl)indolin-1-yl)ethanone 3c (820 mg).

Synthesis of Intermediate 3d

A mixture of 2-bromo-2-(4-chlorophenyl)-1-(5-fluoro-6-(trifluoromethyl)indolin-1-yl)ethanone 3c (820 mg, 1.88 mmol), tert-butyl 4-(3-amino-5-methoxyphenoxy)-butanoate 1a (528 mg, 1.88 mmol) and diisopropylethylamine (388 µL, 2.25 mmol) in CH$_3$CN (20 mL) was stirred at 70° C. for 4 h. The reaction mixture was concentrated under reduced pressure. The residue was taken up with EtOAc. The organic layer was washed twice with a 1N solution of HCl, water, dried over MgSO$_4$, filtered and the solvent was removed under reduced pressure. The residue was purified by flash chromatography on silica gel (15-40 µm, 40 g, CH$_2$Cl$_2$ 100%). The pure fractions were combined and the solvent was concentrated under reduced pressure to give tert-butyl 4-(3-((1-(4-chlorophenyl)-2-(5-fluoro-6-(trifluoromethyl) indolin-1-yl)-2-oxoethyl)amino)-5-methoxyphenoxy)-butanoate 3d (1.07 g).

Synthesis of Compound 3 and Chiral Separation into Enantiomers 3A and 3B

A solution of tert-butyl 4-(3-((1-(4-chlorophenyl)-2-(5-fluoro-6-(trifluoromethyl)indolin-1-yl)-2-oxoethyl)amino)-5-methoxyphenoxy)butanoate 3d (1.07 g, 1.68 mmol) in HCl (4M in dioxane) (20 mL) was stirred at 5° C. for 3 h and at room temperature for 12 h. The precipitate was filtered off, washed with diisopropyl ether and dried. The residue was purified via reverse phase chromatography (Stationary phase: YMC-actus Triart-C18 10 µm 30×150 mm, mobile phase: gradient from 65% NH$_4$HCO$_3$ 0.2%, 35% CH$_3$CN to 25% NH$_4$HCO$_3$ 0.2%, 75% CH$_3$CN) to provide Compound 3 (540 mg). An analytical sample (30 mg) was further purified via reverse phase chromatography (Stationary phase: YMC-actus Triart-C18 10 μm 30×150 mm, mobile phase: gradient from 65% NH$_4$HCO$_3$ 0.2 35% CH$_3$CN to 25% NH$_4$HCO$_3$ 0.2%, 75% CH$_3$CN) to give 4-(3-((1-(4-chlorophenyl)-2-(5-fluoro-6-(trifluoromethyl)indolin-1-yl)-2-oxoethyl)amino)-5-methoxyphenoxy)butanoic acid (Compound 3, 30 mg, 0.16 H$_2$O). The remaining amount of Compound 3 (510 mg) was used for chiral separation of the enantiomers via Preparative Chiral SFC (Stationary phase: Whelk O1 S,S 5 μm 250×30 mm, mobile phase: 60% CO$_2$, 40% MeOH). The first eluted enantiomer (250 mg) was further purified by flash chromatography on silica gel (20-45 μm, 24 g, CH$_2$Cl$_2$/MeOH 98/2). The pure fractions were combined and the solvent was concentrated under reduced pressure to give, after solidification in heptane/diisopropyl ether, Enantiomer 3A (170 mg). The second eluted enantiomer (249 mg) was solidified in heptane/diisopropyl ether to give Enantiomer 3B (182 mg).

Compound 3:
$^1$H NMR (500 MHz, DMSO-d$_6$) δ ppm 1.78-1.92 (m, 2H) 2.26 (br s, 2H) 3.15-3.31 (m, 2H) 3.61 (s, 3H) 3.84 (br s, 2H) 4.02 (br d, J=7.88 Hz, 1H) 4.54 (br d, J=5.99 Hz, 1H) 5.58 (br d, J=8.51 Hz, 1H) 5.76 (br s, 1H) 5.90-5.99 (m, 2H) 6.42 (br d, J=8.51 Hz, 1H) 7.44 (br d, J=7.88 Hz, 3H) 7.55 (br d, J=7.88 Hz, 2H) 8.38 (br d, J=6.31 Hz, 1H) 11.60-12.92 (m, 1H)
LC/MS (method LC-A): Rt 2.94 min, MH$^+$ 581
Melting point: 206° C.
Enantiomer 3A:
$^1$H NMR (500 MHz, DMSO-d$_6$) δ ppm 1.87 (quin, J=6.86 Hz, 2H) 2.29-2.39 (m, 2H) 3.18-3.30 (m, 2H) 3.62 (s, 3H) 3.85 (t, J=6.46 Hz, 2H) 4.03 (td, J=10.25, 7.25 Hz, 1H) 4.54 (td, J=10.17, 6.15 Hz, 1H) 5.58 (d, J=8.51 Hz, 1H) 5.76 (s, 1H) 5.95 (br d, J=11.35 Hz, 2H) 6.43 (d, J=8.83 Hz, 1H) 7.43-7.48 (m, 3H) 7.55 (d, J=8.51 Hz, 2H) 8.39 (d, J=6.31 Hz, 1H) 12.08-12.27 (m, 1H)
LC/MS (method LC-A): R$_t$ 2.95 min, MH$^+$ 581
[α]$_D^{20}$: −48.9° (c 0.315, DMF)
Chiral SFC (method SFC-G): R$_t$ 1.65 min, MH$^+$ 581 chiral purity 100%.

Enantiomer 3B:
$^1$H NMR (500 MHz, DMSO-d$_6$) δ ppm 1.87 (quin, J=6.54 Hz, 2H) 2.25-2.46 (m, 2H) 3.15-3.31 (m, 2H) 3.62 (s, 3H) 3.85 (br t, J=6.31 Hz, 2H) 3.98-4.07 (m, 1H) 4.50-4.59 (m, 1H) 5.58 (br d, J=8.83 Hz, 1H) 5.76 (s, 1H) 5.95 (br d, J=12.30 Hz, 2H) 6.43 (br d, J=8.83 Hz, 1H) 7.42-7.48 (m, 3H) 7.56 (br d, J=8.20 Hz, 2H) 8.39 (br d, J=6.31 Hz, 1H) 11.40-12.54 (m, 1H)
LC/MS (method LC-A): R$_t$ 2.94 min, MH$^+$ 581
[α]$_D^{20}$: +47.8° (c 0.27, DMF)
Chiral SFC (method SFC-G): R$_t$ 2.14 min, MH$^+$ 581 chiral purity 99.43%.

Example 4: synthesis of 4-(3-((1-(4-chlorophenyl)-2-(4-methyl-6-(trifluoromethoxy)indolin-1-yl)-2-oxoethyl)amino)-5-methoxyphenoxy)butanoic Acid (Compound 4) and Chiral Separation into Enantiomers 4A and 4B

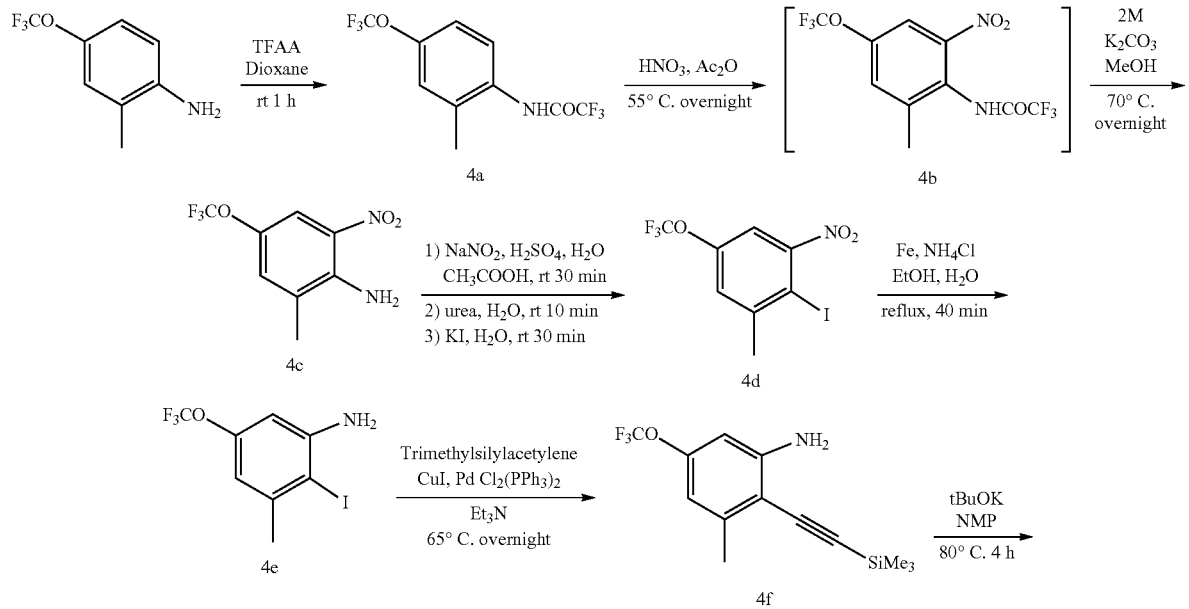

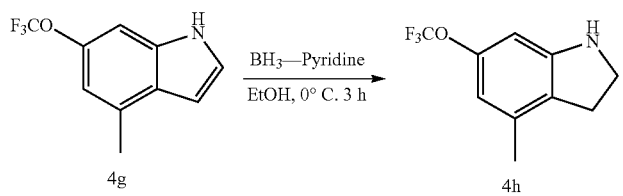

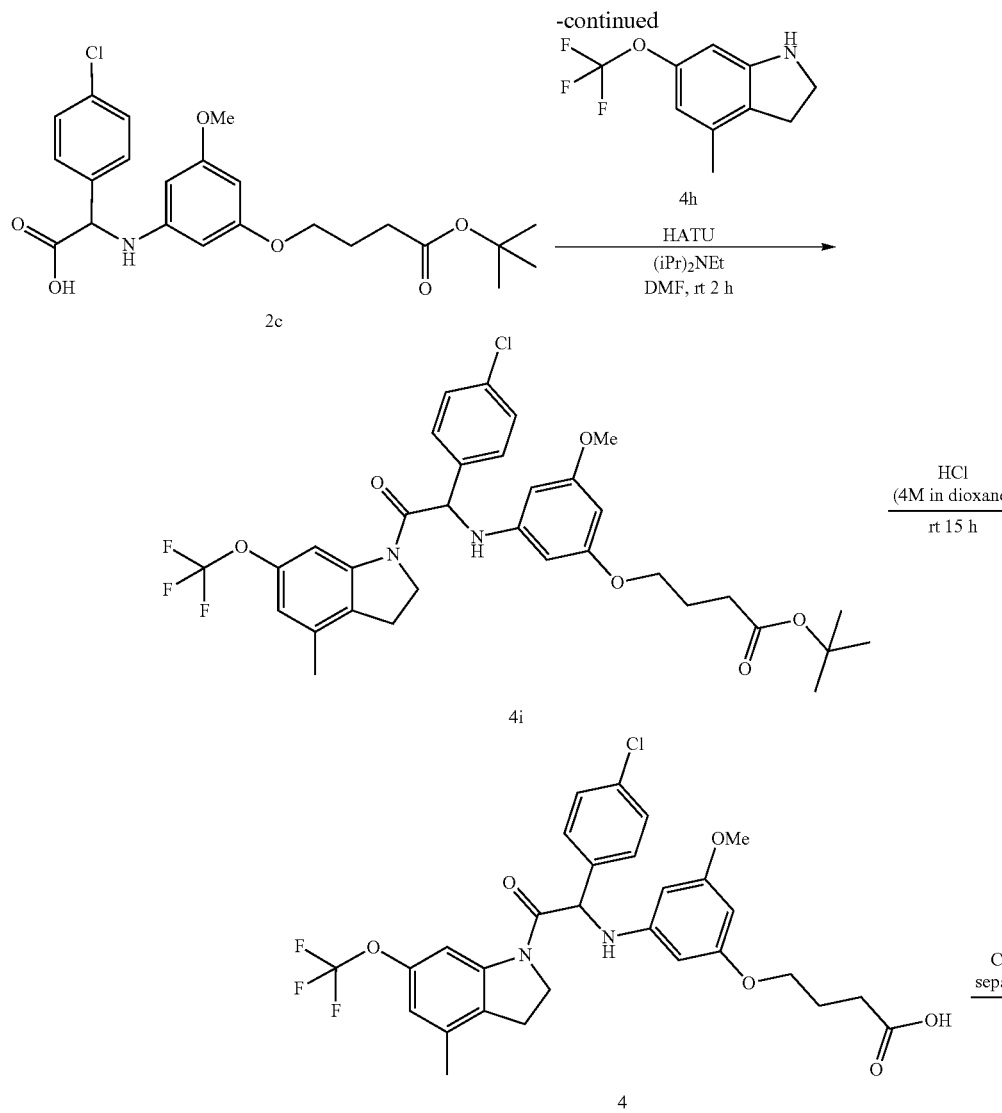

Synthesis of Intermediate 4a

To a solution of 2-methyl-4-(trifluoromethoxy)aniline [CAS 86256-59-9] (10.0 g, 52.3 mmol) in dioxane (20 mL) was added trifluoroacetic anhydride (8 mL, 57.2 mmol). The reaction mixture was stirred at room temperature for 1 h. The reaction mixture was concentrated under reduced pressure. The residue was partitioned between EtOAc and 1N HCl. The phases were separated. The organic phase was washed with a saturated solution of $NaHCO_3$ in water, $H_2O$ and brine, dried over $Na_2SO_4$, filtered and concentrated under reduced pressure to afford 14.7 g of 2,2,2-trifluoro-N-(2-methyl-4-(trifluoromethoxy)phenyl)acetamide 4a as a white powder. The compound was used in the next step without further purification.

Synthesis of Intermediate 4c

To acetic anhydride (11.4 mL, 61.1 mmol), cooled at 0° C. was added dropwise 70% nitric acid (3.9 mL). 2,2,2-Trifluoro-N-(2-methyl-4-(trifluoromethoxy)phenyl)-acetamide 4a (5 g, 17.4 mmol) was added portionwise and the reaction mixture was heated at 55° C. for 12 h. After cooling to room temperature, the reaction mixture was diluted with EtOAc and washed with $H_2O$. The organic phase was washed with brine, dried over $Na_2SO_4$, filtered and concentrated under reduced pressure. The residue was dissolved in methanol (46 mL). 2M $K_2CO_3$ (23 mL, 46 mmol) was added and the reaction mixture was heated at 70° C. for 4 h. More 2M $K_2CO_3$ (10 mL, 20 mmol) was added and the reaction mixture was heated at 70° C. for 12 h. The reaction mixture was partially concentrated under reduced pressure to remove methanol. The residue was extracted with EtOAc. The organic phase was washed with $H_2O$ and brine, dried over $Na_2SO_4$, filtered and concentrated under reduced pressure. The residue was purified by flash chromatography on silica gel using a gradient of EtOAc (20% to 50%) in heptane to afford 3.6 g of 2-methyl-6-nitro-4-(trifluoromethoxy)aniline 4c as a yellow solid.

Synthesis of Intermediate 4d

To a solution of 2-methyl-6-nitro-4-(trifluoromethoxy)aniline 4c (1.8 g, 7.69 mmol) in acetic acid (10.9 mL) was added dropwise a solution of sodium nitrite (0.806 g, 11.7 mmol) in $H_2SO_4/H_2O$ (2 mL, 1/1). The reaction mixture was stirred at room temperature for 30 min. $H_2O$ (22 mL) and urea (0.802 g, 13.4 mmol) were added. After 10 min at room temperature, a solution of potassium iodide (1.7 g, 10.2 mmol) in $H_2O$ (11 mL) was added dropwise. The reaction mixture was stirred at room temperature for 30 min. The yellow solid was filtered off, washed with $H_2O$ and dried to give 2.4 g of 2-iodo-1-methyl-3-nitro-5-(trifluoromethoxy)benzene 4d.

Synthesis of Intermediate 4e

To a solution of 2-iodo-1-methyl-3-nitro-5-(trifluoromethoxy)benzene 4d (3.5 g, 10.0 mmol) in EtOH (30 mL) was added a solution of $NH_4Cl$ (2.7 g, 49.9 mmol) in $H_2O$ (30 mL). The reaction mixture was heated at 50° C. Iron (2.6 g, 46.9 mmol) was added and the reaction mixture was heated under reflux for 40 min. After cooling to room temperature, the reaction mixture was filtered through Celite®. The solids were washed with EtOH. The filtrate was partially concentrated under reduced pressure to remove EtOH. The residue was partitioned between EtOAc and a saturated solution of $NaHCO_3$ in water. The phases were separated. The organic phase was washed with $H_2O$ and brine, dried over $Na_2SO_4$, filtered and concentrated under reduced pressure. The residue was purified by flash chromatography on silica gel using a gradient of EtOAc (0% to 25%) in heptane to afford 2.9 g of 2-iodo-3-methyl-5-(trifluoromethoxy)aniline 4e as a yellow oil.

Synthesis of Intermediate 4f

A solution of 2-iodo-3-methyl-5-(trifluoromethoxy)aniline 4e (2.9 g, 9.1 mmol) in triethylamine (23 mL) was degassed with argon for 15 min. Dichlorobis(triphenylphosphine)palladium(II) (0.327 g, 0.47 mmol), copper(I) iodide (0.164 g, 0.86 mmol) and trimethylsilylacetylene (1.8 mL, 13.1 mmol) were added. The reaction mixture was heated at 65° C. for 12 h. After cooling to room temperature, the reaction mixture was diluted with $H_2O$ and extracted with EtOAc (3×). The organic phases were combined, washed with $H_2O$ and brine, dried over $Na_2SO_4$, filtered and concentrated under reduced pressure. The residue was purified by flash chromatography on silica gel using a gradient of EtOAc (0% to 20%) in heptane to afford 2.6 g of 3-methyl-5-(trifluoromethoxy)-2-((trimethylsilyl)ethynyl)aniline 4f as an orange oil.

Synthesis of Intermediate 4g

To a solution of 3-methyl-5-(trifluoromethoxy)-2-((trimethylsilyl)ethynyl)aniline 4f (2.7 g, 9.3 mmol) in NMP (27 mL) was added tBuOK (3.1 g, 27.8 mmol). The reaction mixture was heated at 80° C. for 4 h. After cooling to room temperature, the reaction mixture was diluted with $H_2O$ and extracted with EtOAc (2×). The organic phases were combined, washed with $H_2O$ and brine, dried over $Na_2SO_4$, filtered and concentrated under reduced pressure. The residue was purified by flash chromatography on silica gel using a gradient of EtOAc (0% to 20%) in heptane to afford 1.7 g of 4-methyl-6-(trifluoromethoxy)-1H-indole 4g as an orange oil.

Synthesis of Intermediate 4h

At 0° C., $BH_3$-Pyridine (1.2 mL, 11.6 mmol) was added dropwise to a solution of 4-methyl-6-(trifluoromethoxy)-1H-indole 4g (0.5 g, 2.32 mmol) in EtOH (3 mL). 6N HCl (6 mL) was slowly added dropwise while maintaining the reaction temperature below 10° C. The mixture was stirred at 0° C. for 3 h. Water (12 mL) was added and the mixture was basified until pH 8-9 with a concentrated solution of NaOH in water (the reaction temperature was kept below 20° C.). The mixture was extracted with EtOAc. The organic layer was washed with water, dried over $MgSO_4$, filtered and the solvent was evaporated under reduced pressure. Toluene was added and the solution was concentrated under reduced pressure to give 450 mg of 4-methyl-6-(trifluoromethoxy)indoline 4h.

Synthesis of Intermediate 4i

N,N-Diisopropylethylamine (1.58 mL, 9.57 mmol) was added to a solution of 2-((3-(4-(tert-butoxy)-4-oxobutoxy)-5-methoxyphenyl)amino)-2-(4-chlorophenyl)acetic acid 2c (1.44 g, 3.19) and 4-methyl-6-(trifluoromethoxy)indoline 4h (846 mg, 3.51 mmol) in dry DMF (30 mL). HATU (1.82 g, 4.78 mmol) was added and the reaction mixture was stirred at room temperature for 2 h. The reaction mixture was poured out into water (400 mL) and the white suspension was extracted with EtOAc. The aqueous layer was saturated by the addition of NaCl and extracted again with EtOAc. The combined organic layers were washed with brine, water, dried over $MgSO_4$ and evaporated under reduced pressure. The residue was purified by column chromatography on silica gel (100 g) using a gradient of EtOAc:EtOH (3:1)/heptane 0/100 to 60/40. The product fractions were combined and evaporated under reduced pressure. The residue (1.47 g) was purified via preparative HPLC (Stationary phase: RP XBridge® Prep C18 OBD—10 μm, 50×150 mm, mobile phase: 0.25% $NH_4HCO_3$ solution in water, $CH_3CN$). The product fractions were combined and evaporated under reduced pressure to provide tert-butyl 4-(3-((1-(4-chlorophenyl)-2-(4-methyl-6-(trifluoromethoxy)indolin-1-yl)-2-oxoethyl)amino)-5-methoxyphenoxy)butanoate 4i (821 mg) as a white solid.

Synthesis of Compound 4 and Chiral Separation into Enantiomers 4A and 4B

Tert-butyl 4-(3-((1-(4-chlorophenyl)-2-(4-methyl-6-(trifluoromethoxy)indolin-1-yl)-2-oxoethyl)amino)-5-methoxyphenoxy)butanoate 4i (821 mg, 1.27 mmol) was mixed with 4M HCl in dioxane (9.5 mL) and the mixture was stirred at room temperature for 15 h. Nitrogen gas was bubbled through the reaction mixture for 30 min. The solvent was evaporated under reduced pressure to give 4-(3-((1-(4-chlorophenyl)-2-(4-methyl-6-(trifluoromethyl)indolin-1-yl)-2-oxoethyl)amino)-5-methoxyphenoxy)butanoic acid (Compound 4, 750 mg) as an off-white solid. The enantiomers of Compound 4 (750 mg) were separated via preparative chiral SFC (Stationary phase: Chiralcel® Diacel OD 20×250 mm, mobile phase: $CO_2$, EtOH+0.4% $iPrNH_2$). The product fractions were combined and evaporated under reduced pressure to give Enantiomer 4A as the first eluted product and Enantiomer 4B as the second eluted product. Both residues were mixed with EtOAc and water. The mixture was acidified to pH 1-2 with 1N HCl. The layers were separated and the aqueous layer was extracted twice with EtOAc. The combined organic layers were washed with water, dried over $MgSO_4$, filtered, and evaporated under reduced pressure. The residue was dried under vacuum at 50° C. to give Enantiomer 4A (213 mg) and Enantiomer 4B (194 mg) respectively.

Compound 4:

$^1$H NMR (360 MHz, DMSO-d$_6$) δ ppm 1.87 (quin, J=7.0 Hz, 2H) 2.20 (s, 3H) 2.33 (t, J=7.1 Hz, 2H) 2.98-3.16 (m, 2H) 3.61 (s, 3H) 3.84 (t, J=6.4 Hz, 2H) 4.04 (td, J=10.4, 7.0 Hz, 1H) 4.53 (td, J=10.3, 6.4 Hz, 1H) 5.56 (d, J=9.1 Hz, 1H) 5.76 (t, J=2.0 Hz, 1H) 5.91-5.98 (m, 2H) 6.45 (d, J=8.8 Hz, 1H) 6.87 (s, 1H) 7.38-7.47 (m, 2H) 7.50-7.61 (m, 2H) 7.89 (s, 1H) 12.18 (br s, 1H)

LC/MS (method LC-C): R$_t$ 1.14 min, MH$^+$ 593

Enantiomer 4A:

$^1$H NMR (360 MHz, DMSO-d$_6$) δ ppm 1.87 (quin, J=6.9 Hz, 2H) 2.20 (s, 3H) 2.34 (t, J=7.3 Hz, 2H) 2.98-3.16 (m, 2H) 3.62 (s, 3H) 3.85 (t, J=6.4 Hz, 2H) 4.05 (td, J=10.4, 7.0 Hz, 1H) 4.53 (td, J=10.3, 6.4 Hz, 1H) 5.56 (d, J=8.8 Hz, 1H) 5.76 (t, J=1.8 Hz, 1H) 5.91-5.99 (m, 2H) 6.45 (d, J=8.8 Hz, 1H) 6.88 (s, 1H) 7.38-7.49 (m, 2H) 7.51-7.61 (m, 2H) 7.89 (s, 1H) 12.17 (br s, 1H)

LC/MS (method LC-C): R$_t$ 1.29 min, MH$^+$ 593

[∼]$_D^{20}$: −39.6° (c 0.455, DMF)

Chiral SFC (method SFC-C): R$_t$ 3.34 min, MH$^+$ 593 chiral purity 100%.

Enantiomer 4B:

$^1$H NMR (360 MHz, DMSO-d$_6$) δ ppm 1.88 (quin, J=6.9 Hz, 2H) 2.20 (s, 3H) 2.34 (t, J=7.1 Hz, 2H) 2.98-3.16 (m, 2H) 3.62 (s, 3H) 3.85 (t, J=6.4 Hz, 2H) 4.05 (td, J=10.3, 7.1 Hz, 1H) 4.53 (td, J=10.2, 6.6 Hz, 1H) 5.56 (d, J=8.8 Hz, 1H) 5.76 (t, J=1.8 Hz, 1H) 5.92-5.99 (m, 2H) 6.46 (d, J=8.8 Hz, 1H) 6.88 (s, 1H) 7.38-7.49 (m, 2H) 7.50-7.63 (m, 2H) 7.89 (s, 1H) 12.16 (br s, 1H)

LC/MS (method LC-C): R$_t$ 1.30 min, MH$^+$ 593

[α]$_D^{20}$: +43.7° (c 0.38, DMF)

Chiral SFC (method SFC-C): R$_t$ 3.16 min, MH$^+$ 593 chiral purity 100%.

Example 5: synthesis of 4-(3-((1-(4-chlorophenyl)-2-(5-fluoro-6-(trifluoromethoxy)indolin-1-yl)-2-oxoethyl)amino)-5-methoxyphenoxy)butanoic Acid (Compound 5) and Chiral Separation into Enantiomers 5A and 5B

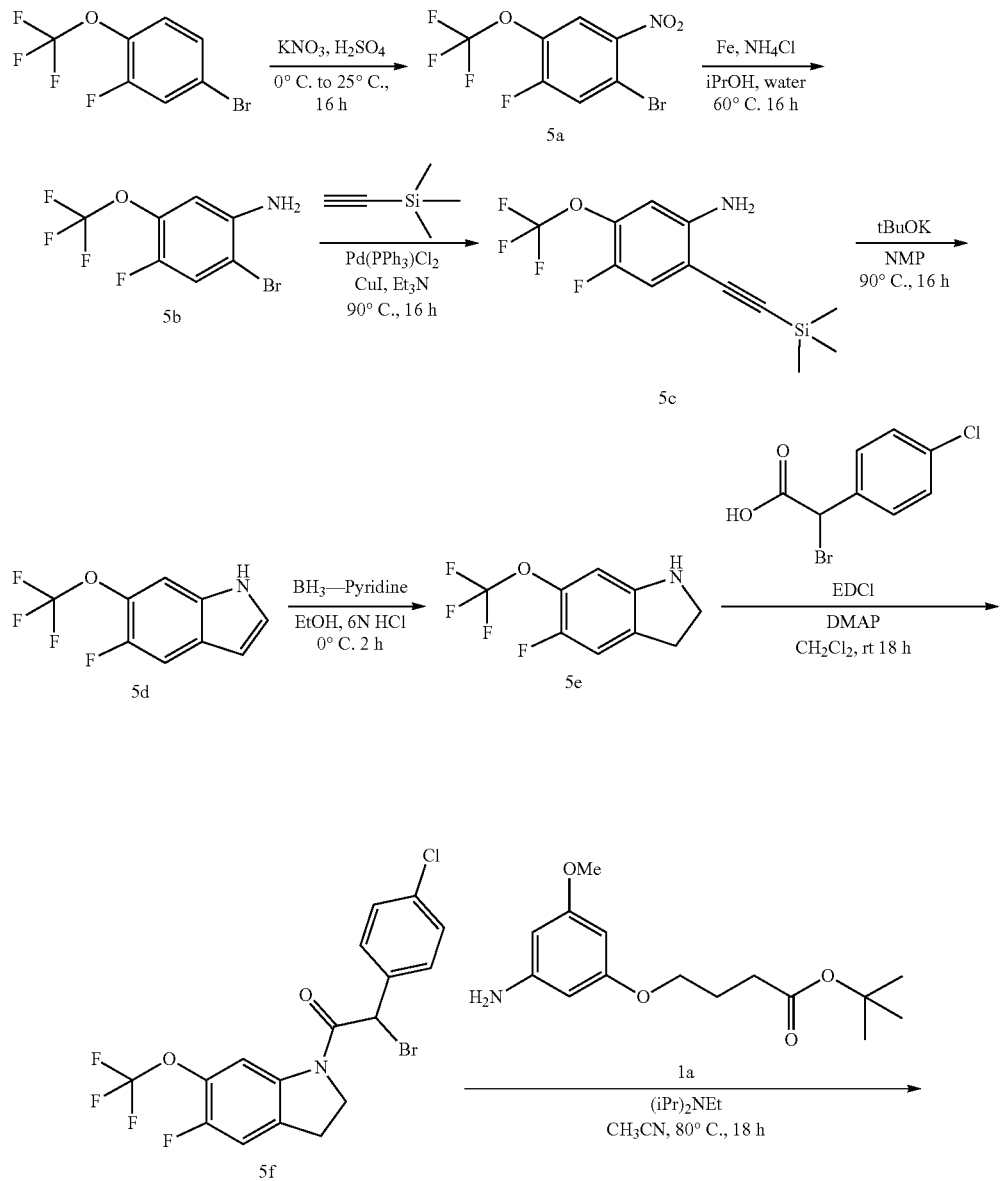

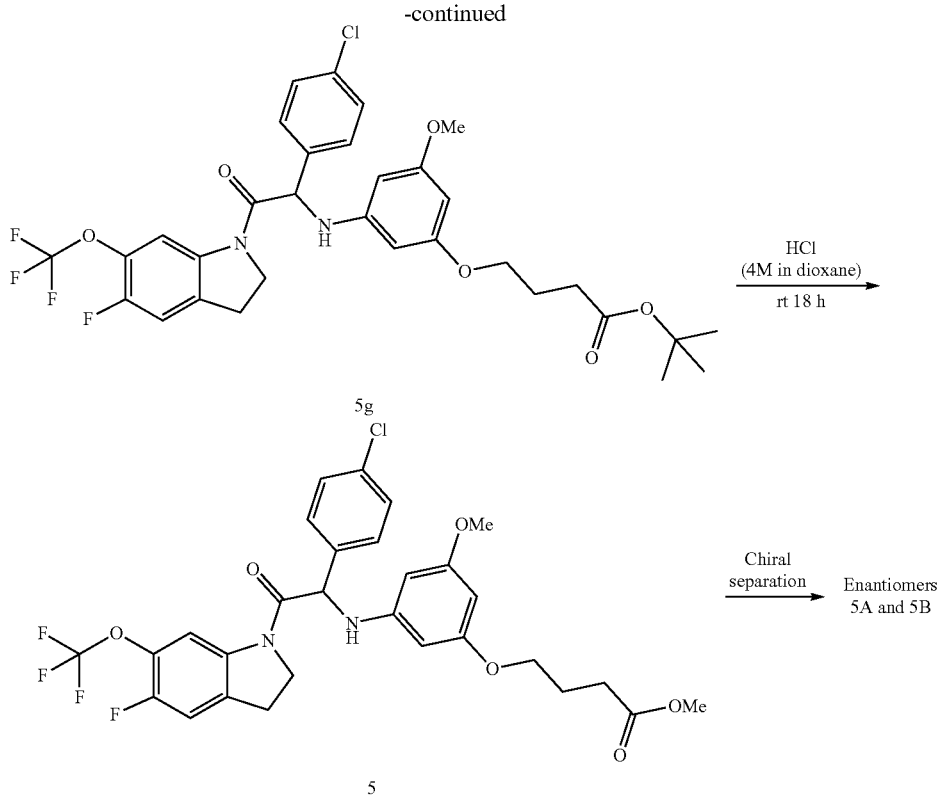

Synthesis of Intermediate 5a

A solution of 4-bromo-2-fluoro-1-(trifluoromethoxy)benzene [CAS 105529-58-6] (98.7 g, 381.1 mmol) in concentrated $H_2SO_4$ (98%, 200 mL), was cooled to 0° C. with an ice-bath. KNOB (43.0 g, 425.3 mmol) was added in portions. After addition, the ice-bath was removed and the mixture was stirred at room temperature for 16 h. The reaction mixture was poured out into ice-water (2 L) while stirring. The mixture was extracted with $CH_2Cl_2$ (3×500 mL). The combined organic layers were washed with a saturated aqueous $NaHCO_3$ solution (2×500 mL), brine (500 mL), dried over $MgSO_4$, filtered and concentrated under reduced pressure to afford 1-bromo-5-fluoro-2-nitro-4-(trifluoromethoxy)benzene 5a (117.2 g), which was used in the next step without further purification.

Synthesis of Intermediate 5b

To a stirred suspension of 1-bromo-5-fluoro-2-nitro-4-(trifluoromethoxy)benzene 5a (70.0 g, 230 mmol) and $NH_4Cl$ (123.2 g, 2.30 mol) in iPrOH (1 L) and water (330 mL) was added reductive iron powder (64.3 g, 1.15 mol) under $N_2$-atmosphere. The reaction mixture was stirred at 60° C. for 16 h. The reaction mixture was diluted with EtOAc (1 L) and filtered through Celite®. The filtrate was concentrated under reduced pressure. The residue was partitioned between EtOAc (1 L) and water (800 mL). The layers were separated and the organic phase was washed with brine (1 L), dried over $MgSO_4$, filtered and concentrated under reduced pressure. The residue was purified by distillation under reduced pressure (oil pump, b.p. 60-64° C.). 2-Bromo-4-fluoro-5-(trifluoromethoxy)aniline 5b (47.3 g) was obtained as a yellow oil.

Synthesis of Intermediate 5c

To a mixture of 2-bromo-4-fluoro-5-(trifluoromethoxy)aniline 5b (18.4 g, 67.2 mmol) and ethynyl(trimethyl)silane (19.9 g, 202.4 mmol, 28.00 mL) in $Et_3N$ (300 mL) was added CuI (1.28 g, 6.72 mmol) and $Pd(PPh_3)_2Cl_2$ (2.40 g, 3.42 mmol). The reaction mixture was heated under $N_2$-atmosphere at 90° C. for 16 h. After cooling to room temperature, the mixture was diluted with MTBE (300 mL) and filtered through Celite®. The filtrate was concentrated under reduced pressure. The residue was purified by flash chromatography on silica gel (ISCO®, 220 g SepaFlash® Silica Flash Column, eluent: gradient of 0 to 5% EtOAc in petroleum ether @100 mL/min). 4-Fluoro-5-(trifluoromethoxy)-2-((trimethylsilyl)ethynyl)aniline 5c (16.1 g, 90% purity) was obtained as a brown oil.

Synthesis of Intermediate 5d

A mixture of 4-fluoro-5-(trifluoromethoxy)-2-((trimethylsilyl)ethynyl)aniline 5c (16.1 g, 55.3 mmol) and tBuOK (18.6 g, 165.8 mmol) in NMP (220.00 mL) was heated at 90° C. for 16 h under $N_2$-atmosphere. After cooling to room temperature, the reaction mixture was poured out into ice-water (1 L) and extracted with MTBE (3×300 mL). The combined organic phases were washed with water (2×200 mL), brine (300 mL), dried over $MgSO_4$, filtered and concentrated under reduced pressure. The residue was purified by flash chromatography on silica gel (ISCO®, 120 g SepaFlash® Silica Flash Column, eluent: gradient of 0 to 5% EtOAc in petroleum ether @ 85 mL/min) to afford 5-fluoro-6-(trifluoromethoxy)-1H-indole 5d (11 g) product as a dark-green oil. The residue was combined with another fraction (total amount=17.2 g) and further purified by distillation under reduced pressure (oil pump, b.p. 60-64° C.) to provide 5-fluoro-6-(trifluoromethoxy)-1H-indole 5d (14.7 g, 95% purity) as a colorless oil.

Synthesis of Intermediate 5e

At 0° C., BH$_3$-pyridine (13.8 mL, 136.9 mmol) was added dropwise to a solution of 5-fluoro-6-(trifluoromethoxy)-1H-indole 5d (6 g, 27.4 mmol) in EtOH (40 mL). 6N HCl (90 mL) was added dropwise while maintaining the temperature below 10° C. The mixture was stirred at 0° C. for 2 h. Water (100 mL) was added and the mixture was basified to pH 8-9 with a concentrated solution of NaOH in water (the reaction temperature was kept below 20° C.). The mixture was extracted with CH$_2$Cl$_2$. The organic layer was washed with water, dried over MgSO$_4$, filtered and the solvent was evaporated under reduced pressure. Toluene was added and the solution was concentrated under reduced pressure to give 5.52 g of 5-fluoro-6-(trifluoromethoxy)indoline 5e. The compound was used in the next reaction step without further purification.

Synthesis of Intermediate 5f

To a mixture of 2-bromo-2-(4-chlorophenyl)acetic acid [CAS 3381-73-5] (0.61 g, 2.4 mmol), 5-fluoro-6-(trifluoromethoxy)indoline 5e (0.55 g, 2.2 mmol) and DMAP (0.027 g, 0.22 mmol) in CH$_2$Cl$_2$ (14 mL) was added EDCI (0.51 g, 2.7 mmol). The mixture was stirred at room temperature for 18 h. The mixture was diluted with a 10% K$_2$CO$_3$ solution in water. The layers were decanted. The organic layer was washed with water, dried over MgSO$_4$, filtered and the solvent was concentrated under reduced pressure to give 2-bromo-2-(4-chlorophenyl)-1-(5-fluoro-6-(trifluoromethoxy)indolin-1-yl)ethanone 5f (1.1 g, purple oil). The compound was used in the next step without further purification.

Synthesis of Intermediate 5g

A mixture of 2-bromo-2-(4-chlorophenyl)-1-(5-fluoro-6-(trifluoromethoxy)indolin-1-yl)ethanone 5f (1.1 g, 2.2 mmol), tert-butyl 4-(3-amino-5-methoxyphenoxy)butanoate 1a (1.0 g, 3.3 mmol) and diisopropylethylamine (1.5 mL, 8.7 mmol) in CH$_3$CN (29 mL) was stirred at 80° C. for 18 h. The reaction mixture was concentrated under reduced pressure. The residue was purified by flash chromatography on silica gel (30 μm, 40 g, heptane/EtOAc gradient 85/15 to 75/25). The fractions containing the expected compound were combined and the solvent was concentrated under reduced pressure to give tert-butyl 4-(3-((1-(4-chlorophenyl)-2-(5-fluoro-6-(trifluoromethoxy)indolin-1-yl)-2-oxoethyl)amino)-5-methoxyphenoxy)butanoate 5g (480 mg, 57% purity by LC/MS).

Synthesis of Compound 5 and Chiral Separation into Enantiomers 5A and 5B

A mixture of tert-butyl 4-(3-((1-(4-chlorophenyl)-2-(5-fluoro-6-(trifluoromethoxy)indolin-1-yl)-2-oxoethyl) amino)-5-methoxyphenoxy)butanoate 5g (0.48 g, 0.42 mmol, 57% purity) in HCl (4M in dioxane) (4.6 mL) was stirred at room temperature for 18 h. The mixture was concentrated under reduced pressure, taken up in Et$_3$N (5 mL) and concentrated again in vacuo. The residue was purified by flash chromatography on silica gel (30 μm, 24 g, CH$_2$Cl$_2$/MeOH gradient 99/1 to 96/4). The pure fractions were combined and evaporated to dryness. The residue (150 mg) was further purified via Reverse Phase HPLC (Stationary phase: YMC-actus Triart-C18 10 μm 30×150 mm, mobile phase: gradient from 65% NH$_4$HCO$_3$ 0.2%, 35% CH$_3$CN to 25% NH$_4$HCO$_3$ 0.2%, 75% CH$_3$CN) to give 4-(3-((1-(4-chlorophenyl)-2-(5-fluoro-6-(trifluoromethoxy) indolin-1-yl)-2-oxoethyl)amino)-5-methoxyphenoxy)butanoic acid (Compound 5, 71 mg). The enantiomers (55 mg) were separated via chiral SFC (Stationary phase: Chiralcel® OD-H 5 μm 250×20 mm, mobile phase: 55% CO$_2$, 45% MeOH) to give, after freeze-drying from a solvent mixture of CH$_3$CN/water the first eluted Enantiomer 5A (25 mg, white solid) and the second eluted Enantiomer 5B (25 mg, white solid).

Compound 5:

$^1$H NMR (500 MHz, DMSO-d$_6$) δ ppm 1.86 (quin, J=6.70 Hz, 2H) 2.24-2.43 (m, 2H) 3.06-3.25 (m, 2H) 3.61 (s, 3H) 3.84 (br t, J=6.31 Hz, 2H) 3.94-4.13 (m, 1H) 4.46-4.57 (m, 1H) 5.56 (br d, J=8.83 Hz, 1H) 5.75 (s, 1H) 5.93 (s, 1H) 5.95 (s, 1H) 6.45 (br d, J=8.83 Hz, 1H) 7.44 (br d, J=8.20 Hz, 3H) 7.54 (br d, J=8.20 Hz, 2H) 8.16 (br d, J=6.62 Hz, 1H) 12.12 (br s, 1H)

LC/MS (method LC-A): Rt 3.00 min, MH$^+$ 597

Enantiomer 5A:

$^1$H NMR (500 MHz, DMSO-de) δ ppm 1.86 (quin, J=6.94 Hz, 2H) 2.25-2.44 (m, 2H) 3.06-3.26 (m, 2H) 3.61 (s, 3H) 3.84 (t, J=6.46 Hz, 2H) 4.05 (td, J=10.32, 7.09 Hz, 1H) 4.48-4.55 (m, 1H) 5.56 (d, J=8.83 Hz, 1H) 5.76 (t, J=1.89 Hz, 1H) 5.94 (br d, J=11.98 Hz, 2H) 6.45 (d, J=8.83 Hz, 1H) 7.42-7.46 (m, 3H) 7.54 (d, J=8.20 Hz, 2H) 8.16 (br d, J=6.94 Hz, 1H) 12.01 (br s, 1H)

LC/MS (method LC-A): R$_t$ 3.00 min, MH$^+$ 597

$[α]_D^{20}$: −35.8° (c 0.257, DMF)

Chiral SFC (method SFC-H): R$_t$ 1.34 min, MH$^+$ 597 chiral purity 100%.

Enantiomer 5B:

$^1$H NMR (500 MHz, DMSO-d$_6$) δ ppm 1.85 (quin, J=6.86 Hz, 2H) 2.27 (t, J=7.25 Hz, 2H) 3.10-3.31 (m, 2H) 3.61 (s, 3H) 3.78-3.90 (m, 2H) 4.05 (td, J=10.40, 7.25 Hz, 1H) 4.52 (td, J=10.32, 6.46 Hz, 1H) 5.57 (d, J=8.83 Hz, 1H) 5.75 (t, J=1.89 Hz, 1H) 5.94 (br d, J=16.39 Hz, 2H) 6.45 (d, J=8.83 Hz, 1H) 7.41-7.46 (m, 3H) 7.55 (d, J=8.51 Hz, 2H) 8.16 (br d, J=6.94 Hz, 1H)

LC/MS (method LC-A): R$_t$ 3.00 min, MH$^+$ 597

$[α]_D^{20}$: +52.8° (c 0.231, DMF)

Chiral SFC (method SFC-H): R$_t$ 3.14 min, MH$^+$ 597 chiral purity 100%.

Example 6: synthesis of 4-(3-((1-(4-fluoro-2-methoxyphenyl)-2-oxo-2-(6-(trifluoromethoxy)indolin-1-yl)ethyl)amino)-5-methoxyphenoxy)butanoic Acid (Compound 6) and Chiral Separation into Enantiomers 6A and 6B
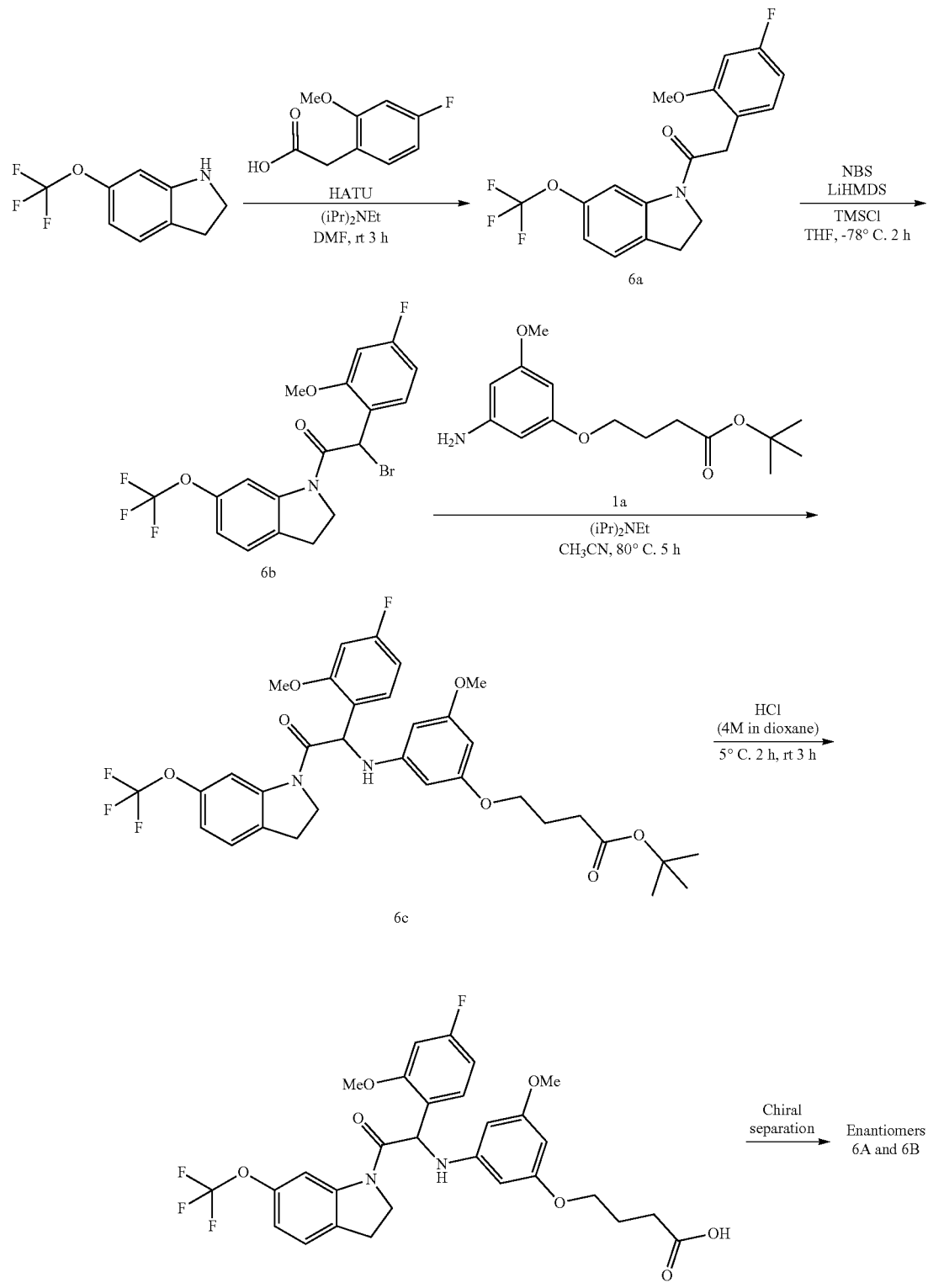

Synthesis of Intermediate 6a

A mixture of 6-(trifluoromethoxy)indoline [CAS 959235-95-1] (2 g, 9.84 mmol), 2-(4-fluoro-2-methoxyphenyl)acetic acid [CAS 886498-61-9] (2.17 g, 10.8 mmol), HATU (5.62 g, 14.8 mmol) and diisopropylethylamine (4.9 mL, 29.5 mmol) in DMF (20 mL) was stirred at room temperature for 3 h. Water and ice were added and the precipitate was filtered off and dried to give 2-(4-fluoro-2-methoxyphenyl)-1-(6-(trifluoromethoxy)indolin-1-yl)ethanone 6a (3.44 g).

Synthesis of Intermediate 6b

At −78° C. under a $N_2$ flow, LiHMDS (18.7 mL, 18.7 mmol) was added dropwise to a mixture of 2-(4-fluoro-2-methoxyphenyl)-1-(6-(trifluoromethoxy)indolin-1-yl)ethanone 6a (3.44 g, 9.32 mmol) in THF (45 mL). TMSCl (1.42 mL, 11.2 mmol) was added dropwise. The mixture was stirred for 15 min at −78° C. and N-bromosuccinimide (1.83 g, 10.2 mmol) in THF (35 mL) was added dropwise. After stirring for 2 h at −78° C., the reaction was quenched with a saturated $NH_4Cl$ solution. The mixture was extracted with EtOAc, dried over $MgSO_4$, filtered and the solvent was concentrated under reduced pressure to give 2-bromo-2-(4-fluoro-2-methoxyphenyl)-1-(6-(trifluoromethoxy)indolin-1-yl)ethanone 6b (4.48 g). The crude compound was used without further purification in the next step.

Synthesis of Intermediate 6c

A mixture of 2-bromo-2-(4-fluoro-2-methoxyphenyl)-1-(6-(trifluoromethoxy)indolin-1-yl)ethanone 6b (2.0 g, 4.46 mmol), tert-butyl 4-(3-amino-5-methoxyphenoxy)butanoate 1a (1.26 g, 4.46 mmol) and diisopropylethylamine (1.15 mL, 6.69 mmol) in $CH_3CN$ (45 mL) was stirred at 80° C. for 5 h. The reaction mixture was concentrated under reduced pressure. The residue was purified by flash chromatography on silica gel (15-40 μm, 40 g, heptane/EtOAc 85/15). The fractions containing expected compound were combined and the solvent was concentrated under reduced pressure to give tert-butyl 4-(3-((1-(4-fluoro-2-methoxyphenyl)-2-oxo-2-(6-(trifluoromethoxy)indolin-1-yl)ethyl)amino)-5-methoxyphenoxy)butanoate 6c (1.6 g, 67% purity by LC/MS).

Synthesis of Compound 6 and Chiral Separation into Enantiomers 6A and 6B

A solution of tert-butyl 4-(3-((1-(4-fluoro-2-methoxyphenyl)-2-oxo-2-(6-(trifluoromethoxy)indolin-1-yl)ethyl)amino)-5-methoxyphenoxy)butanoate 6c (1.5 g, 2.31 mmol) in HCl (4M in dioxane) (15 mL) was stirred at 5° C. for 2 h and at room temperature for 3 h. The solvent was concentrated under reduced pressure and 3N NaOH were added until neutral pH was obtained. The solution was extracted with EtOAc. The organic layer was dried over $MgSO_4$, filtered and concentrated under reduced pressure. The residue was purified by flash chromatography on silica gel (20-45 μm, 40 g, $CH_2Cl_2$/MeOH gradient 99.5/0.5 to 95/5). The pure fractions were combined and the solvent was concentrated under reduced pressure to provide Compound 6 (646 mg). A small fraction was crystallized from $CH_3CN$/diisopropyl ether to give 4-(3-((1-(4-fluoro-2-methoxyphenyl)-2-oxo-2-(6-(trifluoromethoxy)indolin-1-yl)ethyl)amino)-5-methoxyphenoxy)butanoic acid (Compound 6, 35 mg). The remaining amount (600 mg) was used for chiral separation of the enantiomers via chiral SFC (Stationary phase: Chiralcel® OD-H 5 μm 250×20 mm, mobile phase: 60% $CO_2$, 40% MeOH). To provide Enantiomer 6A as the first eluted product and Enantiomer 6B as the second eluted product. Both enantiomers were further purified by flash chromatography on silica gel (20-45 μm, 12 g, $CH_2Cl_2$/MeOH gradient 100/0 to 95/5). The pure fractions were combined and the solvent was concentrated under reduced pressure to give, after solidification in diisopropyl ether/pentane (+a few drops of $CH_3CN$), Enantiomer 6A (108 mg) and Enantiomer 6B (108 mg), respectively.

Compound 6:

$^1$H NMR (400 MHz, DMSO-$d_6$) δ ppm 1.87 (quin, J=6.82 Hz, 2H) 2.33 (t, J=7.33 Hz, 2H) 3.08-3.27 (m, 2H) 3.61 (s, 3H) 3.78-3.91 (m, 5H) 3.92-4.02 (m, 1H) 4.33-4.42 (m, 1H) 5.59 (d, J=8.59 Hz, 1H) 5.75 (s, 1H) 5.87 (br d, J=7.07 Hz, 2H) 6.39 (br d, J=8.59 Hz, 1H) 6.78 (td, J=8.46, 2.27 Hz, 1H) 6.94-7.02 (m, 2H) 7.29-7.35 (m, 2H) 8.03 (s, 1H) 12.14 (br s, 1H)

LC/MS (method LC-B): Rt 2.76 min, MH$^+$ 593

Melting point: 164° C.

Enantiomer 6A:

$^1$H NMR (500 MHz, DMSO-$d_6$) δ ppm 1.87 (quin, J=6.78 Hz, 2H) 2.31-2.47 (m, 2H) 3.10-3.28 (m, 2H) 3.62 (s, 3H) 3.80-3.93 (m, 5H) 3.93-4.06 (m, 1H) 4.33-4.44 (m, 1H) 5.59 (br d, J=8.51 Hz, 1H) 5.76 (s, 1H) 5.88 (br d, J=8.83 Hz, 2H) 6.39 (br d, J=8.83 Hz, 1H) 6.79 (td, J=8.43, 2.05 Hz, 1H) 6.95-7.04 (m, 2H) 7.30-7.37 (m, 2H) 8.03 (s, 1H) 12.16 (br s, 1H)

LC/MS (method LC-A): $R_t$ 2.86 min, MH$^+$ 593

$[α]_D^{20}$: −37.3° (c 0.255, DMF)

Chiral SFC (method SFC-I): $R_t$ 1.03 min, MH$^+$ 593 chiral purity 100%.

Enantiomer 6B:

$^1$H NMR (500 MHz, DMSO-$d_6$) δ ppm 1.87 (quin, J=6.86 Hz, 2H) 2.30-2.45 (m, 2H) 3.09-3.26 (m, 2H) 3.62 (s, 3H) 3.80-3.93 (m, 5H) 3.93-4.06 (m, 1H) 4.33-4.44 (m, 1H) 5.59 (br d, J=8.51 Hz, 1H) 5.76 (s, 1H) 5.88 (br d, J=8.83 Hz, 2H) 6.39 (br d, J=8.51 Hz, 1H) 6.79 (td, J=8.43, 2.05 Hz, 1H) 6.95-7.04 (m, 2H) 7.30-7.37 (m, 2H) 8.03 (br s, 1H), 12.18 (br s, 1H)

LC/MS (method LC-A): $R_t$ 2.88 min, MH$^+$ 593

$[α]_D^{20}$: +32.7° (c 0.294, DMF)

Chiral SFC (method SFC-I): $R_t$ 1.82 min, MH$^+$ 593 chiral purity 99.56%.

Example 7: synthesis of 4-(3-((1-(4-chlorophenyl)-1-deuterio-2-oxo-2-(6-(trifluoromethoxy)indolin-1-yl)ethyl)amino)-5-methoxyphenoxy)butanoic Acid (Compound 7-D) and Chiral Separation into Enantiomers 7A-D and 7B-D
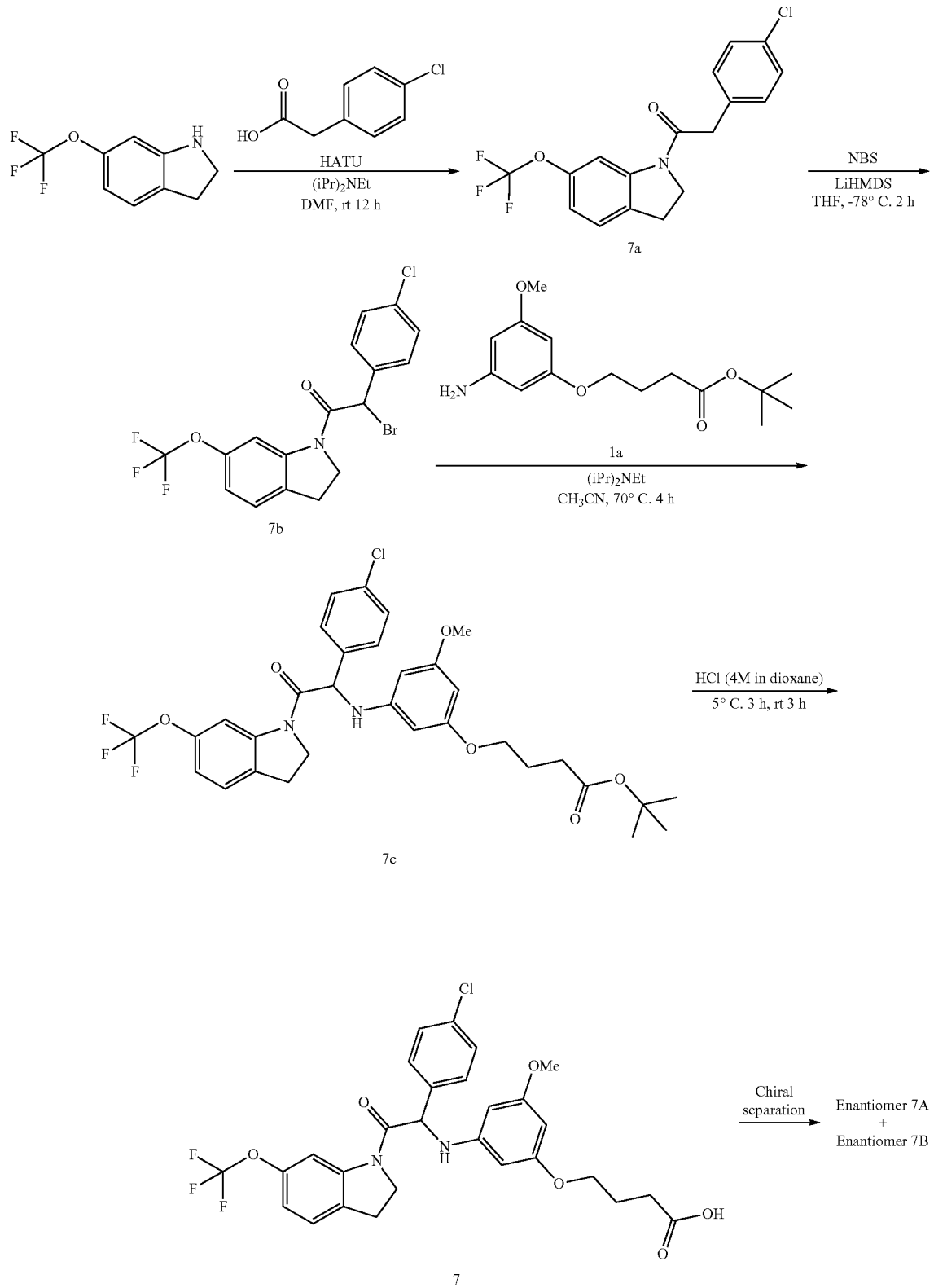

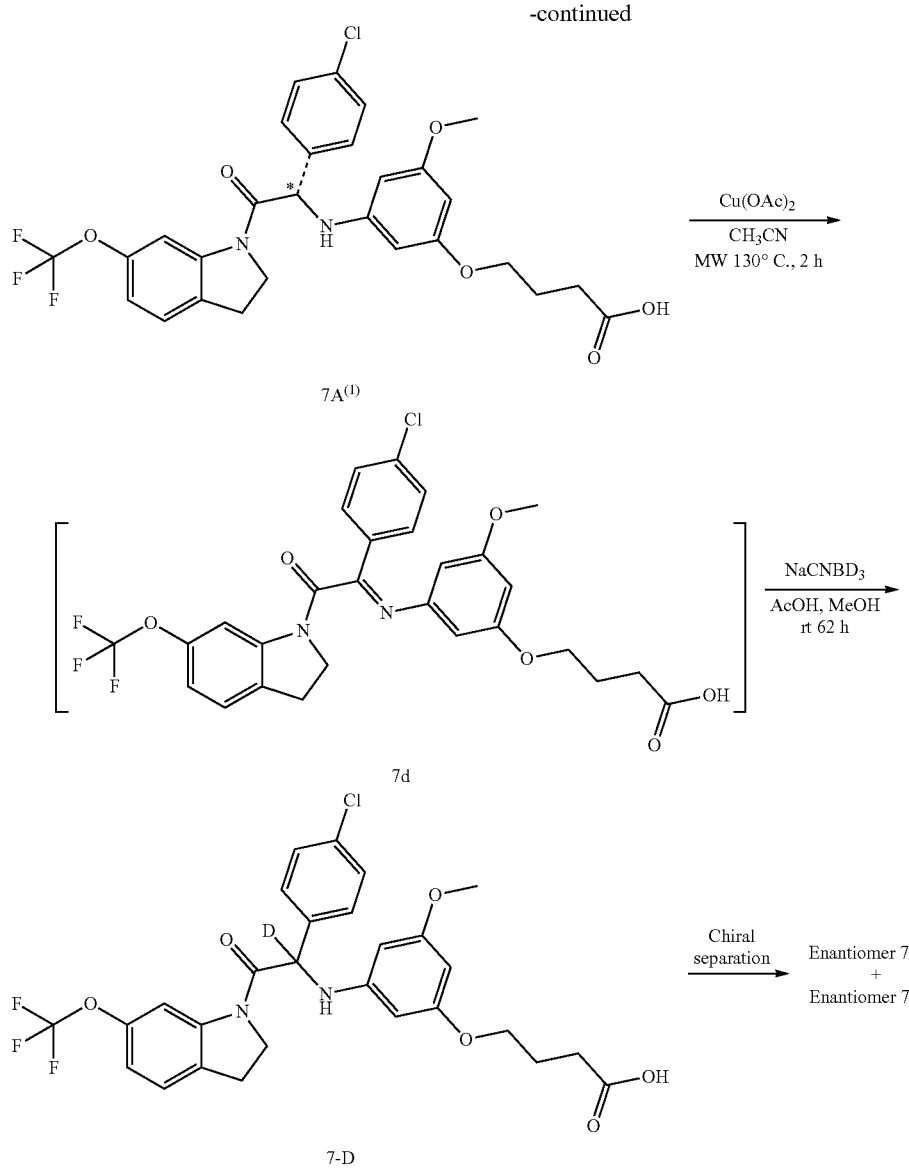

(1)The absolute stereochemistry of the chiral center (*) of Enantiomer 7A has not been determined Synthesis of Intermediate 7a A mixture of 6-(trifluoromethoxy)indoline [CAS 959235-95-1] (2 g, 9.84 mmol), 2-(4-chlorophenyl)acetic acid [CAS 1878-66-6] (1.85 g, 10.8 mmol), HATU (5.6 g, 14.8 mmol) and diisopropylethylamine (4.9 mL, 29.5 mmol) in DMF (40 mL) was stirred at room temperature for 12 h. Water was added and the precipitate was filtered off. The residue was taken up with EtOAc. The organic solution was washed with a 10% aqueous solution of $K_2CO_3$, brine, dried over $MgSO_4$, filtered and the solvent was evaporated under reduced pressure. The residue was purified by chromatography on silica gel (15-40 μm, 80 g, heptane/EtOAc gradient 90/10 to 60/40). The pure fractions were combined and the solvent was concentrated under reduced pressure to give 2-(4-chlorophenyl)-1-(6-(trifluoromethoxy)indolin-1-yl)ethanone 7a (3 g).

Synthesis of Intermediate 7b

At −78° C., under $N_2$ flow, LiHMDS 1.5 M in THF (11.2 mL, 16.9 mmol) was added dropwise to a mixture of 2-(4-chlorophenyl)-1-(6-(trifluoromethoxy)indolin-1-yl)ethanone 7a (3 g, 8.43 mmol) in THF (50 mL). The mixture was stirred for 15 min at −78° C. and a solution of N-bromosuccinimide (1.65 g, 9.3 mmol) in THF (30 mL) was added dropwise. After stirring for 2 h at −78° C., the reaction was quenched with a saturated solution of $NH_4Cl$. The mixture was extracted with EtOAc. The organic layer was separated, dried over $MgSO_4$, filtered and the solvent was evaporated under reduced pressure to give 2-bromo-2-(4-chlorophenyl)-1-(6-(trifluoromethoxy)indolin-1-yl)ethanone 7b (3.6 g). The compound was used as such in the next step.

Synthesis of Intermediate 7c

A mixture of 2-bromo-2-(4-chlorophenyl)-1-(6-(trifluoromethoxy)indolin-1-yl)ethanone 7b (3.6 g, 8.3 mmol), tert-butyl 4-(3-amino-5-methoxyphenoxy)-butanoate 1a (2.3 g, 8.3 mmol) and diisopropylethylamine (1.7 mL, 9.94 mmol) in $CH_3CN$ (80 mL) was stirred at 70° C. for 4 h. The mixture was concentrated under reduced pressure, diluted with EtOAc, and washed with 1N HCl and water. The organic phase was separated, dried over $MgSO_4$, filtered and the solvent was evaporated under reduced pressure. The compound was purified by flash chromatography on silica gel (15-40 µm, 120 g, heptane/EtOAc 80/20). The pure fractions were combined and evaporated to dryness to give, after crystallization from diisopropyl ether, tert-butyl 4-(3-((1-(4-chlorophenyl)-2-oxo-2-(6-(trifluoro-methoxy)indolin-1-yl)ethyl)amino)-5-methoxyphenoxy)butanoate 7c (2.6 g).

Synthesis of Compound 7 and Chiral Separation into Enantiomers 7A and 7B

A solution of tert-butyl 4-(3-((1-(4-chlorophenyl)-2-oxo-2-(6-(trifluoromethoxy)-indolin-1-yl)ethyl)amino)-5-methoxyphenoxy)butanoate 7c (2.4 g, 3.8 mmol) in HCl (4M in dioxane) (24 mL) was stirred at 5° C. for 3 h and at room temperature for 3 h. The precipitate was filtered off and dried to afford 4-(3-((1-(4-chlorophenyl)-2-oxo-2-(6-(trifluoromethoxy)indolin-1-yl)ethyl)amino)-5-methoxyphenoxy)butanoic acid as an HCl salt (Compound 7, 2 g, 0.8 equiv. HCl, 0.07 equiv. $H_2O$). Compound 7 (2 g, HCl salt) was neutralized prior to chiral separation by treatment of a solution of Compound 7 (HCl salt) with 1N NaOH and evaporation of the organic layer under reduced pressure. The enantiomers were separated via Preparative Chiral SFC (Stationary phase: Chiralcel® OD-H 5 µm 250×30 mm, mobile phase: 50% $CO_2$, 50% iPrOH (+0.3% $iPrNH_2$)) and further purified via Preparative achiral SFC (Stationary phase: Cyano® 6 µm 150×21.2 mm, mobile phase: 80% $CO_2$, 20% MeOH (+0.3% $iPrNH_2$)). The product fractions were combined and evaporated under reduced pressure. The two enantiomers were taken up with EtOAc and washed with 1N HCl. The organic layers were separated, dried over $MgSO_4$, filtered and the solvent was evaporated under reduced pressure. The first eluted enantiomer was solidified from ether/diisopropyl ether to give Enantiomer 7A (616 mg). The second eluted enantiomer was solidified from ether/diisopropyl ether to give Enantiomer 7B (715 mg).

Compound 7:
$^1$H NMR (500 MHz, DMSO-$d_6$) δ ppm 1.87 (quin, J=6.9 Hz, 2H) 2.34 (t, J=7.3 Hz, 2H) 3.07-3.28 (m, 2H) 3.62 (s, 3H) 3.85 (t, J=6.5 Hz, 2H) 4.04 (td, J=10.5, 7.1 Hz, 1H) 4.52 (td, J=10.3, 6.5 Hz, 1H) 5.57 (s, 1H) 5.76 (t, J=2.2 Hz, 1H) 5.90-6.00 (m, 2H) 7.01 (dd, J=8.2, 1.6 Hz, 1H) 7.33 (d, J=8.2 Hz, 1H) 7.41-7.48 (m, 2H) 7.55 (d, J=8.5 Hz, 2H) 8.03 (s, 1H)

LC/MS (method LC-B): $R_t$ 2.70 min, MH+ 579
Melting point: 150° C.

Enantiomer 7A:
$^1$H NMR (500 MHz, DMSO-$d_6$) δ ppm 1.87 (quin, J=6.7 Hz, 2H) 2.34 (br t, J=7.3 Hz, 2H) 3.08-3.27 (m, 2H) 3.62 (s, 3H) 3.85 (br t, J=6.3 Hz, 2H) 3.99-4.11 (m, 1H) 4.47-4.57 (m, 1H) 5.57 (br s, 1H) 5.76 (s, 1H) 5.95 (br d, J=10.1 Hz, 2H) 6.45 (br s, 1H) 7.01 (br d, J=7.6 Hz, 1H) 7.34 (br d, J=7.9 Hz, 1H) 7.44 (br d, J=8.5 Hz, 2H) 7.55 (br d, J=8.2 Hz, 2H) 8.04 (br s, 1H) 12.12 (br s, 1H)

LC/MS (method LC-A): $R_t$ 2.95 min, MH+ 579
$[α]_D^{20}$: −48.5° (c 0.27, DMF)
Chiral SFC (method SFC-D): $R_t$ 1.13 min, MH+ 579, chiral purity 100%.

Enantiomer 7B:
$^1$H NMR (500 MHz, DMSO-$d_6$) δ ppm 1.87 (br t, J=6.8 Hz, 2H) 2.34 (br t, J=7.3 Hz, 2H) 3.09-3.27 (m, 2H) 3.62 (s, 3H) 3.85 (br t, J=6.1 Hz, 2H) 3.99-4.10 (m, 1H) 4.46-4.59 (m, 1H) 5.57 (s, 1H) 5.76 (br s, 1H) 5.95 (br d, J=10.1 Hz, 2H) 6.45 (br s, 1H) 7.01 (br d, J=7.9 Hz, 1H) 7.34 (br d, J=7.9 Hz, 1H) 7.44 (br d, J=8.2 Hz, 2H) 7.55 (br d, J=8.2 Hz, 2H) 8.04 (br s, 1H) 12.12 (br s, 1H)

LC/MS (method LC-A): $R_t$ 2.94 min, MH+ 579
$[α]_D^{20}$: +42.9° (c 0.28, DMF)
Chiral SFC (method SFC-D): $R_t$ 2.13 min, MH+ 579, chiral purity 100%.

Synthesis of Deuterated Compound 7-D and Chiral Separation into Enantiomers 7A-D and 7B-D Copper(II) acetate (241 mg, 1.33 mmol) was added in one portion to a solution of Enantiomer 7A (384 mg, 0.663 mmol) in $CH_3CN$ (15 mL) at room temperature. The reaction mixture was heated in a sealed tube under microwave irradiation at 130° C. for 2 h. The reaction mixture was evaporated to dryness under reduced pressure and the residue was taken up with $CH_2Cl_2$ and water. The layers were separated. The aqueous layer was extracted again with $CH_2Cl_2$. The combined organic layers were washed with brine and water, dried over $MgSO_4$, filtered, and evaporated under reduced pressure. The residue, containing crude intermediate 7d was dissolved in MeOH (20 mL). Sodium cyanoborodeuteride (349 mg, 5.31 mmol) and two drops of acetic acid were added and the reaction mixture was stirred at room temperature for 55 h. Additional sodium cyanoborodeuteride (48 mg, 0.663 mmol) and a few drops of acetic acid were added and the reaction mixture was stirred for 7 h at room temperature. The solvent was evaporated under reduced pressure. The residue was mixed with water and $Et_2O$. The biphasic system was acidified to pH 1-2 by the addition of 1N HCl. The layers were separated. The aqueous layer was extracted again with $Et_2O$. The combined organic layers were dried over $MgSO_4$ and the solvent was evaporated under reduced pressure. The residue was dried under vacuum at 50° C. to give racemic 4-(3-((1-(4-chlorophenyl)-1-deuterio-2-oxo-2-(6-(trifluoromethoxy)indolin-1-yl)ethyl)amino)-5-methoxyphenoxy)butanoic acid (Compound 7-D, 242 mg) as a white solid.

The enantiomers of Compound 7-D (242 mg) were separated via preparative SFC (Stationary phase: Kromasil (R,R) Whelk-O1 10/100, mobile phase: $CO_2$, EtOH+0.4% $iPrNH_2$). The product fractions were combined and evaporated under reduced pressure to provide Enantiomer 7A-D as the first eluted product and Enantiomer 7B-D as the second eluted product. Both enantiomers were mixed with in $Et_2O$ and water. The mixture was acidified to pH 1-2 with 1N HCl. The layers were separated and the aqueous layer was extracted twice with $Et_2O$. The combined organic layers were washed with water, dried over $MgSO_4$, filtered, evaporated under reduced pressure and dried under vacuum at 50° C. to give Enantiomer 7A-D (85 mg, 92% deuterated according to $^1$H HMR) and Enantiomer 7B-D (77 mg, 92% deuterated according to $^1$H HMR) as off-white solids.

Enantiomer 7A-D:
$^1$H NMR (360 MHz, DMSO-$d_6$) δ ppm 1.87 (quin, J=7.0 Hz, 2H) 2.34 (t, J=7.1 Hz, 2H) 3.07-3.25 (m, 2H) 3.61 (s, 3H) 3.84 (t, J=6.4 Hz, 2H) 4.05 (td, J=10.3, 7.1 Hz, 1H) 4.52 (td, J=10.3, 6.4 Hz, 1H) 5.76 (t, J=2.0 Hz, 1H) 5.92-5.98 (m, 2H) 6.45 (s, 1H) 7.01 (dd, J=8.1, 1.5 Hz, 1H) 7.33 (d, J=8.1 Hz, 1H) 7.39-7.49 (m, 2H) 7.51-7.60 (m, 2H) 8.03 (s, 1H) 12.17 (br s, 1H)

LC/MS (method LC-C): R$_t$ 1.13 min, MH$^+$ 580

[α]$_D^{20}$: +54.2° (c 0.41, DMF)

Chiral SFC (method SFC-E): R$_t$ 5.51 min, MH$^+$ 580, chiral purity 100%.

Enantiomer 7B-D:

$^1$H NMR (360 MHz, DMSO-d$_6$) δ ppm 1.87 (quin, J=6.9 Hz, 2H) 2.34 (t, J=7.3 Hz, 2H) 3.07-3.25 (m, 2H) 3.61 (s, 3H) 3.84 (t, J=6.6 Hz, 2H) 4.05 (td, J=10.4, 7.3 Hz, 1H) 4.52 (td, J=10.3, 6.4 Hz, 1H) 5.76 (t, J=2.0 Hz, 1H) 5.92-5.98 (m, 2H) 6.45 (s, 1H) 7.01 (dd, J=8.1, 1.5 Hz, 1H) 7.33 (d, J=8.1 Hz, 1H) 7.40-7.49 (m, 2H) 7.51-7.62 (m, 2H) 8.03 (s, 1H) 12.16 (br s, 1H)

LC/MS (method LC-C): R$_t$ 1.10 min, MH$^+$ 580

[α]$_D^{20}$: −50.1° (c 0.459, DMF)

Chiral SFC (method SFC-E): R$_t$ 6.10 min, MH$^+$580, chiral purity 100%.

Example 8: synthesis of 4-(3-((1-(4-chloro-2-(2-hydroxyethoxy)phenyl)-2-oxo-2-(6-(trifluoromethoxy)indolin-1-yl)ethyl)amino)-5-methoxyphenoxy)butanoic Acid (Compound 8)

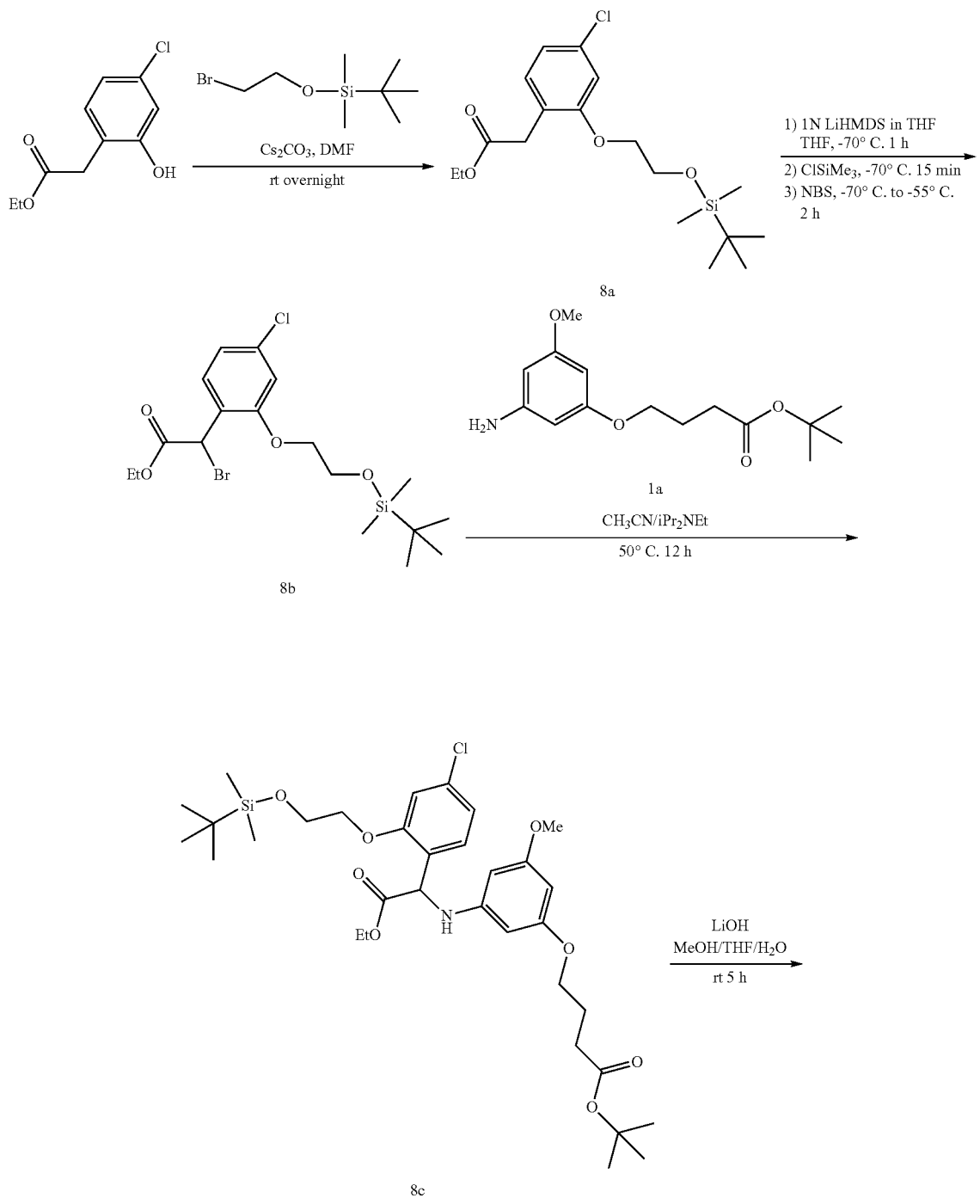

-continued
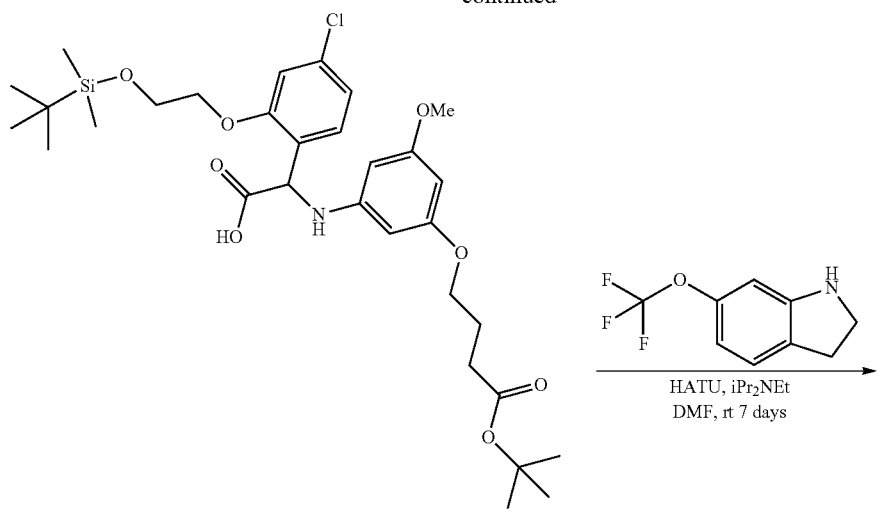
8d
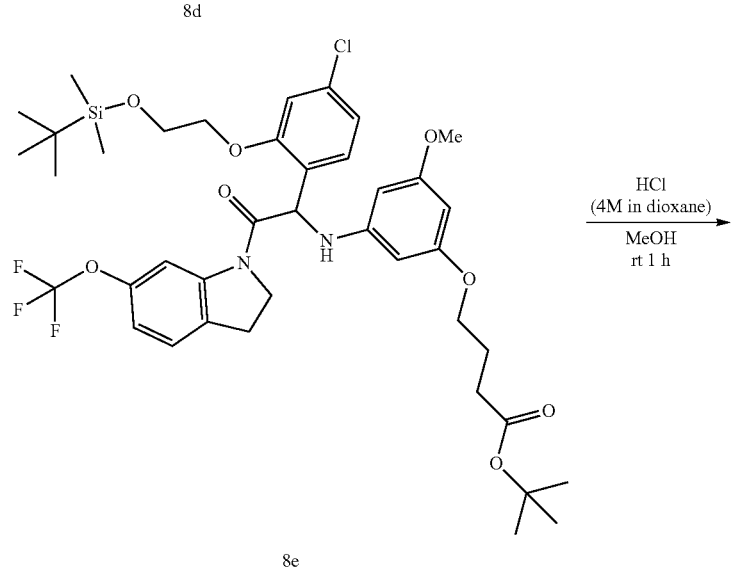
8e
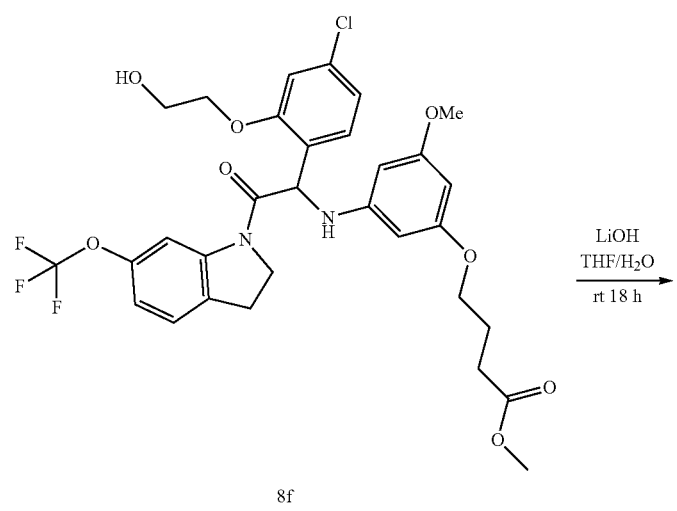
8f

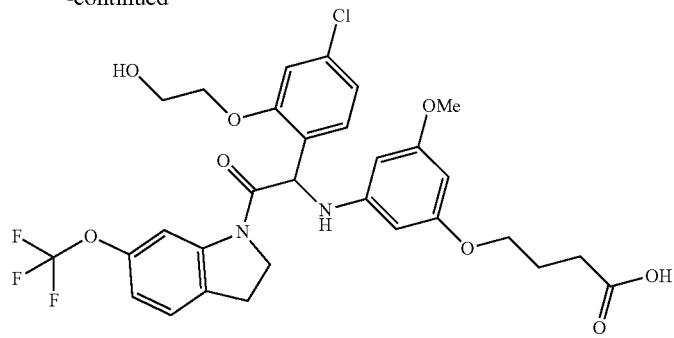

8

Synthesis of Intermediate 8a

To a mixture of ethyl 2-(4-chloro-2-hydroxyphenyl)acetate [CAS 1261826-30-5] (5.2 g, 24.2 mmol) and cesium carbonate (15.8 g, 48.5 mmol) in DMF (90 mL) at 10° C. was added (2-bromoethoxy)(tert-butyl)dimethylsilane [CAS 86864-60-0] (6.26 mL, 29.1 mmol). The reaction mixture was stirred at room temperature overnight. Water was added and the mixture was extracted with EtOAc. The organic phase was dried over MgSO$_4$, filtered and concentrated under reduced pressure. The residue was purified by flash chromatography on silica gel (15-40 µm, 80 g, heptane/EtOAc 80/20). The pure fractions were combined and the solvent was removed under reduced pressure to give ethyl 2-(2-(2-((tert-butyl-dimethylsilyl)oxy)ethoxy)-4-chlorophenyl)acetate 8a (7.8 g).

Synthesis of Intermediate 8b

To a cooled (−70° C.) solution of 1M lithium bis(trimethylsilyl)amide in THF (41.8 mL, 41.8 mmol) was added a solution of ethyl 2-(2-(2-((tert-butyldimethylsilyl)oxy)-ethoxy)-4-chlorophenyl)acetate 8a (7.8 g, 20.9 mmol) in THF (45 mL). After stirring for 1 h at −70° C., chlorotrimethylsilane (4.24 mL, 33.5 mmol) was added. The reaction mixture was stirred at −70° C. for 15 min. N-Bromosuccinimide (4.46 g, 25.1 mmol) in THF (45 mL) was added and stirring was continued at −55° C. for 2 h. The reaction mixture was poured out into H$_2$O and extracted twice with EtOAc. The organic layers were combined, dried over MgSO$_4$, filtered and concentrated under reduced pressure to give ethyl 2-bromo-2-(2-(2-((tert-butyldimethylsilyl)oxy)-ethoxy)-4-chlorophenyl)acetate 8b (10.1 g), which was used in the next step without further purification.

Synthesis of Intermediate 8c

A mixture of ethyl 2-bromo-2-(2-(2-((tert-butyldimethylsilyl)oxy)ethoxy)-4-chlorophenyl)acetate 8b (2.0 g, 4.429 mmol), tert-butyl 4-(3-amino-5-methoxyphenoxy)butanoate 1a (1.62 g, 5.76 mmol) and diisopropylethylamine (1.53 mL, 8.86 mmol) in CH$_3$CN (40 mL) was stirred at 50° C. for 12 h. The reaction mixture was concentrated under reduced pressure. The residue was purified by flash chromatography on silica gel (15-40 µm, 80 g, heptane/EtOAc gradient 85/15 to 60/40). The pure fractions were combined and the solvent was concentrated under reduced pressure to give tert-butyl 4-(3-((1-(2-(2-((tert-butyldimethylsilyl)-oxy)ethoxy)-4-chlorophenyl)-2-ethoxy-2-oxoethyl)amino)-5-methoxyphenoxy)-butanoate 8c (1.1 g).

Synthesis of Intermediate 8d

Lithium hydroxide monohydrate (142 mg, 3.37 mmol) in water (7.5 mL) was added dropwise to a solution of tert-butyl 4-(3-((1-(2-(2-((tert-butyldimethylsilyl)oxy)-ethoxy)-4-chlorophenyl)-2-ethoxy-2-oxoethyl)amino)-5-methoxyphenoxy)butanoate 8c (1.1 g, 1.69 mmol) in THF/CH$_3$OH (1/1) (15 mL) at 10° C. The reaction was stirred at room temperature for 5 h, diluted with water and cooled to 0° C. The solution was slowly acidified to pH 6-7 with 0.5N HCl, and extracted with EtOAc. The organic layer was dried over MgSO$_4$, filtered and the solvent was concentrated under reduced pressure to give 2-((3-(4-(tert-butoxy)-4-oxobutoxy)-5-methoxyphenyl)amino)-2-(2-(2-((tert-butyldimethylsilyl)oxy)ethoxy)-4-chlorophenyl)acetic acid 8d (675 mg). The compound was used without further purification in the next step.

Synthesis of Intermediate 8e

To a solution of 2-((3-(4-(tert-butoxy)-4-oxobutoxy)-5-methoxyphenyl)amino)-2-(2-(2-((tert-butyldimethylsilyl)oxy)ethoxy)-4-chlorophenyl)acetic acid 8d (675 mg, 1.08 mmol) in DMF (6 mL) were added HATU (617 mg, 1.62 mmol), diisopropylethylamine (536 µL, 3.24 mmol) and 6-(trifluoromethoxy)indoline [CAS 959235-95-1] (220 mg, 1.08 mmol). The reaction mixture was stirred at room temperature for 7 days. The reaction mixture was diluted with water. The precipitate was filtered off, washed with water and taken up with EtOAc. The organic layer was washed with a 10% solution of K$_2$CO$_3$ and water, dried over MgSO$_4$, filtered and the solvent was concentrated under reduced pressure to give tert-butyl 4-(3-((1-(2-(2-((tert-butyldimethylsilyl)oxy)ethoxy)-4-chlorophenyl)-2-oxo-2-(6-(trifluoromethoxy)indolin-1-yl)ethyl)amino)-5-methoxyphenoxy)butanoate 8e (385 mg). The compound was used without further purification in the next reaction step.

Synthesis of Intermediate 8f

Under N$_2$ flow at 5° C., HCl (4M in dioxane) (1.19 mL, 4.76 mmol) was added dropwise to a solution of tert-butyl 4-(3-((1-(2-(2-((tert-butyldimethylsilyl)oxy)-ethoxy)-4-chlorophenyl)-2-oxo-2-(6-(trifluoromethoxy)indolin-1-yl) ethyl)amino)-5-methoxyphenoxy)butanoate 8e (385 mg, 0.476 mmol) in MeOH (5 mL). The reaction was stirred at room temperature for 1 h. The mixture was cooled to 0° C., basified with a 10% aqueous solution of K$_2$CO$_3$ and extracted with EtOAc. The organic phase was separated, dried over MgSO₄, filtered and the solvent was concentrated under reduced pressure. The residue was purified by flash chromatography on silica gel (15-40 μm, 24 g, CH₂Cl₂/MeOH 99/1). The pure fractions were combined and the solvent was removed under reduced pressure to give methyl 4-(3-((1-(4-chloro-2-(2-hydroxyethoxy)phenyl)-2-oxo-2-(6-(trifluoromethoxy)indolin-1-yl)ethyl)amino)-5-methoxyphenoxy)butanoate 8f (99 mg).

Synthesis of Compound 8

Lithium hydroxide monohydrate (32 mg, 0.76 mmol) in water (2.5 mL) was added dropwise to a solution of methyl 4-(3-((1-(4-chloro-2-(2-hydroxyethoxy)phenyl)-2-oxo-2-(6-(trifluoromethoxy)indolin-1-yl)ethyl)amino)-5-methoxyphenoxy)butanoate 8f (99 mg, 0.152 mmol) in THF (2.5 mL) at 10° C. The reaction was stirred at room temperature for 18 h, and concentrated under reduced pressure. The residue was purified by flash chromatography on silica gel (20-45 μm, 12 g, CH₂Cl₂/MeOH gradient 99/1 to 90/10). The fractions containing expected compound were combined and the solvent was removed under reduced pressure. A second purification was performed via Reverse phase HPLC (Stationary phase: YMC-actus Triart-C18 10 μm 30×150 mm, mobile phase: gradient from 65% NH₄HCO₃ 0.2%, 35% CH₃CN to 25% NH₄HCO₃ 0.2%, 75% CH₃CN) to give, after freeze drying from a mixture of water/CH₃CN (8/2), 4-(3-((1-(4-chloro-2-(2-hydroxyethoxy)phenyl)-2-oxo-2-(6-(trifluoromethoxy)indolin-1-yl)ethyl)amino)-5-methoxyphenoxy)butanoic acid (Compound 8, 16 mg).

Compound 8:
¹H NMR (500 MHz, DMSO-d₆) δ ppm 1.86 (quin, J=6.86 Hz, 2H) 2.28-2.47 (m, 2H) 3.10-3.27 (m, 2H) 3.61 (s, 3H) 3.68-3.88 (m, 4H) 4.06-4.23 (m, 3H) 4.39 (td, J=10.09, 6.62 Hz, 1H) 5.70-5.76 (m, 2H) 5.91 (br d, J=9.14 Hz, 2H) 6.44 (d, J=8.83 Hz, 1H) 6.99-7.03 (m, 2H) 7.12 (d, J=1.89 Hz, 1H) 7.34 (d, J=8.20 Hz, 2H) 8.02 (s, 1H)

LC/MS (method LC-B): R$_t$ 2.65 min, MH⁺ 639

Example 9: synthesis of 4-(3-((1-(4-chlorophenyl)-2-(5-methoxy-6-(trifluoromethyl)-2,3-dihydro-1H-pyrrolo[3,2-b]pyridin-1-yl)-2-oxoethyl)amino)-5-methoxyphenoxy)butanoic Acid (Compound 9)

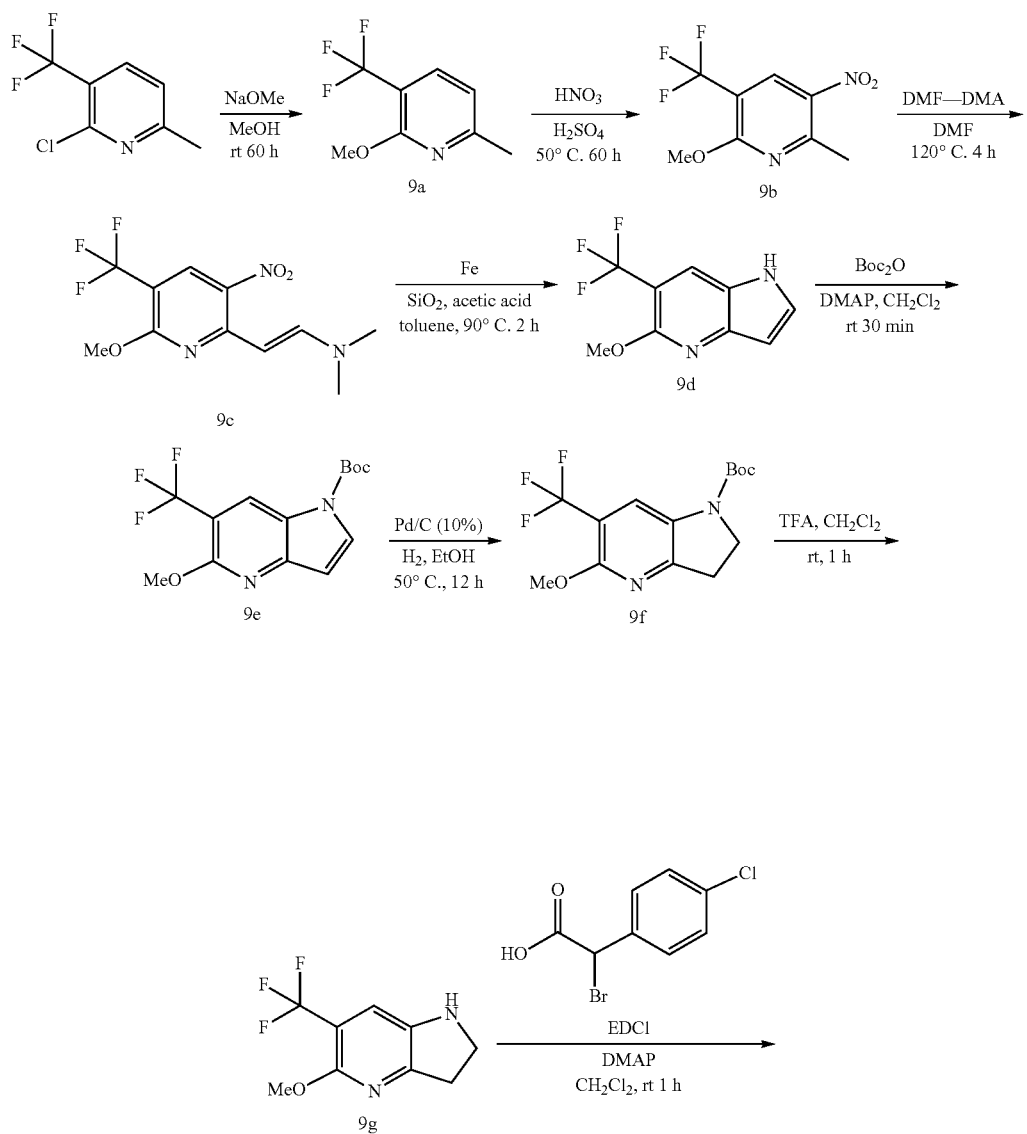

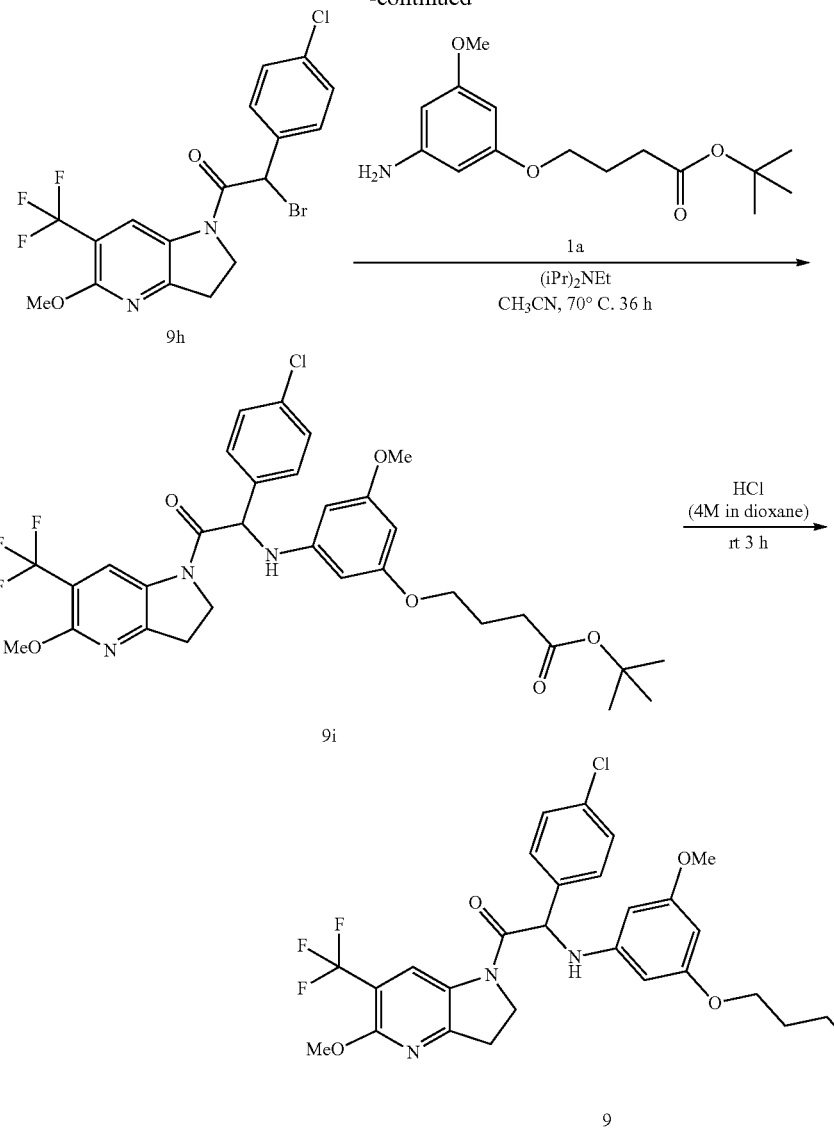

Synthesis of Intermediate 9a

A suspension of 2-chloro-6-methyl-3-(trifluoromethyl)pyridine [CAS 1099597-74-6] (4.8 g, 24.6 mmol in sodium methoxide (25% in MeOH) (24 mL, 105 mmol) was stirred at room temperature for 60 h. The mixture was poured out into ice-water and extracted twice with $Et_2O$. The combined organic layers were dried over $Na_2SO_4$, filtered and concentrated under reduced pressure to give 2-methoxy-6-methyl-3-(trifluoromethyl)pyridine 9a (4.69 g). The product was used as such in the next step.

Synthesis of Intermediate 9b $HNO_3$ (2.32 mL, 49.1 mmol) was added dropwise to a cooled (0° C.) solution of 2-methoxy-6-methyl-3-(trifluoromethyl)pyridine 9a (4.69 g, 24.5 mmol) in $H_2SO_4$ (63.3 mL, 1.128 mol). The reaction mixture was stirred at 50° C. for 60 h. the reaction mixture was poured out carefully into ice-water and the mixture was stirred at 0° C. for 30 min. The solid was filtered off and washed with water to give 2-methoxy-6-methyl-5-nitro-3-(trifluoromethyl)pyridine 9b (4.38 g) as a white solid.

Synthesis of Intermediate 9c 2-methoxy-6-methyl-5-nitro-3-(trifluoromethyl)pyridine 9b (4.38 g, 18.5 mmol) was dissolved in dry DMF (84 mL) under $N_2$ atmosphere. DMF-DMA (12.2 mL, 91.5 mmol) was added and the reaction mixture was heated at 120° C. for 4 h. After cooling to room temperature, the mixture was concentrated under reduced pressure and the solid residue was purified by column chromatography on silica gel (120 g) using a gradient of petroleum ether/EtOAc from 100/0 to 60/40). The pure fractions were combined and the solvent was removed under reduced pressure to give (E)-2-(6-methoxy-3-nitro-5-(trifluoromethyl)pyridin-2-yl)-N,N-dimethylethenamine 9c (4.5 g) as a red solid.

Synthesis of Intermediate 9d (E)-2-(6-methoxy-3-nitro-5-(trifluoromethyl)pyridin-2-yl)-N,N-dimethylethenamine 9c (4.5 g, 15.5 mmol) was dissolved in toluene (87 mL) under $N_2$ atmosphere. Silica gel (4.64 g), iron powder (8.63 g, 154.5 mmol) and acetic acid (35.4 mL) were added and the reaction mixture was stirred at 90° C. for 2 h. The reaction mixture was filtered over Celite® and the solid was rinsed several times with EtOAc. The combined filtrates were evaporated and the residue was purified by column chromatography on silica gel (petroleum ether/EtOAc gradient 100/0 to 65/35) to give 5-methoxy-6-(trifluoromethyl)-1H-pyrrolo[3,2-b]pyridine 9d (3.1 g) as a yellow solid.

Synthesis of Intermediate 9e 5-methoxy-6-(trifluoromethyl)-1H-pyrrolo[3,2-b]pyridine 9d (2.04 g, 9.44 mmol) was dissolved in dry $CH_2Cl_2$ (90 mL) under $N_2$ atmosphere. DMAP (123 mg, 1.01 mmol) and $Boc_2O$ (2.49 g, 11.4 mmol) were added. The reaction mixture was stirred for 30 min at room temperature, concentrated under reduced pressure and the residue was purified by flash column chromatography on silica gel (petroleum ether/EtOAc gradient 100/0 to 96/4) to give tert-butyl 5-methoxy-6-(trifluoromethyl)-1H-pyrrolo[3,2-b]pyridine-1-carboxylate 9e (2.95 g) as a white solid.

Synthesis of Intermediate 9f tert-butyl 5-methoxy-6-(trifluoromethyl)-1H-pyrrolo[3,2-b]pyridine-1-carboxylate 9e (1.45 g, 4.59 mmol) was dissolved in EtOH (30 mL) and the reaction was purged with nitrogen. Pd/C (10%) (976 mg, 0.917 mmol) was added to the reaction mixture was hydrogenated overnight at 50° C. The reaction mixture was cooled down to room temperature and filtered over Celite®. The filter cake was washed with EtOH and the filtrate was concentrated under reduced pressure. The residue was purified by flash column chromatography (petroleum ether/EtOAc gradient 100/0 to 95/5) to give tert-butyl 5-methoxy-6-(trifluoromethyl)-2,3-dihydro-1H-pyrrolo[3,2-b]pyridine-1-carboxylate 9f (1.2 g) as a white solid.

Synthesis of Intermediate 9g

A solution of tert-butyl 5-methoxy-6-(trifluoromethyl)-2,3-dihydro-1H-pyrrolo[3,2-b]pyridine-1-carboxylate 9f (1.2 g, 3.77 mmol) in $TFA/CH_2Cl_2$ (1/1) (19 mL) was stirred at room temperature for 1 h. The reaction mixture was diluted with $CH_2Cl_2$ (60 mL), washed with a saturated aqueous $Na_2CO_3$ solution (60 mL) and brine (60 mL). The organic layer was dried over $Na_2SO_4$, filtered and concentrated under reduced pressure. The residue was purified by flash column chromatography on silica gel (40 g, petroleum ether/EtOAc gradient 80/20 to 40/60) to give 5-methoxy-6-(trifluoromethyl)-2,3-dihydro-1H-pyrrolo[3,2-b]pyridine 9g (745 mg) as a yellow solid.

Synthesis of Intermediate 9h 5-methoxy-6-(trifluoromethyl)-2,3-dihydro-1H-pyrrolo[3,2-b]pyridine 9g (350 mg, 1.60 mmol) was dissolved in dry $CH_2Cl_2$ (6.5 mL) under $N_2$ atmosphere. DMAP (28 mg, 0.229 mmol) and 2-bromo-2-(4-chlorophenyl)acetic acid [CAS 3381-73-5] (460 mg, 1.84 mmol) were added. EDCl (383 mg, 1.998 mmol) was added and the reaction mixture was stirred at room temperature for 1 h. The reaction mixture was diluted with $CH_2Cl_2$, cooled to 0° C. and a saturated aqueous solution of $K_2CO_3$ was added. The layers were separated and the organic layer was washed with brine, dried over $Na_2SO_4$ and concentrated under reduced pressure. The residue was purified by flash column chromatography on silica gel (40 g, petroleum ether/EtOAc gradient 100/0 to 60/40). A second purification was performed on silica gel (40 g, toluene/$Et_2O$ gradient 100/0 to 90/10). A third purification was performed (12 g, toluene/$Et_2O$ gradient 98/2 to 97/3). The pure fractions were combined and concentrated under reduced pressure to give 2-bromo-2-(4-chlorophenyl)-1-(5-methoxy-6-(trifluoromethyl)-2,3-dihydro-1H-pyrrolo[3,2-b]pyridin-1-yl)ethanone 9h (407 mg) as pale green foam.

Synthesis of Intermediate 9i 2-bromo-2-(4-chlorophenyl)-1-(5-methoxy-6-(trifluoromethyl)-2,3-dihydro-1H-pyrrolo[3,2-b]pyridin-1-yl)ethanone 9h (400 mg, 0.89 mmol) and tert-butyl 4-(3-amino-5-methoxyphenoxy)butanoate 1a (300 mg, 1.07 mmol) were dissolved in dry $CH_3CN$ (40 mL) under $N_2$ atmosphere. Diisopropylethylamine (232 µL, 1.33 mmol) was added and the reaction mixture was heated to 70° C. for 36 h. The reaction mixture was diluted with 20 mL of EtOAc, and washed with 1M HCl and brine. The organic layer was dried over $Na_2SO_4$, filtered and concentrated under reduced pressure. The residue was purified by flash column chromatography on silica gel (40 g, toluene/EtOAc gradient 100/0 to 94/6). A second purification was performed by column chromatography on silica gel (2×12 g, petroleum ether/acetone gradient 100/0 to 95/5). The pure fractions were combined and concentrated under reduced pressure to give tert-butyl 4-(3-((1-(4-chlorophenyl)-2-(5-methoxy-6-(trifluoromethyl)-2,3-dihydro-1H-pyrrolo[3,2-b]pyridin-1-yl)-2-oxoethyl)amino)-5-methoxyphenoxy)butanoate 9i (341 mg) as white foam.

Synthesis of Compound 9

Tert-butyl 4-(3-((1-(4-chlorophenyl)-2-(5-methoxy-6-(trifluoromethyl)-2,3-dihydro-1H-pyrrolo[3,2-b]pyridin-1-yl)-2-oxoethyl)amino)-5-methoxyphenoxy)butanoate 9i (341 mg, 0.525 mmol) was dissolved under $N_2$ atmosphere in HCl (4M in dioxane) (6.62 mL). The reaction was stirred at room temperature for 3 h. The mixture was concentrated under reduced pressure. The residue was purified by flash column chromatography on silica gel (40 g, toluene/EtOAc/AcOH gradient 99/0/1 to 50/49/1). A second purification was performed on silica gel (2×12 g, $CH_2Cl_2$/MeOH/AcOH gradient 99/0/1 to 96/3/1). A third purification was performed on silica gel (12 g, $CH_2Cl_2$/MeOH/AcOH gradient 98/1/1 to 96.5/2.5/1). The pure fractions were combined and concentrated under reduced pressure to give 4-(3-((1-(4-chlorophenyl)-2-(5-methoxy-6-(trifluoromethyl)-2,3-dihydro-1H-pyrrolo[3,2-b]pyridin-1-yl)-2-oxoethyl)amino)-5-methoxyphenoxy)butanoic acid (compound 9, 72 mg) as white solid.

Compound 9:

$^1H$ NMR (500 MHz, DMSO-de) δ ppm 1.84-1.91 (m, 2H) 2.30-2.37 (m, 2H) 3.21-3.30 (m, 2H) 3.62 (s, 3H) 3.80-3.89 (m, 2H) 3.94 (s, 3H) 3.98-4.12 (m, 1H) 4.56 (td, J=10.64, 6.15 Hz, 1H) 5.58 (d, J=8.83 Hz, 1H) 5.76 (t, J=1.89 Hz, 1H) 5.95 (br d, J=10.72 Hz, 2H) 6.40 (d, J=8.83 Hz, 1H) 7.44 (d, J=8.51 Hz, 2H) 7.56 (d, J=8.51 Hz, 2H) 8.53 (s, 1H) 12.06-12.26 (m, 1H)

LC/MS (method LC-A): $R_t$ 2.87 min, $MH^+$ 594

Example 10: synthesis of 4-(3-((1-(4-chlorophenyl)-2-oxo-2-(2-(trifluoromethyl)-5,6-dihydro-4H-thieno[3,2-b]pyrrol-4-yl)ethyl)amino)-5-methoxyphenoxy)butanoic Acid (Compound 10) and Chiral Separation into Enantiomers 10A and 10B
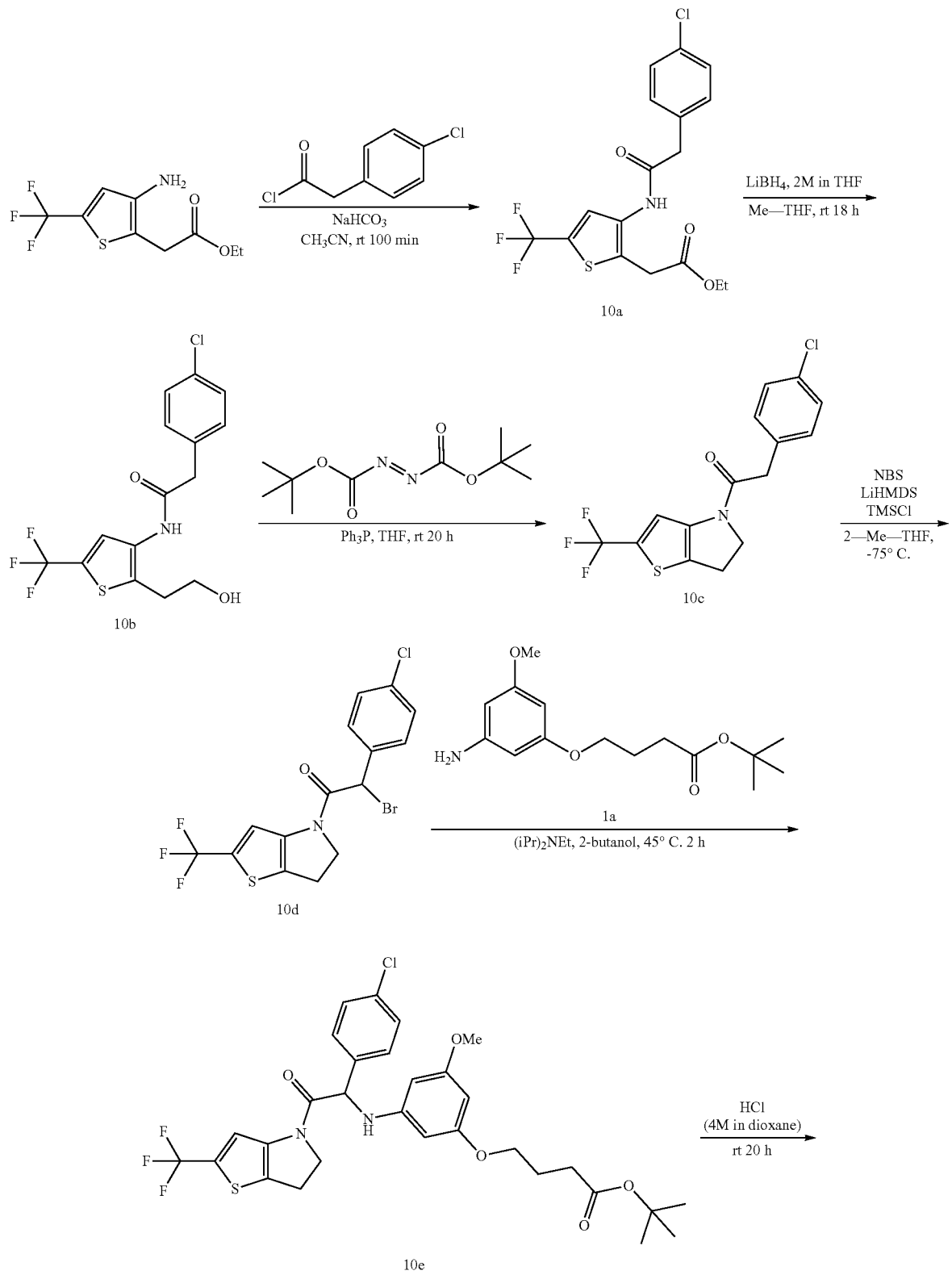

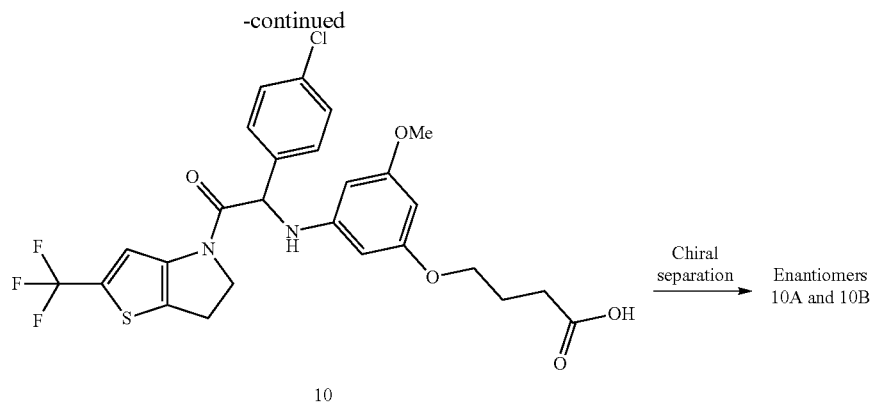

10

Synthesis of Intermediate 10a

A solution of ethyl 2-(3-amino-5-(trifluoromethyl)thiophen-2-yl)acetate ([CAS 860398-39-6] (1.49 g, 5.88 mmol) in $CH_3CN$ (40 mL) was stirred at room temperature under $N_2$-atmosphere. $NaHCO_3$ (0.544 g, 6.47 mmol) and 2-(4-chlorophenyl)acetyl chloride ([CAS 25026-34-0] (861 μL, 5.88 mmol) were added, and the reaction mixture was stirred at room temperature for 100 min. The mixture was poured out into stirring $H_2O$ (200 mL) and extracted with $Et_2O$ (2×100 mL). The combined organic layers were washed with brine, dried over $MgSO_4$, filtered and evaporated under reduced pressure. The residue was purified by flash chromatography on silica gel (50 g) using a gradient of heptane/EtOAc 100/0 to 80/20. The desired fractions were combined, evaporated under reduced pressure and co-evaporated with toluene to provide ethyl 2-(3-(2-(4-chlorophenyl)acetamido)-5-(trifluoromethyl)thiophen-2-yl)acetate 10a (1.15 g).

Synthesis of Intermediate 10b

A solution of $LiBH_4$ 2 M in THF (2.59 mL, 5.18 mmol) was added slowly to a stirring solution of ethyl 2-(3-(2-(4-chlorophenyl)acetamido)-5-(trifluoromethyl)thiophen-2-yl)acetate 10a (1.05 g, 2.59 mmol) in 2-Me-THF (20 mL). The reaction mixture was stirred at room temperature for 18 h. The mixture was poured out into a stirring mixture of $H_2O$ (100 mL) and $Et_2O$ (100 mL). 1N HCl (10 mL) was added dropwise (foaming), and after stirring for 15 minutes, the layers were separated. The organic layer was washed with brine, dried over $MgSO_4$, filtered, and evaporated under reduced pressure. The residue was purified by flash chromatography on silica gel (25 g) using a gradient of heptane/iPrOH 100/0 to 50/50. The desired fractions were combined, evaporated under reduced pressure, and co-evaporated with toluene. The residue was stirred up in toluene (6 mL) at 45° C. for 15 minutes, filtered off at room temperature, washed with toluene (3×), and dried under vacuum at 50° C. to provide 2-(4-chlorophenyl)-N-(2-(2-hydroxyethyl)-5-(trifluoromethyl)thiophen-3-yl)acetamide 10b (1.15 g).

Synthesis of Intermediate 10c

Triphenylphosphine (1.02 g, 3.85 mmol) was added to a stirring solution of 2-(4-chlorophenyl)-N-(2-(2-hydroxyethyl)-5-(trifluoromethyl)thiophen-3-yl)acetamide 10b (1.0 g, 2.75 mmol) in THF (20 mL) under $N_2$-atmosphere. Di-tert-butyl azodicarboxylate (0.71 g, 3.02 mmol) was added and the resulting solution was stirred at room temperature for 20 h. The volatiles were evaporated under reduced pressure and the residue was purified by flash chromatography on silica gel (25 g) using a gradient of $CH_2Cl_2$/heptane 0/100 to 100/0. The desired fractions were combined and concentrated under reduced pressure to a residual volume of 15 mL. The product was allowed to crystallize over a period of 4 days. The solids were filtered off, washed with heptane (4×) and dried under vacuum at 50° C. to provide 2-(4-chlorophenyl)-1-(2-(trifluoromethyl)-5,6-dihydro-4H-thieno[3,2-b]pyrrol-4-yl)ethanone 10c (0.75 g).

Synthesis of Intermediate 10d

At −75° C., under a $N_2$ flow, LiHMDS 1M in THF (4.34 mL, 4.34 mmol) was added dropwise to a mixture of 2-(4-chlorophenyl)-1-(2-(trifluoromethyl)-5,6-dihydro-4H-thieno[3,2-b]pyrrol-4-yl)ethanone 10c (750 mg, 2.17 mmol) in 2-Me-THF (30 mL) and the mixture was kept at −75° C. for 20 min. TMSCl (444 μL, 3.47 mmol) was added dropwise. The mixture was stirred for 20 min at −75° C. and a solution of N-bromosuccinimide (502 mg, 2.82 mmol) in THF (5 mL) was added dropwise. After stirring for 20 min at −75° C., the reaction was quenched with a saturated aqueous solution of $NH_4Cl$ (25 mL). The cooling bath was removed and the reaction mixture was stirred until the reaction temperature reached −15° C. Water (25 mL) and DIPE (25 mL) were added and the mixture was stirred for 10 min. The organic layer was separated and the aqueous phase was extracted with $Et_2O$. The combined organic layers were dried over $MgSO_4$, filtered and the solvent was evaporated under reduced pressure to give 2-bromo-2-(4-chlorophenyl)-1-(2-(trifluoromethyl)-5,6-dihydro-4H-thieno[3,2-b]pyrrol-4-yl)ethanone 10d (921 mg), which was used as such in the next step.

Synthesis of Intermediate 10e

A mixture of 2-bromo-2-(4-chlorophenyl)-1-(2-(trifluoromethyl)-5,6-dihydro-4H-thieno[3,2-b]pyrrol-4-yl)ethanone 10d (921 mg, 2.17 mmol), tert-butyl 4-(3-amino-5-methoxyphenoxy)butanoate 1a (1.22 g, 4.34 mmol) and diisopropylethylamine (747 μL, 4.34 mmol) in 2-butanol (15 mL) was stirred at 45° C. for 2 h. The reaction mixture was allowed to reach room temperature, and poured out into stirring water (50 mL). The product was extracted (2×) with $Et_2O$. The combined organic layers were dried over $MgSO_4$, filtered, and the solvent was evaporated under reduced pressure and co-evaporated with dioxane (2×). The residue was purified by flash chromatography on silica gel (40 g) using a gradient of heptane/EtOAc/EtOH 100/0/0 to 40/45/15. The desired fractions were combined, evaporated under reduced pressure, and co-evaporated with dioxane (2×) to provide tert-butyl 4-(3-((1-(4-chlorophenyl)-2-oxo-2-(2-(trifluoromethyl)-5,6-dihydro-4H-thieno[3,2-b]pyrrol-4-yl)ethyl)amino)-5-methoxyphenoxy)butanoate 10e (1.36 g), which was used as such in the next step.

Synthesis of Compound 10 and Chiral Separation into Enantiomers 10A and 10B tert-Butyl 4-(3-((1-(4-chlorophenyl)-2-oxo-2-(2-(trifluoromethyl)-5,6-dihydro-4H-thieno[3,2-b]pyrrol-4-yl)ethyl)amino)-5-methoxyphenoxy)butanoate 10e (1.36 g, 2.17 mmol), was mixed with 4M HCl in dioxane (15 mL) and the mixture was stirred at room temperature for 20 h. The solids were filtered off, washed with dioxane (3×), and dried under vacuum at 50° C. The residue (1.4 g) was purified via preparative HPLC (Stationary phase: RP XBridge® Prep C18 OBD—10 µm, 50×150 mm, mobile phase: 0.25% NH$_4$HCO$_3$ solution in water, CH$_3$CN). The desired fractions were combined and the organic volatiles were evaporated under reduced pressure. The remaining aqueous solution was extracted (2×) with a solvent mixture of Et$_2$O/2-MeTHF (2/1). The combined organic layers were washed with brine, dried over MgSO$_4$, filtered, and evaporated under reduced pressure to provide crude 4-(3-((1-(4-chlorophenyl)-2-oxo-2-(2-(trifluoromethyl)-5,6-dihydro-4H-thieno[3,2-b]pyrrol-4-yl)ethyl)amino)-5-methoxyphenoxy)butanoic acid (Compound 10, 0.54 g). An analytical sample (40 mg) was dissolved in stirring Et$_2$O (1 mL) and 4M HCl in dioxane (250 µL) was added. After stirring for 2 min, the product was filtered off, washed (3×) with Et$_2$O/dioxane (4/1), and dried under vacuum at 50° C. to provide Compound 10 (20 mg).

The enantiomers of Compound 10 (500 mg) were separated via preparative chiral SFC (Stationary phase: Chiralpak® Diacel IC 20×250 mm, mobile phase: CO$_2$, EtOH). The product fractions of the first eluted enantiomer were combined, evaporated under reduced pressure and purified by flash chromatography on silica gel (12 g) using a gradient of heptane/EtOAc:EtOH:AcOH 100/0:0:0 to 60/30:9.8:0.2. The desired fractions were combined, evaporated under reduced pressure and co-evaporated with DCM. The residue was dried under vacuum at 50° C. to provide Enantiomer 10A (164 mg). The product fractions of the second eluted enantiomer were combined, evaporated under reduced pressure and purified by flash chromatography on silica gel (12 g) using a gradient of heptane/EtOAc:EtOH:AcOH 100/0:0:0 to 60/30:9.8:0.2. The desired fractions were combined, evaporated under reduced pressure and co-evaporated with DCM. The residue was dried under vacuum at 50° C. to provide Enantiomer 10B (167 mg).

Compound 10:
$^1$H NMR (360 MHz, DMSO-d) δ ppm 1.87 (t, J=6.8 Hz, 2H), 2.31-2.37 (m, 2H), 3.26-3.38 (m, 2H), 3.62 (s, 3H), 3.84 (br t, J=6.4 Hz, 2H), 4.29 (td, J=10.5, 6.8 Hz, 1H), 4.79 (td, J=10.2, 6.2 Hz, 1H), 5.49 (s, 1H), 5.76 (t, J=2.0 Hz, 1H), 5.91-5.97 (m, 2H), 7.44 (d, J=8.4 Hz, 2H), 7.54 (d, J=8.8 Hz, 2H), 7.76 (s, 1H)

LC/MS (method LC-D): R$_t$ 1.93 min, MH$^+$ 569

Enantiomer 10A:
$^1$H NMR (400 MHz, DMSO-d$_6$) δ ppm 1.83-1.91 (m, 2H), 2.30-2.36 (m, 2H), 3.23-3.30 (m, 2H), 3.62 (br s, 3H), 3.85 (br s, 2H), 4.30 (m, J=9.5 Hz, 1H), 4.79 (m, J=6.8 Hz, 1H), 5.48 (br d, J=8.8 Hz, 1H), 5.76 (br s, 1H), 5.94 (br d, J=9.0 Hz, 2H), 6.35 (br d, J=8.1 Hz, 1H), 7.43 (br d, J=7.3 Hz, 2H), 7.54 (br d, J=8.1 Hz, 2H), 7.76 (br s, 1H), 12.10 (br s, 1H)

LC/MS (method LC-C): R$_t$ 1.03 min, MH$^+$ 569

[α]$_D^{20}$: +36.9° (c 0.4445, DMF)

Chiral SFC (method SFC-F): R$_t$ 5.52 min, MH$^+$569 chiral purity 100%.

Enantiomer 10B:
$^1$H NMR (400 MHz, DMSO-d$_6$) δ ppm 1.83-1.91 (m, 2H), 2.34 (br t, J=6.8 Hz, 2H), 3.23-3.30 (m, 2H), 3.62 (s, 3H), 3.85 (br t, J=5.9 Hz, 2H), 4.25-4.35 (m, 1H), 4.75-4.83 (m, 1H), 5.48 (br d, J=8.4 Hz, 1H), 5.76 (br s, 1H), 5.94 (br d, J=8.8 Hz, 2H), 6.35 (br d, J=8.4 Hz, 1H), 7.43 (br d, J=7.7 Hz, 2H), 7.54 (br d, J=7.9 Hz, 2H), 7.76 (s, 1H), 12.11 (br s, 1H)

LC/MS (method LC-C): R$_t$ 1.03 min, MH$^+$ 569

[α]$_D^{20}$: −39.1° (c 0.437, DMF)

Chiral SFC (method SFC-F): R$_t$ 6.98 min, MH$^+$569 chiral purity 97%.

Example 11: Synthesis of 4-(3-((1-(4-chlorophenyl)-2-oxo-2-(6-((trifluoromethyl)thio)indolin-1-yl)ethyl)amino)-5-methoxyphenoxy)butanoic Acid (Compound 11)

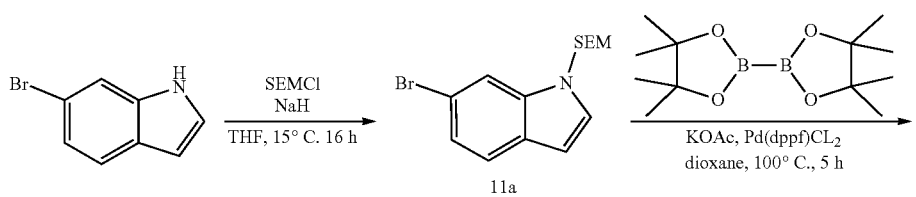

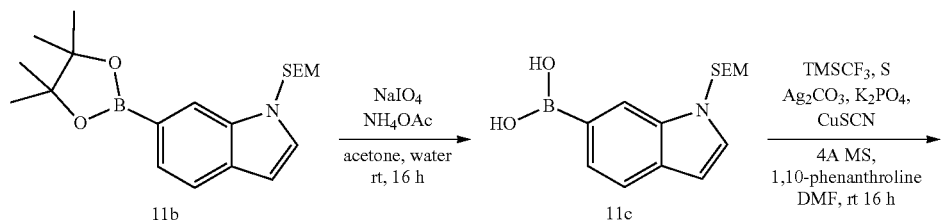

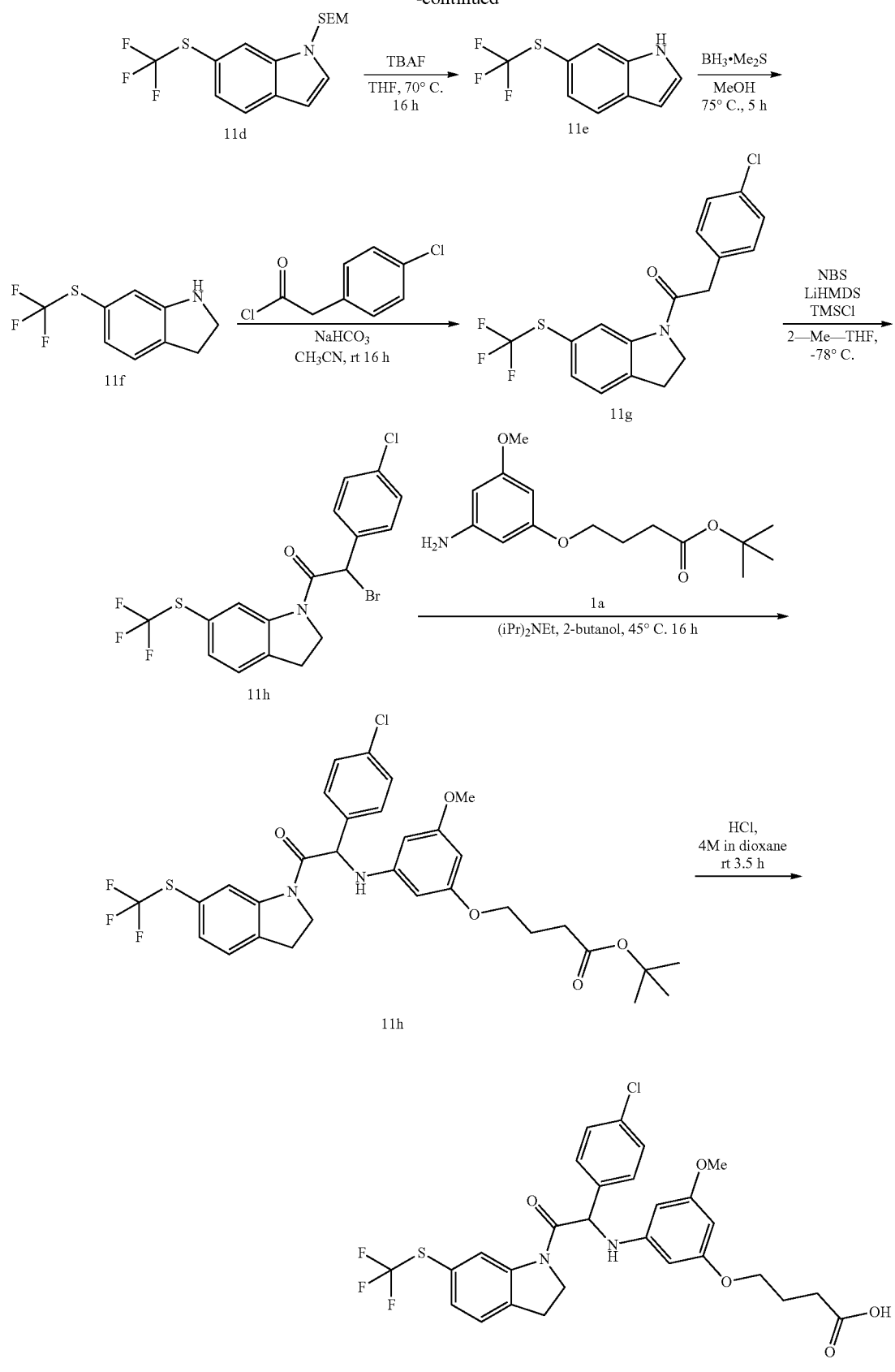

Synthesis of Intermediate 11a

To the suspension of NaH (26.5 g, 663 mmol, 60% in oil) in THF (100 mL) at 0° C. was added 6-bromo-1H-indole [CAS 52415-29-9] (100 g, 510 mmol) in portions. The reaction was stirred for 30 min at 15° C. After cooling to 0° C., SEMCl (93.6 g, 561 mmol, 99.5 mL) was added. The reaction mixture was stirred for 16 h at 15° C. and poured out into a saturated aqueous ammonium chloride solution (200 mL). The mixture was diluted with ethyl acetate (300 mL). The layers were separated and the aqueous layer was extracted with ethyl acetate (2×200 mL). The combined organic layers were washed with brine (500 mL), dried over $Na_2SO_4$, filtered and concentrated in vacuo. The residue was purified by column chromatography on silica gel using petroleum ether. The product fractions were combined and evaporated under reduced pressure to afford 6-bromo-1-((2-(trimethylsilyl)ethoxy)methyl)-1H-indole 11a (134 g) as a yellow oil.

Synthesis of Intermediate 11b

A mixture of 6-bromo-1-((2-(trimethylsilyl)ethoxy)methyl)-1H-indole 11a (134 g, 411 mmol), 4,4,4',4',5,5,5',5'-octamethyl-2,2'-bi(1,3,2-dioxaborolane) (158.5 g, 624 mmol), Pd(dppf)Cl$_2$ (15.02 g, 20.5 mmol) and KOAc (161.2 g, 1.64 mol) in 1,4-dioxane (1.5 L) was stirred at 100° C. for 5 h under N$_2$-atmosphere. The reaction was cooled to 25° C. and filtered through a pad of Celite®. The solvent was evaporated under reduced pressure and the residue was purified by column chromatography on silica gel (petroleum ether/ethyl acetate gradient 100/0 to 50/1). The product fractions were combined and evaporated under reduced pressure to afford 6-(4,4,5,5-tetramethyl-1,3,2-dioxaborolan-2-yl)-1-((2-(trimethylsilyl)ethoxy)methyl)-1H-indole 11b (104 g) as a light yellow oil.

Synthesis of Intermediate 11c

To a solution of 6-(4,4,5,5-tetramethyl-1,3,2-dioxaborolan-2-yl)-1-((2-(trimethylsilyl)ethoxy)methyl)-1H-indole 11b (52 g, 139 mmol) in acetone (2.4 L) and H$_2$O (2.4 L) were added NaIO$_4$ (119 g, 557 mmol) and NH$_4$OAc (53.7 g, 696 mmol). The reaction mixture was stirred at 25° C. for 16 hours. The reaction was duplicated at the same scale (52 g of compound 11b) and the reaction mixtures of both reactions were combined for the work-up. The precipitate was filtered off and the solvent (acetone) was removed under reduced pressure. Ethyl acetate (5 L) was added and the organic layer was separated. The aqueous layer was extracted with ethyl acetate (3×5 L). The combined organic layers were dried over Na$_2$SO$_4$, filtered and concentrated in vacuo to afford (1-((2-(trimethylsilyl)ethoxy)methyl)-1H-indol-6-yl)boronic acid 11c (85 g) as a black brown solid which was used into the next step without further purification.

Synthesis of Intermediate 11d

A mixture of TMSCF$_3$ (207.5 g, 1.46 mol), CuSCN (10.7 g, 87.6 mmol), S$_8$ (224.6 g, 875.6 mmol), (1-((2-(trimethylsilyl)ethoxy)methyl)-1H-indol-6-yl)boronic acid 11c (85 g, 292 mmol), Ag$_2$CO$_3$ (161 g, 584 mmol), K$_3$PO$_4$ (186 g, 876 mmol), 1,10-phenanthroline (31.6 g, 175 mmol) and 4A molecular sieves (85 g) in DMF (1 L) was stirred at 25° C. for 16 hours under N$_2$-atmosphere. The reaction mixture was filtered through a pad Celite®. The filtrate was diluted with MTBE (1 L), washed with water (3×500 mL), dried over Na$_2$SO$_4$, filtered and concentrated under reduced pressure. The residue was purified by column chromatography on silica gel (petroleum ether/ethyl acetate 100/1). The product fractions were combined and evaporated under reduced pressure to afford 6-((trifluoromethyl)thio)-1-((2-(trimethylsilyl)ethoxy)methyl)-1H-indole 11d (38 g) as an light yellow oil.

Synthesis of Intermediate 11e

To the solution of 6-((trifluoromethyl)thio)-1-((2-(trimethylsilyl)ethoxy)methyl)-1H-indole 11d (38 g, 109 mmol) in THF (1.5 L) were added TBAF.3H$_2$O (345 g, 1.09 mol) and ethane-1,2-diamine (131.45 g, 2.19 mol). The reaction mixture was stirred at 70° C. for 16 h. The reaction mixture was cooled to 25° C. and poured out into saturated aqueous NaHCO$_3$ (3 L). The aqueous mixture was extracted with ethyl acetate (3×1 L). The combined organic layers were dried over Na$_2$SO$_4$, filtered and concentrated under reduced pressure. The residue was purified by preparative HPLC (column: Phenomenex Gemini C18 250×50 mm 10 μm, mobile phase: water (0.05% ammonia hydroxide v/v), CH$_3$CN) to give 6-((trifluoromethyl)thio)-1H-indole 11e (10.1 g) as an off-white solid.

Synthesis of Intermediate 11f

A mixture of 6-((trifluoromethyl)thio)-1H-indole 11e (1.0 g, 4.6 mmol) and borane dimethyl sulfide complex (7 mL) was heated in a sealed tube at 75° C. for 5 h. The reaction mixture was allowed to reach room temperature and added dropwise to stirring MeOH (30 mL) (exothermic). After addition, the resulting solution was heated under reflux for 3 h. The solvent were evaporated under reduced pressure and the residue was purified by flash chromatography on silica gel (25 g) using a gradient of heptane/CH$_2$Cl$_2$ 100/0 to 40/60. The desired fractions were combined, evaporated under reduced pressure, and co-evaporated with dioxane. The product was dried under vacuum at 50° C. to provide 6-((trifluoromethyl)thio)indoline 11f (0.79 g).

Synthesis of Intermediate 11g

A solution of 6-((trifluoromethyl)thio)indoline 11f (0.79 g, 3.6 mmol) in CH$_3$CN (30 mL) was stirred under N$_2$-atmosphere. NaHCO$_3$ (0.333 g, 3.96 mmol) was added and the reaction mixture was cooled on an ice-bath. A solution of 2-(4-chlorophenyl)acetyl chloride ([CAS 25026-34-0] (0.852 g, 4.51 mmol) in CH$_3$CN (20 mL) was added, and the reaction mixture was stirred at room temperature for 16 h. The mixture was poured out into stirring H$_2$O (100 mL). The precipitate was filtered off and washed with water (4×10 mL). The solids were stirred up in Et$_2$O/heptane (3/2) (20 mL), filtered off, washed with Et$_2$O/heptane (3/2) (2×10 mL) and dried under vacuum at 50° C. to provide 2-(4-chlorophenyl)-1-(6-((trifluoromethyl)thio)indolin-1-yl)ethanone 11g (1.033 g).

Synthesis of Intermediate 11h

At −78° C., under a N$_2$ flow, LiHMDS 1M in THF (5.56 mL, 5.56 mmol) was added dropwise to a mixture of 2-(4-chlorophenyl)-1-(6-((trifluoromethyl)thio)indolin-1-yl)ethanone 11g (1.033 mg, 2.78 mmol) in 2-Me-THF (40 mL) and the mixture was kept at −78° C. for 20 min. TMSCl (568 μL, 4.45 mmol) was added dropwise. The mixture was stirred for 35 min at −78° C. and a solution of N-bromosuccinimide (643 mg, 3.61 mmol) in THF (8 mL) was added dropwise. After stirring for 35 min at −78° C., the reaction was quenched with a saturated aqueous solution of NH$_4$Cl (30 mL). The cooling bath was removed and the reaction mixture was stirred until the reaction reached room temperature. Water (30 mL) and DIPE (30 mL) were added and the mixture was stirred for 20 min. The organic layer was separated, washed with brine, dried over MgSO$_4$, filtered and the solvent was evaporated under reduced pressure to give 2-bromo-2-(4-chlorophenyl)-1-(6-((trifluoromethyl)thio)indolin-1-yl)ethanone 11h (1.25 g), which was used as such in the next step.

Synthesis of Intermediate 11i

A mixture of 2-bromo-2-(4-chlorophenyl)-1-(6-((trifluoromethyl)thio)indolin-1-yl)ethanone 11h (1.25 mg, 2.78 mmol), tert-butyl 4-(3-amino-5-methoxyphenoxy)butanoate 1a (1.56 g, 5.56 mmol) and diisopropylethylamine (957 µL, 5.56 mmol) in 2-butanol (25 mL) was stirred at 45° C. for 16 h. The reaction mixture was allowed to reach room temperature, and poured out into stirring water (100 mL). The product was extracted (2×) with CH$_2$Cl$_2$. The combined organic layers were washed with brine, dried over MgSO$_4$, filtered, and the solvent was evaporated under reduced pressure. The residue was purified by flash chromatography on silica gel (40 g) using a gradient of heptane/EtOAc/EtOH 100/0/0 to 70/20/10. The desired fractions were combined and evaporated under reduced pressure to provide tert-butyl 4-(3-((1-(4-chlorophenyl)-2-oxo-2-(6-((trifluoromethyl)thio)indolin-1-yl)ethyl)amino)-5-methoxyphenoxy)butanoate 11i (2.0 g), which was used as such in the next step.

Synthesis of Compound 11 tert-Butyl 4-(3-((1-(4-chlorophenyl)-2-oxo-2-(6-((trifluoromethyl)thio)indolin-1-yl)ethyl)amino)-5-methoxyphenoxy)butanoate 11i (1.81 g, 2.78 mmol), was mixed with 4M HCl in dioxane (20 mL) and the mixture was stirred at room temperature for 3.5 h. The solids were filtered off, washed with dioxane (3×) and Et$_2$O (20 mL). The solid was dissolved in CH$_2$Cl$_2$ (100 mL) and mixed with water (50 mL) and saturated aqueous Na$_2$CO$_3$ (30 mL). After stirring for 15 min, the layers were separated. The organic layer was washed with brine, dried over MgSO$_4$, filtered and evaporated under reduced pressure. The residue was purified via preparative HPLC (Stationary phase: RP XBridge® Prep C18 OBD—10 µm, 30×150 mm, mobile phase: 0.25% NH$_4$HCO$_3$ solution in water, CH$_3$CN). CH$_3$CN was evaporated and the residual aqueous solution was acidified to pH 3 with 1N HCl. The product was extracted with EtOAc (100 mL). The organic layer was washed with brine (50 mL), dried over MgSO$_4$, filtered, evaporated under reduced pressure and co-evaporated with CH$_2$Cl$_2$ to give 4-(3-((1-(4-chlorophenyl)-2-oxo-2-(6-((trifluoromethyl)thio)indolin-1-yl)ethyl)amino)-5-methoxyphenoxy)butanoic acid (Compound 11, 164 mg).

Compound 11:
$^1$H NMR (360 MHz, DMSO-d$_6$) δ ppm 1.87 (quin, J=7.1 Hz, 2H) 2.25-2.38 (m, 2H) 3.16-3.27 (m, 2H) 3.62 (s, 3H) 3.81-3.87 (m, 2H) 3.95-4.08 (m, 1H) 4.44-4.56 (m, 1H) 5.57 (br d, J=8.8 Hz, 1H) 5.74-5.77 (m, 1H) 5.90-5.98 (m, 2H) 6.47 (br d, J=8.8 Hz, 1H) 7.34-7.40 (m, 2H) 7.41-7.48 (m, 2H) 7.51-7.59 (m, 2H) 8.39 (s, 1H) 12.16 (br s, 1H)
LC/MS (method LC-C): R$_t$ 1.12 min, MH$^+$ 595

TABLE

| compounds prepared as described above | | |
|---|---|---|
| Compound | Structure | Optical rotation |
| 1 | 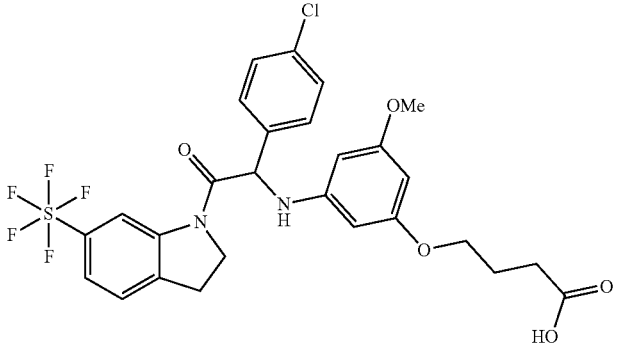 [SMILES: COc1cc(NC(C(=O)N2CCc3ccc(S(F)(F)(F)(F)F)cc32)c2ccc(Cl)cc2)cc(OCCCC(=O)O)c1] | racemic |
| 1A | 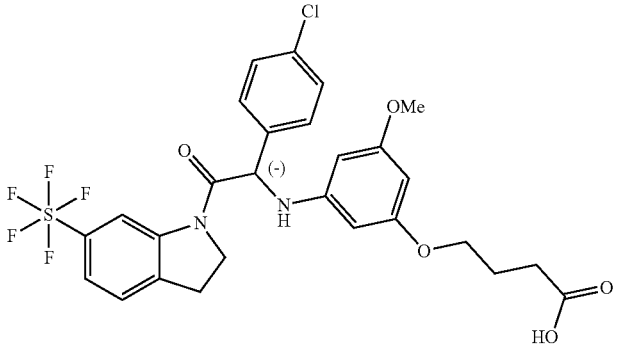 [SMILES: COc1cc(NC(C(=O)N2CCc3ccc(S(F)(F)(F)(F)F)cc32)c2ccc(Cl)cc2)cc(OCCCC(=O)O)c1] | [α]$_D^{20}$ = −44.6° |

TABLE-continued
compounds prepared as described above
| Compound | Structure | Optical rotation |
|---|---|---|
| 1B | 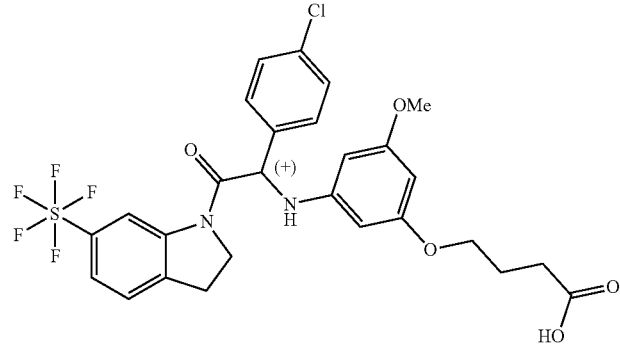 [SMILES: COc1cc(NC(C(=O)N2CCc3ccc(S(F)(F)(F)(F)F)cc32)c2ccc(Cl)cc2)cc(OCCCC(=O)O)c1] | $[\alpha]_D^{20} = +46.0°$ |
| 2 | 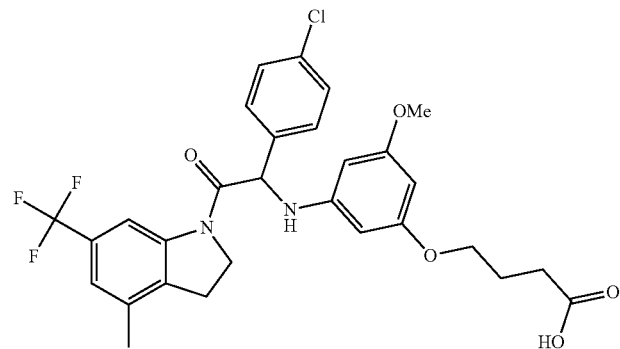 [SMILES: COc1cc(NC(C(=O)N2CCc3c(C)cc(C(F)(F)F)cc32)c2ccc(Cl)cc2)cc(OCCCC(=O)O)c1] | racemic |
| 2A | 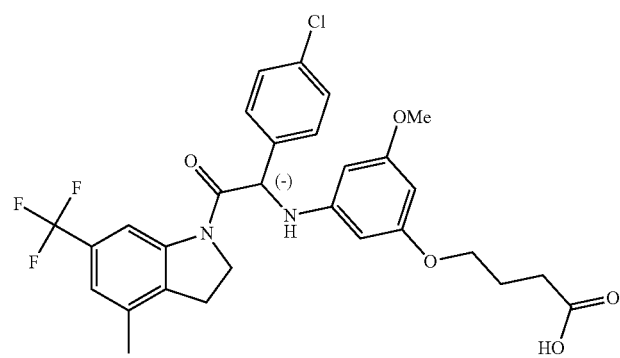 [SMILES: COc1cc(NC(C(=O)N2CCc3c(C)cc(C(F)(F)F)cc32)c2ccc(Cl)cc2)cc(OCCCC(=O)O)c1] | $[\alpha]_D^{20} = -39.0°$ |
| 2B | 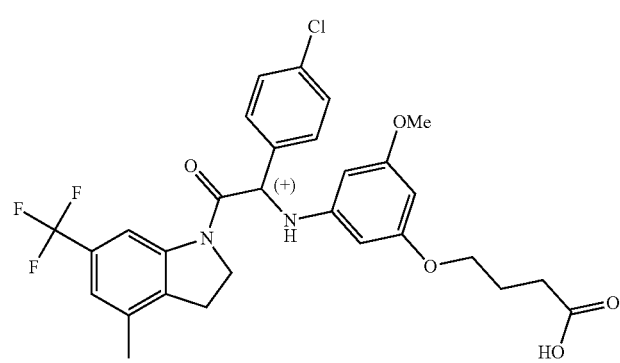 [SMILES: COc1cc(NC(C(=O)N2CCc3c(C)cc(C(F)(F)F)cc32)c2ccc(Cl)cc2)cc(OCCCC(=O)O)c1] | $[\alpha]_D^{20} = +47.1°$ |

TABLE-continued compounds prepared as described above

| Compound | Structure | Optical rotation |
|---|---|---|
| 3 | 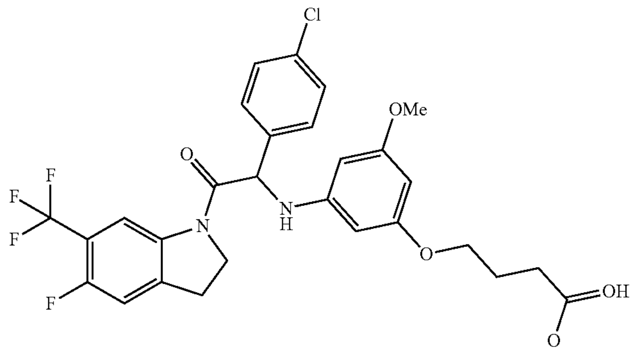 [SMILES: COc1cc(NC(C(=O)N2CCc3cc(F)c(C(F)(F)F)cc32)c2ccc(Cl)cc2)cc(OCCCC(=O)O)c1] | racemic |
| 3A | 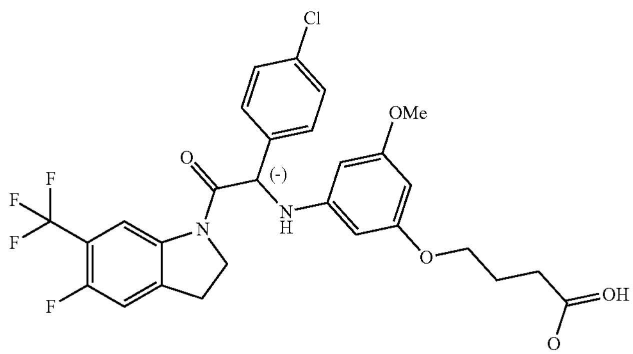 [SMILES: COc1cc(NC(C(=O)N2CCc3cc(F)c(C(F)(F)F)cc32)c2ccc(Cl)cc2)cc(OCCCC(=O)O)c1] | $[\alpha]_D^{20} = -48.9°$ |
| 3B | 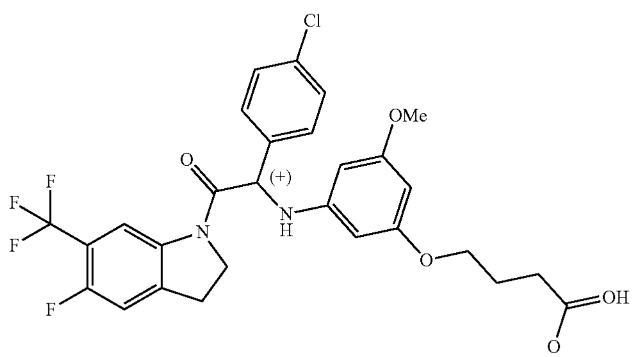 [SMILES: COc1cc(NC(C(=O)N2CCc3cc(F)c(C(F)(F)F)cc32)c2ccc(Cl)cc2)cc(OCCCC(=O)O)c1] | $[\alpha]_D^{20} = +47.8°$ |
| 4 | 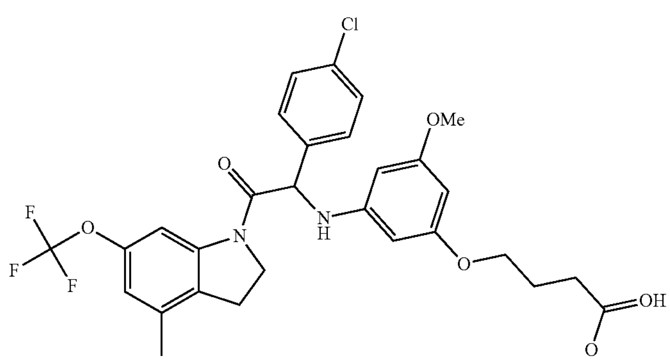 [SMILES: COc1cc(NC(C(=O)N2CCc3c(C)cc(OC(F)(F)F)cc32)c2ccc(Cl)cc2)cc(OCCCC(=O)O)c1] | racemic |

TABLE-continued compounds prepared as described above

| Compound | Structure | Optical rotation |
|---|---|---|
| 4A | 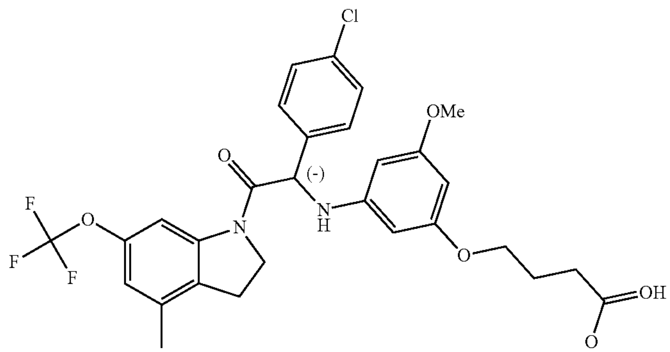 [SMILES: COc1cc(NC(C(=O)N2CCc3c(C)cc(OC(F)(F)F)cc32)c2ccc(Cl)cc2)cc(OCCCC(=O)O)c1] | $[\alpha]_D^{20} = -39.6°$ |
| 4B | 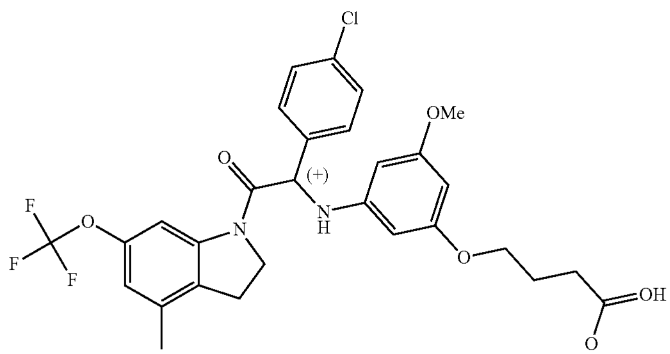 [SMILES: COc1cc(NC(C(=O)N2CCc3c(C)cc(OC(F)(F)F)cc32)c2ccc(Cl)cc2)cc(OCCCC(=O)O)c1] | $[\alpha]_D^{20} = +43.7°$ |
| 5 | 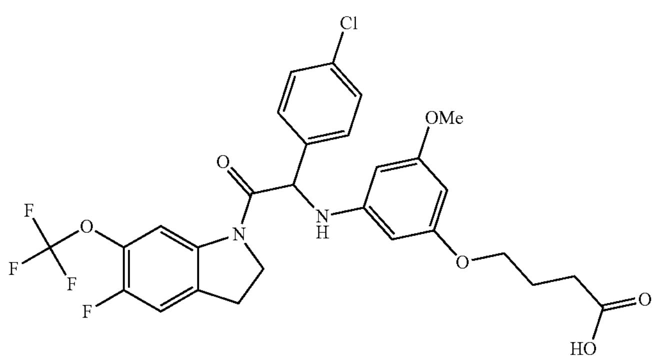 [SMILES: COc1cc(NC(C(=O)N2CCc3cc(F)c(OC(F)(F)F)cc32)c2ccc(Cl)cc2)cc(OCCCC(=O)O)c1] | racemic |
| 5A | 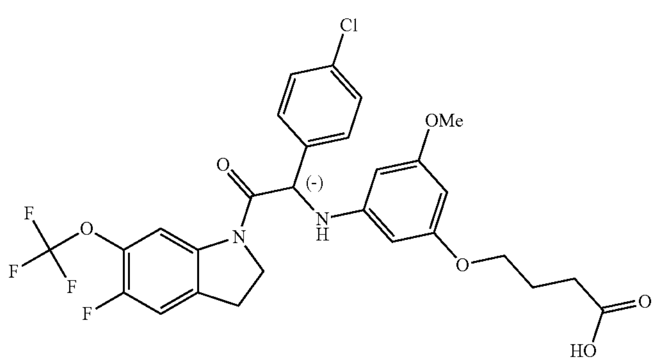 [SMILES: COc1cc(NC(C(=O)N2CCc3cc(F)c(OC(F)(F)F)cc32)c2ccc(Cl)cc2)cc(OCCCC(=O)O)c1] | $[\alpha]_D^{20} = -35.8°$ |

TABLE-continued compounds prepared as described above

| Compound | Structure | Optical rotation |
|---|---|---|
| 5B | 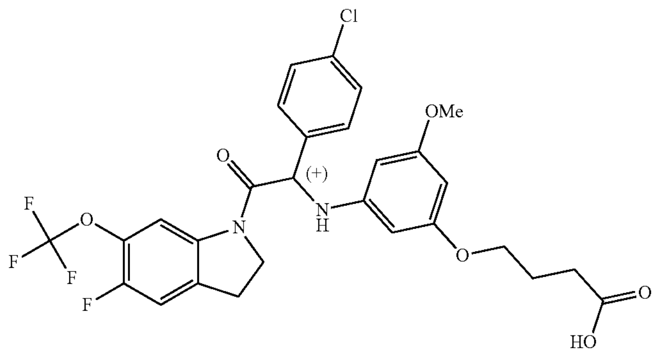 [SMILES: COc1cc(NC(C(=O)N2CCc3cc(F)c(OC(F)(F)F)cc32)c2ccc(Cl)cc2)cc(OCCCC(=O)O)c1] | $[\alpha]_D^{20} = +52.8°$ |
| 6 | 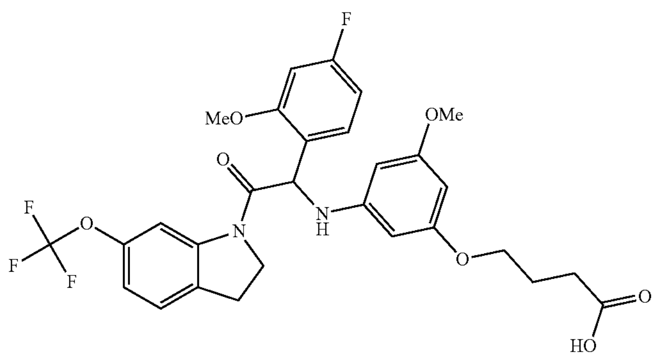 [SMILES: COc1cc(NC(C(=O)N2CCc3ccc(OC(F)(F)F)cc32)c2ccc(F)cc2OC)cc(OCCCC(=O)O)c1] | racemic |
| 6A | 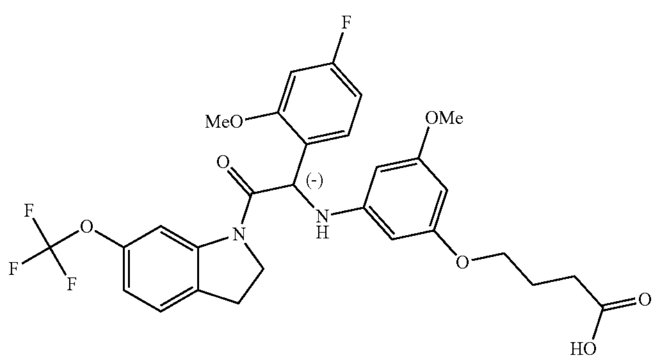 [SMILES: COc1cc(NC(C(=O)N2CCc3ccc(OC(F)(F)F)cc32)c2ccc(F)cc2OC)cc(OCCCC(=O)O)c1] | $[\alpha]_D^{20} = -37.3°$ |
| 6B | 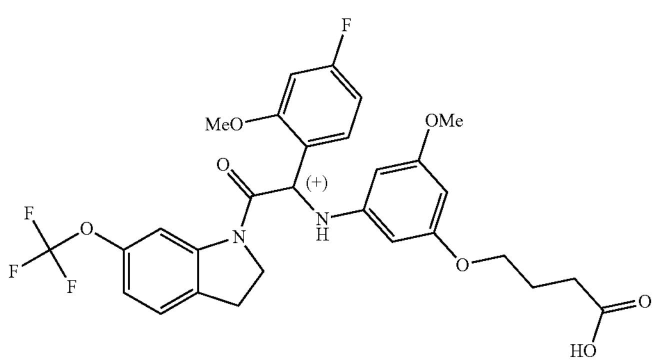 [SMILES: COc1cc(NC(C(=O)N2CCc3ccc(OC(F)(F)F)cc32)c2ccc(F)cc2OC)cc(OCCCC(=O)O)c1] | $[\alpha]_D^{20} = +32.7°$ |

TABLE-continued compounds prepared as described above

| Compound | Structure | Optical rotation |
| --- | --- | --- |
| 7A-D | 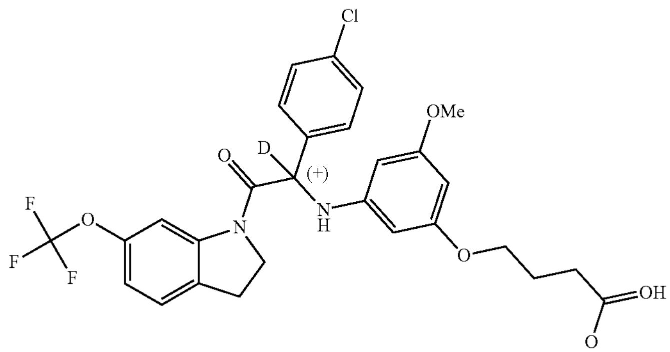 [SMILES: [2H]C(Nc1cc(OC)cc(OCCCC(=O)O)c1)(C(=O)N1CCc2ccc(OC(F)(F)F)cc21)c1ccc(Cl)cc1] | $[\alpha]_D^{20} = +54.2°$ |
| 7B-D | 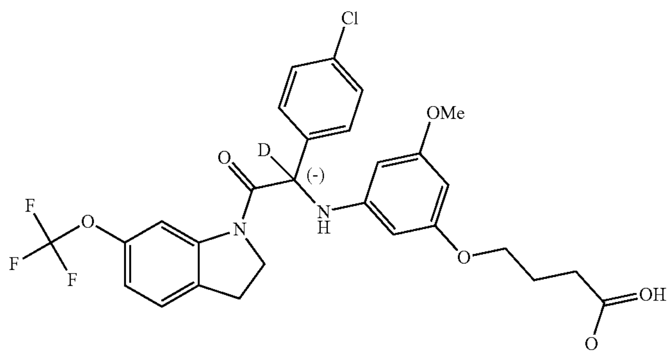 [SMILES: [2H]C(Nc1cc(OC)cc(OCCCC(=O)O)c1)(C(=O)N1CCc2ccc(OC(F)(F)F)cc21)c1ccc(Cl)cc1] | $[\alpha]_D^{20} = -50.1°$ |
| 8 | 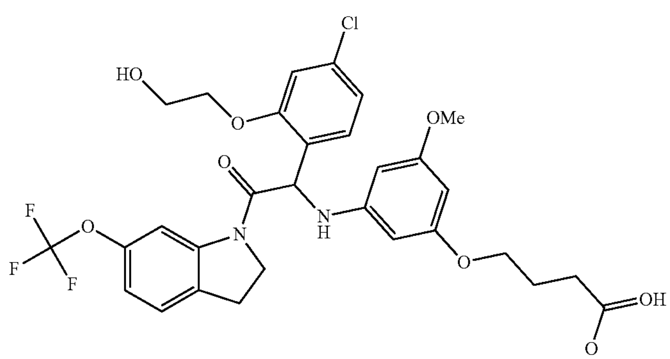 [SMILES: COc1cc(NC(C(=O)N2CCc3ccc(OC(F)(F)F)cc32)c2ccc(Cl)cc2OCCO)cc(OCCCC(=O)O)c1] | racemic |
| 9 | 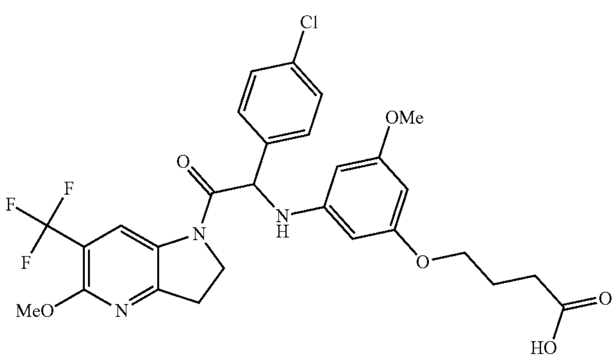 [SMILES: COc1cc(NC(C(=O)N2CCc3nc(OC)c(C(F)(F)F)cc32)c2ccc(Cl)cc2)cc(OCCCC(=O)O)c1] | racemic |

TABLE-continued compounds prepared as described above

| Compound | Structure | Optical rotation |
|---|---|---|
| 10 | 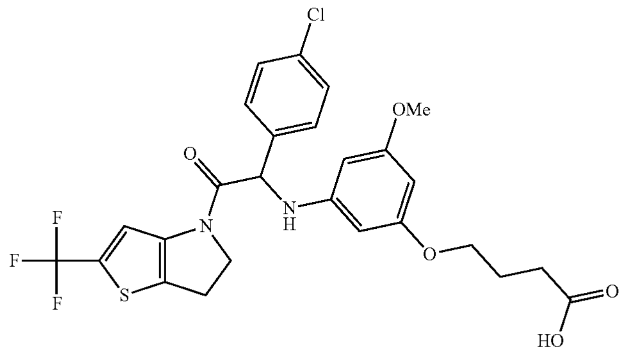 [SMILES: COc1cc(NC(C(=O)N2CCc3sc(C(F)(F)F)cc32)c2ccc(Cl)cc2)cc(OCCCC(=O)O)c1] | racemic |
| 10A | 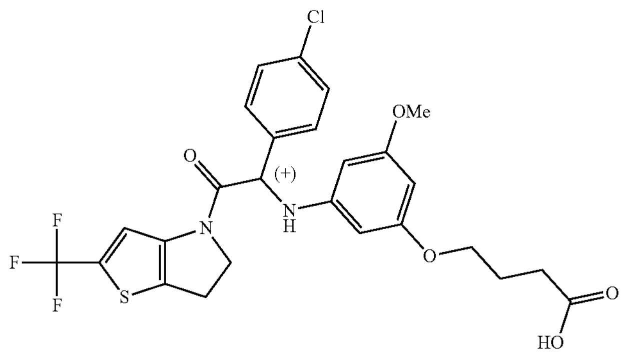 [SMILES: COc1cc(NC(C(=O)N2CCc3sc(C(F)(F)F)cc32)c2ccc(Cl)cc2)cc(OCCCC(=O)O)c1] | $[\alpha]_D^{20} = +36.9°$ |
| 10B | 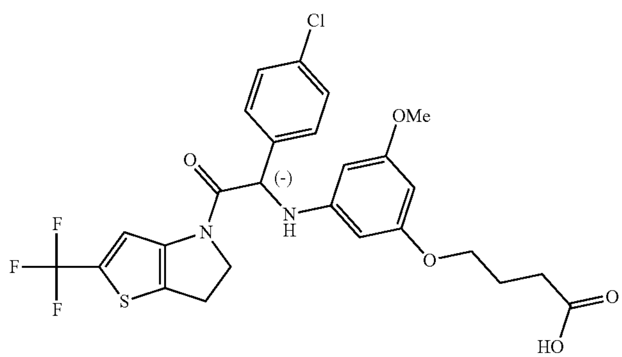 [SMILES: COc1cc(NC(C(=O)N2CCc3sc(C(F)(F)F)cc32)c2ccc(Cl)cc2)cc(OCCCC(=O)O)c1] | $[\alpha]_D^{20} = -39.1°$ |
| 11 | 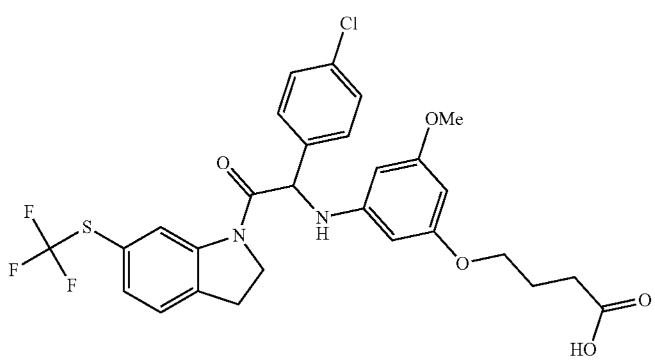 [SMILES: COc1cc(NC(C(=O)N2CCc3ccc(SC(F)(F)F)cc32)c2ccc(Cl)cc2)cc(OCCCC(=O)O)c1] | racemic |

Antiviral Activity of the Compounds of the Invention
DENV-2 Antiviral Assay

The antiviral activity of all the compounds of the invention was tested against the DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 µL was added to 384-well plates (2500 cells/well), which already contain the antiviral compounds. Typically, these plates contain a 5-fold serial dilution of 9 dilution steps of the test compound at 200 times the final concentration in 100% DMSO (200 nL). In addition, each compound concentration is tested in quadruplicate (final concentration range: 25 µM-0.000064 µM or 2.5 µM-0.0000064 µM for the most active compounds). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 µL of culture medium was added instead of Vero cells. Once the cells are added to the plates, the plates were incubated for 30 minutes at room temperature to allow the cells to distribute evenly within the wells. Next, the plates were incubated in a fully humidified incubator (37° C., 5% $CO_2$) until the next day. Then, DENV-2 strain 16681, labeled with eGFP, was added at a multiplicity of infection (MOI) of 0.5. Therefore, 15 µL of virus suspension was added to all the wells containing test compound and to the wells assigned as virus control. In parallel, 15 µL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration ($EC_{50}$) was determined. Therefore, the percent inhibition (I) for every test concentration is calculated using the following formula: $I=100*(S_T-S_{CC})/(S_{VC}-S_{CC})$; $S_T$, $S_{CC}$ and $S_{VC}$ are the amount of eGFP signal in the test compound, cell control and virus control wells, respectively. The $EC_{50}$ represents the concentration of a compound at which the virus replication is inhibited with 50%, as measured by a 50% reduction of the eGFP fluorescent intensity compared to the virus control. The $EC_{50}$ is calculated using linear interpolation (Table 1).

In parallel, the toxicity of the compounds was assessed on the same plates. Once the read-out for the eGFP signal was done, 40 µL of ATPlite, a cell viability stain, was added to all wells of the 384-well plates. ATP is present in all metabolically active cells and the concentration declines very rapidly when the cells undergo necrosis or apoptosis. The ATPLite assay system is based on the production of light caused by the reaction of ATP with added luciferase and D-luciferin. The plates were incubated for 10 minutes at room temperature. Next, the plates were measured on a ViewLux. The half maximal cytotoxic concentration ($CC_{50}$) was also determined, defined as the concentration required to reduce the luminescent signal by 50% compared to that of the cell control wells. Finally, the selectivity index (SI) was determined for the compounds, which was calculated as followed: $SI=CC_{50}/EC_{50}$.

TABLE 1

$EC_{50}$, $CC_{50}$, and SI for the compounds of the invention in the DENV-2 antiviral assay

| compound# | $EC_{50}$ (µM) | N | $CC_{50}$ (µM) | N | SI | N |
|---|---|---|---|---|---|---|
| 1 | 0.00064 | 3 | 13 | 4 | 19800 | 3 |
| 1A | 0.0013 | 3 | 12 | 3 | 9200 | 3 |
| 1B | 0.00011 | 3 | 13 | 4 | 104092 | 3 |
| 2 | 0.00038 | 3 | 12 | 4 | 32100 | 3 |

TABLE 1-continued $EC_{50}$, $CC_{50}$, and SI for the compounds of the invention in the DENV-2 antiviral assay

| compound# | $EC_{50}$ (µM) | N | $CC_{50}$ (µM) | N | SI | N |
|---|---|---|---|---|---|---|
| 2A | 0.015 | 3 | 12 | 3 | 799 | 3 |
| 2B | 0.000078 | 4 | 14 | 4 | 166670 | 4 |
| 3 | 0.00056 | 3 | 13 | 3 | 22700 | 3 |
| 3A | 0.036 | 3 | 12 | 3 | 346 | 3 |
| 3B | 0.00012 | 3 | 13 | 3 | 91000 | 3 |
| 4 | 0.00011 | 4 | 12 | 4 | 96000 | 4 |
| 4A | 0.011 | 3 | 13 | 3 | 1180 | 3 |
| 4B | 0.000057 | 4 | 13 | 4 | 186421 | 4 |
| 5 | 0.00011 | 3 | 10 | 3 | 90900 | 3 |
| 5A | 0.0023 | 6 | 10 | 9 | 4440 | 6 |
| 5B | 0.00012 | 4 | 12 | 4 | >54214 | 4 |
| 6 | 0.00063 | 3 | 12 | 3 | 19500 | 3 |
| 6A | 0.25 | 3 | 11 | 3 | 46 | 3 |
| 6B | 0.00039 | 3 | 15 | 4 | 39700 | 3 |
| 7A-D | 0.000100 | 3 | 12 | 3 | 118813 | 3 |
| 7B-D | 0.016 | 3 | 9.6 | 3 | 584 | 3 |
| 8 | 0.00015 | 3 | 13 | 4 | 86800 | 3 |
| 9 | 0.00099 | 4 | 12 | 4 | 12600 | 4 |
| 10 | 0.00052 | 3 | 19 | 3 | 40900 | 3 |
| 10A | 0.00030 | 3 | 14 | 3 | 58900 | 3 |
| 10B | 0.037 | 3 | 12 | 3 | 330 | 3 |
| 11 | 0.00028 | 3 | 13 | 3 | 43300 | 3 |

N = the number of independent experiments in which the compounds were tested.

Tetravalent Reverse Transcriptase Quantitative-PCR (RT-qPCR) Assay

The antiviral activity of the compounds of the invention was tested against DENV-1 strain TC974 #666 (NCPV), DENV-2 strain 16681, DENV-3 strain H87 (NCPV) and DENV-4 strain H241 (NCPV) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; Table 2) and a cellular reference gene (β-actin, Table 2). Subsequently, a duplex real time PCR was performed on a Lightcycler480 instrument. The generated Cp value is inversely proportional to the amount of RNA expression of these targets. Inhibition of DENV replication by a test compound results in a shift of Cp's for the 3'UTR gene. On the other hand, if a test compound is toxic to the cells, a similar effect on β-actin expression will be observed. The comparative ΔΔCp method is used to calculate $EC_{50}$, which is based on the relative gene expression of the target gene (3'UTR) normalized with the cellular housekeeping gene (β-actin). In addition, $CC_{50}$ values are determined based on the $C_p$ values acquired for the housekeeping gene β-actin.

TABLE 2

Primers and probes used for the real-time, quantitative RT-PCR.

| Primer/probe | Target | Sequence[a,b] |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |
| P3utr343 | DENV 3'-UTR | ***FAM*-5'-AAGGACTAG-*ZEN*-AGGTTAGAGGAGACCCCCC-3'-*IABkFQ*** |
| Factin743 | β-actin | 5'-GGCCAGGTCATCACCATT-3' |
| Ractin876 | β-actin | 5'-ATGTCCACGTCACACTTCATG-3' |
| Pactin773 | β-actin | ***HEX*-5'-TTCCGCTGC-*ZEN*-CCTGAGGCTCTC-3' *IABkFQ*** |

[a]Reporter dyes (FAM, HEX) and quenchers (ZEN and IABkFQ) elements are indicated in bold and italics.
[b]The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 μL/well was added in 96-well plates (10000 cells/well), which already contain the antiviral compounds. Typically, these plates contain a 5-fold serial dilution of 9 dilution steps of the test compound at 200 times the final concentration in 100% DMSO (500 nL; final concentration range: 25 μM-0.000064 μM or 2.5 μM-0.0000064 μM for the most active compounds). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% $CO_2$) until the next day. Dengue viruses serotype-1, 2, 3 and 4 were diluted in order to obtain a Cp of ~22-24 in the assay. Therefore, 25 μL of virus suspension was added to all the wells containing test compound and to the wells assigned as virus control. In parallel, 25 μL of culture medium was added to the cell controls. Next, the plates were incubated for 3 days in a fully humidified incubator (37° C., 5% $CO_2$). After 3 days, the supernatant was removed from the wells and the cells were washed twice with ice-cold PBS (~100 μL). The cell pellets within the 96-well plates were stored at −80° C. for at least 1 day. Next, RNA was extracted using the Cells-to-CT™ lysis kit, according to the manufacturer's guideline (Life Technologies). The cell lysates can be stored at −80° C. or immediately used in the reverse transcription step.

In preparation of the reverse transcription step, mix A (table 3A) was prepared and 7.57 μL/well was dispensed in a 96-well plate. After addition of 5 μL of the cell lysates, a five minute denaturation step at 75° C. was performed (table 3B). Afterwards, 7.43 μL of mix B was added (table 3C) and the reverse transcription step was initiated (table 3D) to generate cDNA.

Finally, a RT-qPCR mix was prepared, mix C (table 4A), and 22.02 μL/well was dispensed in 96-well LightCycler qPCR plates to which 3 μL of cDNA was added and the qPCR was performed according to the conditions in table 4B on a LightCycler 480.

Using the LightCycler software and an in-house LIMS system, dose response curves for each compound were calculated and the half maximal effective concentration ($EC_{50}$) and the half maximal cytotoxic concentration ($CC_{50}$) were determined (Tables 5-8).

TABLE 3 cDNA synthesis using Mix A, denaturation, Mix B and reverse transcription.

| A | Mix A | | | | |
|---|---|---|---|---|---|
| Plates | 8 | | Reaction Vol. (μl) | 20 | |
| Samples | 828 | | | | |

| | | Concentration | | Volume for (μl) | |
|---|---|---|---|---|---|
| Mix Item | Unit | Stock | Final | 1 sample | x samples |
| Milli-Q $H_2O$ | | | | 7.27 | 6019.56 |
| R3utr425 | μM | 20 | 0.27 | 0.15 | 124.20 |
| Ractin876 | μM | 20 | 0.27 | 0.15 | 124.20 |
| Volume mix/well (μl) | | | | 7.57 | |
| Cell lysates | | | | 5.00 | |

| B | Denaturation step: | | |
|---|---|---|---|
| Step | Temp | | Time |
| Denaturation | 75° C. | | 5' |
| Hold | 4° C. | | hold |

| C | Mix B | | | | |
|---|---|---|---|---|---|
| Samples | 864 | | | | |

| | | Concentration | | Volume for (μl) | |
|---|---|---|---|---|---|
| Mix Item | Unit | Stock | Final | 1 sample | x samples |
| Expand HIFI buffer 2 | X | 10.00 | 1.00 | 2.00 | 1728.0 |
| $MgCl_2$ | mM | 25.00 | 3.50 | 2.80 | 2419.2 |
| dNTPs | mM | 10.00 | 1.00 | 2.00 | 1728.0 |
| Rnase inhibitor | U/μl | 40.00 | 1.00 | 0.50 | 432.0 |
| Expand RT | U/μl | 50.00 | 0.33 | 0.13 | 112.3 |
| Total Volume Mix (μl) | | | | 7.43 | |

TABLE 3-continued cDNA synthesis using Mix A, denaturation, Mix B and reverse transcription.

D Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A Mix C

| Samples | | 833 | | Reaction Vol. (μl) | 25 |
|---|---|---|---|---|---|

| | | Concentration | | Volume for (μl) | |
|---|---|---|---|---|---|
| Mix Item | Unit | Stock | Final | 1 sample | x samples |
| H$_2$O PCR grade Roche | | | | 7.74 | 6447.42 |
| Roche 2 × MM mix | X | 2 | 1 | 12.50 | 10412.50 |
| F3utr258 | μM | 20 | 0.3 | 0.38 | 316.54 |
| R3utr425 | μM | 20 | 0.3 | 0.38 | 316.54 |
| P3utr343 | μM | 20 | 0.1 | 0.13 | 108.29 |
| Factin743 | μM | 20 | 0.3 | 0.38 | 316.54 |
| Ractin876 | μM | 20 | 0.3 | 0.38 | 316.54 |
| Pactin773 | μM | 20 | 0.1 | 0.13 | 108.29 |
| | | Volume Mix/Tube (μl) | | 22.02 | |
| | | cDNA | | 3.00 | |

B Protocol qPCR3

| Step | Temp | Time | Ramp rate | |
|---|---|---|---|---|
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

TABLE 5

EC$_{50}$, CC$_{50}$, and SI for the compounds against serotype 1 in the RT-qPCR assays

| | RT-GPCR serotype 1 TC974#666 | | | | | |
|---|---|---|---|---|---|---|
| compound# | EC$_{50}$ (μM) | N | CC$_{50}$ (μM) | N | SI | N |
| 1B | 0.000096 | 4 | >2.5 | 4 | >79500 | 4 |
| 2B | 0.000091 | 5 | >1.0 | 5 | >33100 | 5 |
| 3B | 0.00010 | 3 | >2.5 | 3 | >54200 | 3 |
| 4B | 0.00011 | 4 | >1.0 | 4 | >45200 | 4 |
| 5B | 0.00033 | 3 | >1.0 | 3 | >5910 | 3 |
| 6B | 0.00064 | 4 | 13 | 4 | 20500 | 4 |
| 7A-D | 0.00024 | 3 | >1.0 | 3 | >6180 | 3 |
| 10A | 0.00022 | 5 | 13 | 5 | 56000 | 5 |

N = the number of independent experiments in which the compounds were tested.

TABLE 6

EC$_{50}$, CC$_{50}$, and SI for the compounds against serotype 2 in the RT-qPCR assays

| | RT-qPCR serotype 2 16681 | | | | | |
|---|---|---|---|---|---|---|
| compound# | EC$_{50}$ (μM) | N | CC$_{50}$ (μM) | N | SI | N |
| 1B | 0.00018 | 4 | >2.5 | 4 | >11700 | 4 |
| 2B | 0.000061 | 4 | >1.0 | 4 | >36300 | 4 |
| 3B | 0.000096 | 3 | >2.5 | 3 | >46900 | 3 |
| 4B | 0.000067 | 4 | >1.0 | 4 | >39400 | 4 |
| 5B | 0.00029 | 3 | >1.0 | 3 | >5770 | 3 |
| 6B | 0.00041 | 3 | 15 | 4 | 28100 | 3 |
| 7A-D | 0.00016 | 3 | >1.0 | 3 | >9330 | 3 |
| 10A | 0.00011 | 6 | 15 | 5 | 131977 | 5 |

N = the number of independent experiments in which the compounds were tested.

TABLE 7

EC$_{50}$, CC$_{50}$, and SI for the compounds against serotype 3 in the RT-qPCR assays RT-qPCR serotype 3 H87

| compound# | EC$_{50}$ (MM) | N | CC$_{50}$ (MM) | N | SI | N |
|---|---|---|---|---|---|---|
| 1B | 0.0019 | 4 | >2.5 | 4 | >1590 | 4 |
| 2B | 0.00085 | 4 | >1.0 | 4 | >2050 | 4 |
| 3B | 0.0015 | 3 | >2.5 | 3 | >3870 | 3 |
| 4B | 0.00092 | 4 | >1.0 | 4 | >2360 | 4 |
| 5B | 0.0026 | 3 | >1.0 | 3 | >719 | 3 |
| 6B | 0.0056 | 4 | 13 | 4 | 2520 | 4 |
| 7A-D | 0.0024 | 3 | >1.0 | 3 | >574 | 3 |
| 10A | 0.0042 | 5 | 15 | 5 | 6210 | 5 |

N = the number of independent experiments in which the compounds were tested.

TABLE 8

EC$_{50}$, CC$_{50}$, and SI for the compounds against serotype 4 in the RT-qPCR assays RT-qPCR serotype 4 H241

| compound# | EC$_{50}$ (μM) | N | CC$_{50}$ (μM) | N | SI | N |
|---|---|---|---|---|---|---|
| 1B | 0.0096 | 4 | 8.8 | 4 | 2980 | 4 |
| 2B | 0.010 | 4 | 4.1 | 4 | 1020 | 4 |
| 3B | 0.014 | 3 | 3.6 | 1 | 333 | 1 |
| 4B | 0.012 | 3 | 6.8 | 2 | 563 | 2 |
| 5B | 0.020 | 3 | 8.4 | 3 | 618 | 3 |
| 6B | 0.029 | 4 | 9.7 | 3 | 317 | 3 |
| 7A-D | 0.013 | 3 | 8.2 | 3 | 1000 | 3 |
| 10A | 0.030 | 5 | 3.2 | 5 | 105 | 5 |

N = the number of independent experiments in which the compounds were tested.

The invention claimed is:

1. A compound of formula (I), or a stereochemically isomeric form thereof,

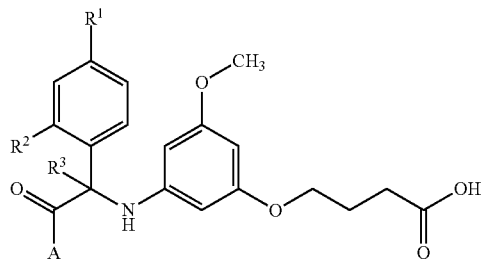
(I)

wherein
A is

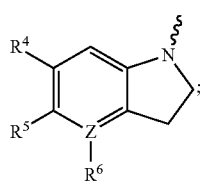
(a-1)

$R^1$ is fluoro, $R^2$ is methoxy, $R^3$ is hydrogen, $R^4$ is trifluoromethoxy, $R^5$ is hydrogen, Z is carbon, and $R^6$ is hydrogen;
or a pharmaceutically acceptable salt, solvate or polymorph thereof.

2. The compound of claim 1, which is

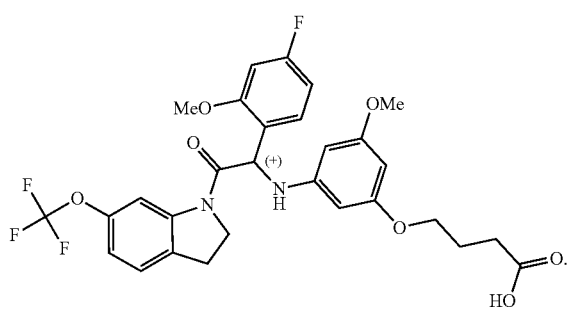 [SMILES: COc1cc(NC(C(=O)N2CCc3ccc(OC(F)(F)F)cc32)c2ccc(F)cc2OC)cc(OCCCC(=O)O)c1]

3. A pharmaceutical composition comprising the compound of claim 1 together with one or more pharmaceutically acceptable excipients, diluents or carriers.

4. The pharmaceutical composition of claim 3, which comprises a second or further active ingredient.

5. The pharmaceutical composition of claim 4, wherein the second or further active ingredient is an antiviral agent.

6. A method of treating or preventing Dengue viral infection or a disease caused by Dengue viral infection, comprising administering to a subject in need thereof an effective amount of the compound of claim 1.

7. The method of claim 6, wherein the Dengue viral infection is an infection by viruses of at least one of the DENV-1, DENV-2, DENV-3 or DENV-4 strain.

8. The method of claim 6, which comprises treating Dengue viral infection or a disease caused by Dengue viral infection.

9. The method of claim 6, which comprises preventing Dengue viral infection or a disease caused by Dengue viral infection.

10. A method of treating or preventing Dengue viral infection or a disease caused by Dengue viral infection comprising administering to a subject in need thereof an effective amount of the pharmaceutical composition of claim 3.

11. The method of claim 10, which comprises treating Dengue viral infection or a disease caused by Dengue viral infection.

12. The method of claim 10, which comprises preventing Dengue viral infection or a disease caused by Dengue viral infection.

13. A method of inhibiting Dengue virus replication in an animal cell, comprising administering to a subject in need thereof an effective amount of the compound of claim 1.

14. A method of inhibiting Dengue virus replication in an animal cell, comprising administering to a subject in need thereof an effective amount of the pharmaceutical composition of claim 3.

* * * * *